US008545984B2

(12) United States Patent
He et al.

(10) Patent No.: US 8,545,984 B2
(45) Date of Patent: Oct. 1, 2013

(54) PHOTOCHROMIC COMPOUNDS AND COMPOSITIONS

(75) Inventors: Meng He, Murrysville, PA (US); Darrin R. Dabideen, Pittsburgh, PA (US); Anil Kumar, Murrysville, PA (US); Ruisong Xu, Monroeville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 108 days.

(21) Appl. No.: 12/928,687

(22) Filed: Dec. 16, 2010

(65) Prior Publication Data

US 2011/0129678 A1   Jun. 2, 2011

Related U.S. Application Data

(63) Continuation-in-part of application No. 12/329,092, filed on Dec. 5, 2008, now Pat. No. 8,211,338, which is a continuation-in-part of application No. 10/846,629, filed on May 17, 2004, now Pat. No. 7,342,112.

(60) Provisional application No. 60/484,100, filed on Jul. 1, 2003.

(51) Int. Cl.
| C07D 311/00 | (2006.01) |
| C07D 311/92 | (2006.01) |
| C09K 9/02 | (2006.01) |
| G02B 5/23 | (2006.01) |
| G03C 1/73 | (2006.01) |

(52) U.S. Cl.
USPC ........ 428/423.1; 252/586; 428/426; 428/447; 428/522; 428/704; 544/111; 544/375; 546/196; 549/382

(58) Field of Classification Search
None
See application file for complete search history.

(56) References Cited

U.S. PATENT DOCUMENTS

| | | |
|---|---|---|
| 2,319,826 A | 5/1943 | Pellett |
| 2,334,446 A | 11/1943 | Serrell |
| 2,475,921 A | 7/1949 | Smith |
| 2,481,830 A | 9/1949 | Dreyer |
| 2,544,659 A | 3/1951 | Dreyer |
| 3,276,316 A | 10/1966 | Makas |
| 3,361,706 A | 1/1968 | Meriwether et al. |
| 3,653,863 A | 4/1972 | Araujo et al. |
| 4,039,254 A | 8/1977 | Harsch |
| 4,043,637 A | 8/1977 | Hovey |
| 4,049,338 A | 9/1977 | Slocum |
| 4,166,043 A | 8/1979 | Uhlmann et al. |
| 4,190,330 A | 2/1980 | Berreman |
| 4,279,474 A | 7/1981 | Belgorod |
| 4,367,170 A | 1/1983 | Uhlmann et al. |
| 4,539,048 A | 9/1985 | Cohen |
| 4,539,049 A | 9/1985 | Cohen |
| 4,549,894 A | 10/1985 | Araujo et al. |
| 4,556,605 A | 12/1985 | Mogami et al. |
| 4,637,896 A | 1/1987 | Shannon |
| 4,648,925 A | 3/1987 | Goepfert et al. |
| 4,650,526 A | 3/1987 | Claffey et al. |
| 4,683,153 A | 7/1987 | Goepfert et al. |
| 4,685,783 A | 8/1987 | Heller et al. |
| 4,720,356 A | 1/1988 | Chu |
| 4,728,173 A | 3/1988 | Toth |
| 4,756,605 A | 7/1988 | Okada et al. |
| 4,756,973 A | 7/1988 | Sakagami et al. |
| 4,785,097 A | 11/1988 | Kwak |
| 4,810,433 A | 3/1989 | Takayanagi et al. |
| 4,838,675 A | 6/1989 | Richards et al. |
| 4,863,763 A | 9/1989 | Takeda et al. |
| 4,865,668 A | 9/1989 | Goepfert et al. |
| 4,873,026 A | 10/1989 | Behre et al. |
| 4,873,029 A | 10/1989 | Blum |
| 4,929,693 A | 5/1990 | Akashi et al. |
| 4,931,220 A | 6/1990 | Haynes et al. |
| 4,931,221 A | 6/1990 | Heller |
| 4,959,471 A | 9/1990 | Melzig |
| 4,962,013 A | 10/1990 | Tateoka et al. |
| 4,974,941 A | 12/1990 | Gibbons et al. |
| 4,977,028 A | 12/1990 | Goepfert et al. |
| 4,983,479 A | 1/1991 | Broer et al. |
| 5,066,818 A | 11/1991 | Gemert et al. |
| 5,067,795 A | 11/1991 | Senatore |
| 5,073,294 A | 12/1991 | Shannon et al. |
| 5,130,058 A | 7/1992 | Tanaka et al. |
| 5,130,353 A | 7/1992 | Fischer et al. |
| 5,139,707 A | 8/1992 | Guglielmetti et al. |
| 5,155,607 A | 10/1992 | Inoue et al. |
| 5,166,345 A | 11/1992 | Akashi et al. |
| 5,180,470 A | 1/1993 | Smith et al. |
| 5,180,524 A | 1/1993 | Casilli et al. |
| 5,185,390 A | 2/1993 | Fischer et al. |
| 5,186,867 A | 2/1993 | Castaldi et al. |
| 5,189,448 A | 2/1993 | Yaguchi |
| 5,194,973 A | 3/1993 | Isogai et al. |
| 5,200,116 A | 4/1993 | Heller |
| 5,202,053 A | 4/1993 | Shannon |

(Continued)

FOREIGN PATENT DOCUMENTS

| EP | 0313941 A1 | 5/1989 |
| EP | 0315224 A1 | 5/1989 |

(Continued)

OTHER PUBLICATIONS

Kvasnikov, E.D. et al., "Birefringence in Polyvinylcinnamate Films Induced by Polarized Light," Doklady Akademii nauk SSSR, 1977, pp. 633-636, vol. 237, No. 3.

(Continued)

*Primary Examiner* — Kamal Saeed
(74) *Attorney, Agent, or Firm* — Deborah M Altman

(57) ABSTRACT

Described herein are compounds generally comprising an indeno[2',3':3,4]naptho[1,2-b]pyran structure. Such compounds may be useful for their photochromic properties, and be used in certain photochromic compositions. Such compositions may further comprise other photochromic compositions and/or materials. Additionally, such compounds and/or compositions may be suitable for preparing certain photochromic articles. Also described herein are methods for preparing certain photochromic compounds, compositions, and articles.

30 Claims, 1 Drawing Sheet

(56) References Cited

U.S. PATENT DOCUMENTS

| | | |
|---|---|---|
| 5,204,850 A | 4/1993 | Obata |
| 5,238,981 A | 8/1993 | Knowles |
| 5,247,377 A | 9/1993 | Omeis et al. |
| 5,274,132 A | 12/1993 | VanGemert |
| 5,289,547 A | 2/1994 | Ligas et al. |
| 5,359,085 A | 10/1994 | Iwamoto et al. |
| 5,359,443 A | 10/1994 | Toyooka et al. |
| 5,389,287 A | 2/1995 | Nishiyama et al. |
| 5,389,698 A | 2/1995 | Chigrinov et al. |
| 5,391,327 A | 2/1995 | Ligas et al. |
| 5,395,566 A | 3/1995 | Kobayakawa et al. |
| 5,464,669 A | 11/1995 | Kang et al. |
| 5,543,267 A | 8/1996 | Stumpe et al. |
| 5,543,533 A | 8/1996 | Allegrini et al. |
| 5,602,661 A | 2/1997 | Schadt et al. |
| 5,608,567 A | 3/1997 | Grupp |
| 5,641,846 A | 6/1997 | Bieringer et al. |
| 5,644,416 A | 7/1997 | Morikawa et al. |
| 5,645,767 A | 7/1997 | Van Gemert |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,744,070 A | 4/1998 | Kumar |
| 5,746,949 A | 5/1998 | Shen et al. |
| 5,770,115 A | 6/1998 | Misura |
| 5,808,100 A | 9/1998 | Momoda et al. |
| 5,831,090 A | 11/1998 | Paltchkov et al. |
| 5,846,452 A | 12/1998 | Gibbons et al. |
| 5,869,658 A | 2/1999 | Lin et al. |
| 5,903,330 A | 5/1999 | Funfschilling et al. |
| 5,943,104 A | 8/1999 | Moddel et al. |
| 5,952,515 A | 9/1999 | Melzig et al. |
| 5,955,520 A | 9/1999 | Heller et al. |
| 5,961,892 A | 10/1999 | Gemert et al. |
| 5,962,617 A | 10/1999 | Slagel |
| 6,004,486 A | 12/1999 | Chan |
| 6,022,497 A | 2/2000 | Kumar |
| 6,025,026 A | 2/2000 | Smith et al. |
| 6,036,890 A | 3/2000 | Melzig et al. |
| 6,049,428 A | 4/2000 | Khan et al. |
| 6,060,001 A | 5/2000 | Welch et al. |
| 6,080,338 A | 6/2000 | Kumar |
| 6,096,375 A | 8/2000 | Ouderkirk et al. |
| 6,106,744 A | 8/2000 | Van Gemert et al. |
| 6,113,814 A | 9/2000 | Gemert et al. |
| 6,136,968 A | 10/2000 | Chamontin et al. |
| 6,141,135 A | 10/2000 | Nagoh et al. |
| 6,146,554 A | 11/2000 | Melzig et al. |
| 6,150,430 A | 11/2000 | Walters et al. |
| 6,153,126 A | 11/2000 | Kumar |
| 6,160,597 A | 12/2000 | Schadt et al. |
| 6,187,444 B1 | 2/2001 | Bowles, III et al. |
| 6,208,393 B1 | 3/2001 | Bawolek et al. |
| 6,239,778 B1 | 5/2001 | Palffy-Muhoray et al. |
| 6,245,399 B1 | 6/2001 | Sahouani et al. |
| 6,256,152 B1 | 7/2001 | Coldrey et al. |
| 6,268,055 B1 | 7/2001 | Walters et al. |
| 6,281,366 B1 | 8/2001 | Frigoli et al. |
| 6,284,418 B1 | 9/2001 | Trantolo |
| 6,294,112 B1 | 9/2001 | Clarke et al. |
| 6,296,785 B1 | 10/2001 | Nelson et al. |
| 6,303,673 B1 | 10/2001 | Clarke et al. |
| 6,312,811 B1 | 11/2001 | Frigoli et al. |
| 6,334,681 B1 | 1/2002 | Perrott et al. |
| 6,337,409 B1 | 1/2002 | Hughes et al. |
| 6,338,808 B1 | 1/2002 | Kawata et al. |
| 6,340,766 B1 | 1/2002 | Lin |
| 6,348,604 B1 | 2/2002 | Nelson et al. |
| 6,353,102 B1 | 3/2002 | Kumar |
| 6,369,869 B2 | 4/2002 | Schadt et al. |
| 6,432,544 B1 | 8/2002 | Stewart et al. |
| 6,433,043 B1 | 8/2002 | Misura et al. |
| 6,436,525 B1 | 8/2002 | Welch et al. |
| 6,474,695 B1 | 11/2002 | Schneider et al. |
| 6,506,488 B1 | 1/2003 | Stewart et al. |
| 6,531,076 B2 | 3/2003 | Crano et al. |
| 6,555,028 B2 | 4/2003 | Walters et al. |
| 6,555,029 B1 | 4/2003 | Ruscio et al. |
| 6,579,422 B1 | 6/2003 | Kakinuma |
| 6,597,422 B1 | 7/2003 | Funfschilling et al. |
| 6,602,603 B2 | 8/2003 | Welch et al. |
| 6,613,433 B2 | 9/2003 | Yamamoto et al. |
| 6,630,597 B1 | 10/2003 | Lin et al. |
| 6,641,874 B2 | 11/2003 | Kuntz et al. |
| 6,660,727 B1 | 12/2003 | Mann et al. |
| 6,683,709 B2 | 1/2004 | Mann et al. |
| 6,690,495 B1 | 2/2004 | Kosa et al. |
| 6,705,569 B1 | 3/2004 | Sanders et al. |
| 6,717,644 B2 | 4/2004 | Schadt et al. |
| 6,723,859 B2 | 4/2004 | Kawabata et al. |
| 6,736,998 B2 | 5/2004 | Petrovskaia et al. |
| 6,761,452 B2 | 7/2004 | Moravec et al. |
| 6,797,383 B2 | 9/2004 | Nishizawa et al. |
| 6,806,930 B2 | 10/2004 | Moia |
| 6,844,686 B1 | 1/2005 | Schneck et al. |
| 6,874,888 B1 | 4/2005 | Dudai |
| 6,891,038 B2 | 5/2005 | Krongauz et al. |
| 6,986,946 B2 | 1/2006 | Nishizawa et al. |
| 7,008,568 B2 | 3/2006 | Qin |
| 7,097,303 B2 | 8/2006 | Kumar et al. |
| 7,118,806 B2 | 10/2006 | Nishizawa et al. |
| 7,166,357 B2 | 1/2007 | Kumar et al. |
| 7,247,262 B2 | 7/2007 | Evans et al. |
| 7,256,921 B2 | 8/2007 | Kumar et al. |
| 7,262,295 B2 | 8/2007 | Walters et al. |
| 7,320,826 B2 | 1/2008 | Kumar et al. |
| 7,342,112 B2 | 3/2008 | Kumar et al. |
| 7,357,503 B2 | 4/2008 | Mosse et al. |
| 7,416,682 B2 | 8/2008 | Frigoli et al. |
| 7,465,415 B2 | 12/2008 | Wang et al. |
| 7,521,004 B2 | 4/2009 | Momoda et al. |
| 7,557,208 B2 | 7/2009 | Walters et al. |
| 7,582,749 B2 * | 9/2009 | Kumar et al. ............ 540/114 |
| 2002/0039627 A1 | 4/2002 | Ichihashi et al. |
| 2002/0090516 A1 | 7/2002 | Loshak et al. |
| 2002/0167639 A1 | 11/2002 | Coates et al. |
| 2002/0180916 A1 | 12/2002 | Schadt et al. |
| 2003/0008958 A1 | 1/2003 | Momoda et al. |
| 2003/0045612 A1 | 3/2003 | Misura et al. |
| 2003/0189684 A1 | 10/2003 | Kuntz et al. |
| 2004/0046927 A1 | 3/2004 | Montgomery |
| 2004/0068071 A1 | 4/2004 | Hoff et al. |
| 2004/0090570 A1 | 5/2004 | Kosa et al. |
| 2004/0125337 A1 | 7/2004 | Boulineau et al. |
| 2004/0158028 A1 | 8/2004 | Buhler |
| 2004/0185255 A1 | 9/2004 | Walters et al. |
| 2004/0185268 A1 | 9/2004 | Kumar et al. |
| 2004/0186241 A1 | 9/2004 | Gemert |
| 2004/0191520 A1 | 9/2004 | Kumar et al. |
| 2004/0207809 A1 | 10/2004 | Blackburn et al. |
| 2004/0223221 A1 | 11/2004 | Sugimura et al. |
| 2004/0228817 A1 | 11/2004 | Simon et al. |
| 2004/0228818 A1 | 11/2004 | Simon et al. |
| 2005/0003107 A1 | 1/2005 | Kumar et al. |
| 2005/0004361 A1 | 1/2005 | Kumar et al. |
| 2005/0012998 A1 | 1/2005 | Kumar et al. |
| 2005/0146680 A1 | 7/2005 | Muisener et al. |
| 2005/0151926 A1 | 7/2005 | Kumar et al. |
| 2005/0202267 A1 | 9/2005 | Ha et al. |
| 2005/0276767 A1 | 12/2005 | Blin et al. |
| 2006/0022176 A1 | 2/2006 | Wang et al. |
| 2007/0188698 A1 | 8/2007 | Mosse et al. |
| 2009/0309076 A1 | 12/2009 | He et al. |
| 2009/0323011 A1 | 12/2009 | He et al. |

FOREIGN PATENT DOCUMENTS

| | | |
|---|---|---|
| EP | 0321563 A1 | 6/1989 |
| EP | 0331233 A2 | 9/1989 |
| EP | 0336193 A2 | 10/1989 |
| EP | 0397263 A1 | 11/1990 |
| EP | 0442166 A1 | 8/1991 |
| EP | 0446717 A2 | 9/1991 |
| EP | 0488164 A2 | 6/1992 |

| | | |
|---|---|---|
| EP | 0543678 A1 | 5/1993 |
| EP | 0619358 A1 | 10/1994 |
| EP | 0686685 A2 | 12/1995 |
| EP | 0770116 A1 | 5/1997 |
| EP | 0772069 A1 | 5/1997 |
| EP | 0965628 A1 | 12/1999 |
| EP | 1044979 A2 | 10/2000 |
| EP | 1162482 A2 | 12/2001 |
| EP | 1184379 A1 | 3/2002 |
| EP | 1203967 A1 | 5/2002 |
| EP | 1394595 A1 | 3/2004 |
| EP | 1674460 A1 | 6/2006 |
| GB | 583842 | 1/1947 |
| GB | 2169417 A | 7/1986 |
| GB | 2189417 A | 10/1987 |
| JP | 59135428 A | 8/1984 |
| JP | 63175094 A | 7/1988 |
| JP | 63234084 A | 9/1988 |
| JP | 63250381 A | 10/1988 |
| JP | 63250382 A | 10/1988 |
| JP | 63275587 A | 11/1988 |
| JP | 64030744 U | 2/1989 |
| JP | 64090286 | 4/1989 |
| JP | 1170904 A | 7/1989 |
| JP | 01258681 | 10/1989 |
| JP | 280490 A | 3/1990 |
| JP | 2101080 A | 4/1990 |
| JP | 2194084 A | 7/1990 |
| JP | 2243694 A | 9/1990 |
| JP | 03200118 | 2/1991 |
| JP | 03200218 A | 2/1991 |
| JP | 366692 A | 3/1991 |
| JP | 3137634 A | 6/1991 |
| JP | 3221563 A | 9/1991 |
| JP | 3227988 A | 10/1991 |
| JP | 4117387 A | 4/1992 |
| JP | 4358117 A | 12/1992 |
| JP | 6214195 A | 8/1994 |
| JP | 6295687 A | 10/1994 |
| JP | 6306354 A | 11/1994 |
| JP | 741758 A | 2/1995 |
| JP | 762337 A | 3/1995 |
| JP | 7165762 A | 6/1995 |
| JP | 8027155 A | 1/1996 |
| JP | 8027461 A | 1/1996 |
| JP | 8157467 A | 6/1996 |
| JP | 8176139 A | 7/1996 |
| JP | 8209119 A | 8/1996 |
| JP | 8295690 A | 11/1996 |
| JP | 973149 A | 3/1997 |
| JP | 9124645 A | 5/1997 |
| JP | 2001114775 A | 4/2001 |
| JP | 2005112772 A | 4/2005 |
| JP | 2005187420 A | 7/2005 |
| WO | 8905464 A1 | 6/1989 |
| WO | 8911674 A1 | 11/1989 |
| WO | 9201959 A1 | 2/1992 |
| WO | 9310112 A1 | 5/1993 |
| WO | 9317071 A1 | 9/1993 |
| WO | 9601884 A1 | 1/1996 |
| WO | 9705213 A1 | 2/1997 |
| WO | 9706455 A1 | 2/1997 |
| WO | 9710241 A1 | 3/1997 |
| WO | 9722894 A1 | 6/1997 |
| WO | 9819207 A1 | 5/1998 |
| WO | 9920630 A1 | 4/1999 |
| WO | 9943666 A1 | 9/1999 |
| WO | 0015630 A1 | 3/2000 |
| WO | 0019252 A1 | 4/2000 |
| WO | 0035902 A1 | 6/2000 |
| WO | 0077559 A1 | 12/2000 |
| WO | 0102449 A2 | 1/2001 |
| WO | 0119813 A1 | 3/2001 |
| WO | 0155960 A1 | 8/2001 |
| WO | 0170719 A2 | 9/2001 |
| WO | 0177112 A2 | 10/2001 |
| WO | 0229489 A2 | 4/2002 |
| WO | 02058921 A1 | 8/2002 |
| WO | 03019270 A1 | 3/2003 |
| WO | 03032066 A1 | 4/2003 |
| WO | 2004003107 A1 | 1/2004 |
| WO | 2004011964 A1 | 2/2004 |
| WO | 2004041961 A1 | 5/2004 |
| WO | 2005005570 A1 | 1/2005 |
| WO | 2005084826 A1 | 9/2005 |
| WO | 2005085912 A1 | 9/2005 |
| WO | 2010065393 A1 | 6/2010 |

OTHER PUBLICATIONS

Kozenkov, V.M. et al., "Photoanisotropic Effects in Pole (Vinyl-Cinnamate) Derivatives and Their Applications," Mol. Cryst. Liq. Cryst., 2004, pp. 251-267, vol. 409.

Hikmet, R.A.M. et al., "Gel Layer for Inducing Adjustable Pretilt Angles in Liquid Crystal Systems," J. App. Phys. Aug. 1991, pp. 1265-1266, vol. 70, No. 3.

Schadt, Martin et al., "Surface-Induced Parallel Alignment of Liquid Crystals by Linearly Polymerized Photopolymers," Jpn. J. Appl. Phys., Jul. 1992, pp. 2155-2164, vol. 31, No. 7.

Schadt, Martin, "Optics and Applications of Photo-Aligned Liquid Crystalline Surfaces," Nonlinear Optics, 2000, pp. 1-12, vol. 25.

Schadt, Martin, "Liquid Crystal Displays and Novel Optical Thin Films Enabled by Photo-Alignment," Mol. Cryst. Liq. Cryst., 2001, pp. 151-169, vol. 364.

Castellane, Joseph A., "Surface Anchoring of Liquid Crystal Molecules on Various Substrates," Mol. Cryst. Liq. Cryst., 1983, pp. 33-41, vol. 94.

Huang, D.D. et al., "Effect of Aligning Layer Thickness on Photo-Aligned Ferroelectric Liquid Crystal Displays," Proceedings of the 6th Chinese Optoelectronics Symposium, Hong Kong China, IEEE (New York), 2003, pp. 231-234.

Chigrinov, V.G. et al., "New Results on Liquid Crystal Alignment by Photopolymerization," Proceedings of the SPIE-The Internationali Society for Optical Engineering, SPIE, 1995, pp. 130-140, vol. 2409.

"Cholesteric Filters and Films" Rolic Ltd. available at http://www.rolic.com/050application/05223content.htm, 2003, 2 pages.

"Dichroic Linear Polarisers," Rolic Ltd. available at http://www.rolic.com/050applicaiton/05313content.htm, 2003, 1 page.

Bachels, Thomas et al., "Novel Photo-Aligned LC-Polymer Wide View Film for TN Displays," Eurodisplay, 2002, pp. 183-186.

Castellano, Joseph A., "Surface Anchoring of Liquid Crystal Molecules on Various Substrates," Mol. Cryst. Liq. Cryst., 1983, pp. 33-41, vol. 94.

Moia, Franco et al., "Optical LLP/LCP devices: A New Generation of Optical Security Elements," Proceedings of SPIE: Optical Security and Counterfeit Deterrence Techniques III, Jan. 27-28, 2000, pp. 196-203, vol. 3973, San Jose, California.

Moia, Franco, "New Coloured Optical Security Elements Using Rolic's LLP/LCP Technology: Devices for 1st to 3rd Level Inspection," Proceedings of SPIE: Optical Security and Counterfeit Deterrence Techniques IV, Jan. 23-25, 2002, pp. 194-202, vol. 4677, San Jose, California.

Sieberle, Hubert et al., Invited paper: Photo-Aligned Anisotropic Optical Thin Films, SID 03 Digest, Society of Information Displays, 2003, pp. 1162-1165.

Atassi, Yomen et al., "Reversible Photoinduced Modifications of Polymers Doped with Photochromes: Anisotropy, Photo-assisted Poling and Surface Gratings," Mol. Cryst. Liq. Cryst., 1998, pp. 11-22, vol. 315.

"Friedel-Crafts and Related Reactions," George A. Olah, Interscience Publishers, 1964, p. 1, vol. 3, Chapter XXXI (Aromatic Ketone Synthesis).

Ishihara, Yuji et al., "Regioselective Friedel-Crafts Acylation of 1,2,3,4-Tetrahydroquinoline and Related Nitrogen Heterocycles: Effects of NH Protective Groups and Ring Size," J. Chem. Soc. Perkin Trans., 1992, pp. 3401-3406, vol. 1.

Wang, Xiao-Jun et al., "Addition of Grignard Reagents to Aryl Acid Chlorides: An Efficient Synthesis of Aryl Ketones," Organic Letters, 2005, pp. 5593-5595, vol. 7, No. 25.

Hattori Tetsutaro et al., "Practical Synthesis of 4'-Methylbiphenyl-2-carboxylic Acid," Synthesis, Jan. 1995, pp. 41-43.

Hattori, Tetsutaro et al., "Facile Construction of the 1-Phenylnaphthyl Skeleton via an Ester-mediated Nucleophilic Aromatic Substitution Reaction. Applications to the Synthesis of Phenylnaphthalide Lignans," J. Chem. Soc. Perkin Trans., 1995, pp. 235-241, vol. 1.

Furrow, Michael E. et al., Practical Procedures for the Preparation of N-tert-Butyldimethylsilylhydrazones and Their Use in Modified Wolff-Kishner Reductions and in the Synthesis of Vinyl Halides and gem-Dihalides, J. Am. Chem. Soc., 2004, pp. 5436-5445, vol. 126, No. 17.

Ishiyama, Tatsuo, "Palladium (0)-Catalyzed Cross-Coupling Reaction of Alkoxydiboron with Haloarenes: A Direct Procedure for Arylboronic Esters," J. Org. Chem., 1995, pp. 7508-7510, vol. 60, No. 23.

Araujo, R. J. et al., "Photochromism," Techniques in Chemistry, 1971, pp. 734-853, vol. III, Chapter 3, Glenn H. Brown, Editor, Wiley-Interscience a Division of John Wiley & Sons, Inc.

* cited by examiner

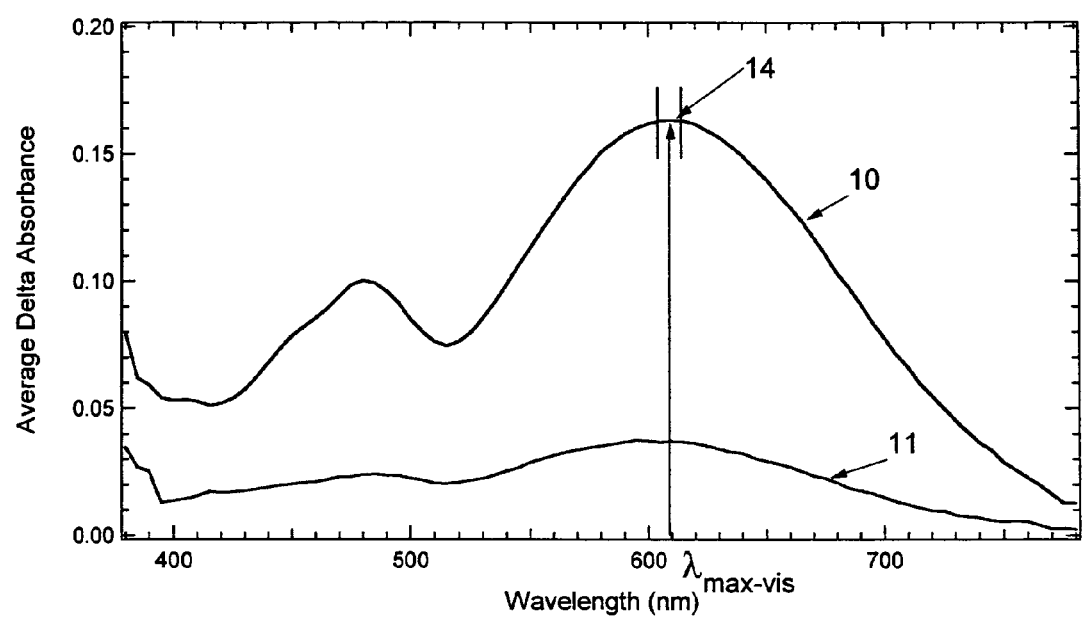

PHOTOCHROMIC COMPOUNDS AND COMPOSITIONS

CROSS-REFERENCE TO RELATED APPLICATIONS

This application is a continuation-in-part of U.S. patent application Ser. No. 12/329,092 filed on Dec. 5, 2008, which is a continuation-in-part of U.S. patent application Ser. No. 10/846,629, filed May 17, 2004, now U.S. Pat. No. 7,342,112, and which in turn claims the benefit of U.S. Provisional Application Ser. No. 60/484,100, filed Jul. 1, 2003, all of which documents are hereby specifically incorporated by reference in their entireties.

STATEMENT REGARDING FEDERALLY SPONSORED RESEARCH OR DEVELOPMENT

Not applicable.

REFERENCE TO A SEQUENCE LISTING

Not applicable.

BACKGROUND

The present invention relates generally to photochromic compounds and to and elements made using the photochromic compounds disclosed herein.

Conventional photochromic compounds have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, conventional photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

Dichroic compounds are compounds that are capable of absorbing one of two orthogonal plane polarized components of transmitted radiation more strongly than the other. Thus, dichroic compounds are capable of linearly polarizing transmitted radiation. As used herein, "linearly polarize" means to confine the vibrations of the electric vector of light waves to one direction or plane. However, although dichroic materials are capable of preferentially absorbing one of two orthogonal plane polarized components of transmitted radiation, if the molecules of the dichroic compound are not suitably positioned or arranged, no net linear polarization of transmitted radiation will be achieved. That is, due to the random positioning of the molecules of the dichroic compound, selective absorption by the individual molecules will cancel each other such that no net or overall linear polarizing effect is achieved. Thus, it is generally necessary to suitably position or arrange the molecules of the dichroic compound within another material in order to form a conventional linear polarizing element, such as a linearly polarizing filter or lens for sunglasses.

In contrast to the dichroic compounds, it is generally not necessary to position or arrange the molecules of conventional photochromic compounds to form a conventional photochromic element. Thus, for example, conventional photochromic elements, such as lenses for photochromic eyewear, can be formed, for example, by spin coating a solution containing a conventional photochromic compound and a "host" material onto the surface of the lens, and suitably curing the resultant coating or layer without arranging the photochromic compound in any particular orientation. Further, even if the molecules of the conventional photochromic compound were suitably positioned or arranged as discussed above with respect to the dichroic compounds, because conventional photochromic compounds do not strongly demonstrate dichroism, elements made therefrom are generally not strongly linearly polarizing.

It would be advantageous to provide photochromic compounds, such as but not limited to thermally reversible photochromic compounds, that can exhibit useful photochromic and/or dichroic properties in at least one state, and that can be used in a variety of applications to impart photochromic and/or dichroic properties.

BRIEF SUMMARY OF THE DISCLOSURE

Described herein are compounds represented by the following graphic Formulas I and IA:

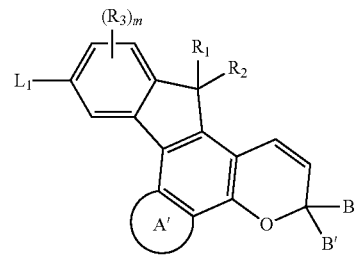

Formula I

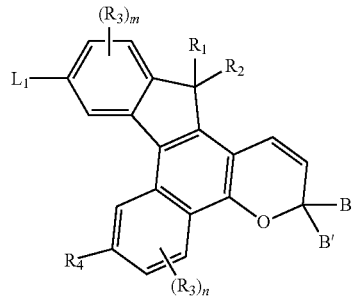

Formula IA wherein:
A' is selected from optionally substituted aryl and optionally substituted heteroaryl; wherein A' is optionally substituted with $L_2$,
$R_1$ and $R_2$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_1$ and $R_2$ may be taken together with any intervening atoms to form a group selected from oxo, optionally substituted cycloalkyl, and optionally substituted heterocycloalkyl; and $R_3$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino;

$R_4$ is selected from hydrogen, $R_3$ and $L_2$;

m and n are each independently an integer selected from 0 to 3;

B and B' are each independently selected from $L_3$, hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl; and $L_1$, $L_2$, and $L_3$ for each occurrence, are independently selected from a chiral or achiral lengthening group represented by:

—$[S_1]_c$-$[Q_1$-$[S_2]_d]_{d'}$-$[Q_2$-$[S_3]_e]_{e'}$-$[Q_3$ -$[S_4]_f]_{f'}$—$S_5$—P wherein:

(a) $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl;

wherein substituents are independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;

wherein said straight-chain $C_1$-$C_{18}$ alkyl and branched $C_1$-$C_{18}$ alkyl are mono-substituted with a group selected from cyano, halogen, and $C_1$-$C_{18}$ alkoxy; or wherein said straight-chain $C_1$-$C_{18}$, alkyl and branched $C_1$-$C_{18}$ alkyl are poly-substituted with at least two groups independently selected from halogen, -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;

(b) c, d, e, and f are each independently chosen from an integer from 1 to 20; and each $S_1$, $S_2$, $S_3$, $S_4$, and $S_5$ is independently chosen for each occurrence from a spacer unit selected from:

(i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl;

(ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl; and (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other, each bond between $S_1$ and the compound represented by graphic Formula I and/or IA is free of two heteroatoms linked together, and the bond between $S_5$ and P is free of two heteroatoms linked to each other;

(c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl ($C_1$-$C_{18}$)alkyl, alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, alkylamino, di-($C_1$-$C_{18}$)alkylamino, alkyl($C_1$-$C_{18}$)alkoxy, alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$) alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor or P is a substituted or unsubstituted photochromic compound; and (d) d', e' and f' are each independently chosen from 0, 1, 2, 3, and 4, provided that a sum of d'+e'+f' is at least 2.

Also provided herein are photochromic compositions and photochromic articles comprising at least one compound of Formulas I and IA.

BRIEF DESCRIPTION OF THE SEVERAL VIEWS OF THE DRAWING(S)

Various non-limiting embodiments of the present disclosure will be better understood when read in conjunction with the drawings, in which:

FIG. 1 shows two average difference absorption spectrum obtained for a photochromic compound according to various non-limiting embodiments disclosed herein using the CELL METHOD.

DETAILED DESCRIPTION

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 20 carbon atoms, in certain embodiments, from 1 to 10 carbon atoms, in certain embodiments, from 1 to 8 or 1 to 6 carbon atoms, and in certain embodiments from 1 to 3 carbon atoms.

"Acyl" by itself or as part of another substituent refers to a radical —C(O)R$^{30}$, where R$^{30}$ is hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of acyl groups include, but are not limited to, formyl, acetyl, cyclohexylcarbonyl, cyclohexylmethylcarbonyl, benzoyl, benzylcarbonyl, and the like.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 18 carbon atoms. Examples of alkoxy groups include, but are not limited to, methoxy, ethoxy, propoxy, butoxy, cyclohexyloxy, and the like.

"Alkoxycarbonyl" by itself or as part of another substituent refers to a radical —C(O)OR$^{31}$ where R$^{31}$ is alkyl, cycloalkyl, cycloalkylalkyl, aryl, or arylalkyl, which can be substituted, as defined herein.

"Amino" refers to the radical —NH$_2$.

"Aminocarbonyl" by itself or as part of another substituent refers to radical of the formula —N(R$^{60}$)C(O)R$^{60}$ where each R$^{60}$ is independently selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl "Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is C$_{7-30}$ arylalkyl, e.g., the alkanyl, alkenyl, or alkynyl moiety of the arylalkyl group is C$_{1-10}$ and the aryl moiety is C$_{6-20}$, and in certain embodiments, an arylalkyl group is C$_{7-20}$ arylalkyl, e.g., the alkanyl, alkenyl, or alkynyl moiety of the arylalkyl group is C$_{1-8}$ and the aryl moiety is C$_{6-12}$.

"Carboxamidyl" by itself or as part of another substituent refers to a radical of the formula —C(O)NR$^{60}$R$^{61}$ where each R$^{60}$ and R$^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring.

"Compounds" refers to compounds encompassed by structural Formulas I and IA herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formulas I and IA include, but are not limited to, optical isomers of compounds of Formulas I and IA, racemates thereof, and other mixtures thereof. In such embodiments, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. However, unless otherwise stated, it should be assumed that Formulas I and IA cover all asymmetric variants of the compounds described herein, including isomers, racemates, enantiomers, diastereomers, and other mixtures thereof. In addition, compounds of Formulas I and IA include Z- and E-forms (e.g., cis- and trans-forms) of compounds with double bonds. In embodiments in which compounds of Formulas I and IA exist in various tautomeric forms, compounds provided by the present disclosure include all tautomeric forms of the compound.

The compounds of Formulas I and IA may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms and as N-oxides. In general, compounds may be hydrated, solvated, or N-oxides. Certain compounds may exist in single or multiple crystalline or amorphous forms. In general, all physical forms are equivalent for the uses contemplated herein and are intended to be within the scope provided by the present disclosure. Further, when partial structures of the compounds are illustrated, an asterisk (*) indicates the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroalkyl" by itself or as part of another substituent refer to an alkyl group in which one or more of the carbon atoms (and any associated hydrogen atoms) are independently replaced with the same or different heteroatomic groups. In some embodiments, heteroalkyl groups have from 1 to 8 carbon atoms. Examples of heteroatomic groups include, but are not limited to, —O—, —S—, —S—S—, —NR$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{38}$, R$^{39}$, R$^{40}$, R$^{41}$, R$^{42}$, R$^{43}$, and R$^{44}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroalkyl, substituted heteroalkyl, heteroaryl, substituted heteroaryl, heteroarylalkyl, or substituted heteroarylalkyl. Where a specific level of saturation is intended, the nomenclature "heteroalkanyl," "heteroalkenyl," or "heteroalkynyl" is used. In certain embodiments, R$^{38}$, R$^{39}$, R$^{40}$, R$^{41}$, R$^{42}$, R$^{43}$, and R$^{44}$ are independently chosen from hydrogen and $C_{1-3}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Leaving group" refers to an atom or a group capable of being displaced by a nucleophile and includes halogen, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, p-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Perhaloalkyl" is a subset of substituted alkyl wherein each hydrogen atom is replaced with the same or different halogen atom. Examples of perhaloalkyl includes, but is not limited to, —$CF_3$, —$CF_2CF_3$, and —$C(CF_3)_3$.

"Perhaloalkoxy" is a subset of substituted alkoxy wherein each hydrogen atom of $R^{31}$ is replaced with the same or different halogen atom. Examples of perhaloalkoxy includes, but is not limited to, —$OCF_3$, —$OCF_2CF_3$, and —$OC(CF_3)_3$.

"Protecting group" refers to a grouping of atoms, which when attached to a reactive group in a molecule masks, reduces, or prevents that reactivity. Examples of protecting groups can be found in Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Silyl" by itself or as part of another substituent refers to a radical of the formula —$SiR^{30}R^{31}R^{31}$ where each of $R^{30}$, $R^{31}$, and $R^{31}$ is independently selected from alkyl, alkoxyl, and phenyl, which can each be substituted, as defined herein.

"Siloxy" by itself or as part of another substituent refers to a radical of the formula —$OSiR^{30}R^{31}R^{31}$ where each of $R^{30}$, $R^{31}$, and $R^{31}$ is independently selected from alkyl, alkoxyl, and phenyl, which can each be substituted, as defined herein.

"Substituted" refers to a group in which one or more hydrogen atoms are independently replaced with the same or different substituent(s). Examples of substituents include, but are not limited to, —$R^{64}$, —$R^{60}$, —$O^-$, (—OH), =O, —$OR^{60}$, —$SR^{60}$, —$S^-$, =S, —$NR^{60}R^{61}$, =$NR^{60}$, —$CX_3$, —CN, —$CF_3$, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$, —$C(NR^{62})NR^{60}R^{61}$, —$S(O)_2$, $NR^{60})R^{61}$, —$N^{63}S(O)_2R^{60}$, —$NR^{63}C(O)R^{60}$, and —$S(O)R^{60}$ where each —$R^{64}$ is independently a halogen; each $R^{60}$ and $R^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings. In certain embodiments, a tertiary amine or aromatic nitrogen may be substituted with one or more oxygen atoms to form the corresponding nitrogen oxide.

"Sulfonate" by itself or as part of another substituent refers to a sulfur radical of the formula —$S(O)_2O^-$.

"Sulfonyl" by itself or as part of another substituent refers to a sulfur radical of the formula —$S(O)_2R^{60}$ where $R^{60}$ may be selected from hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, and substituted heteroarylalkyl.

In certain embodiments, substituted aryl and substituted heteroaryl include one or more of the following substitute groups: F, Cl, Br, I, $C_{1-3}$ alkyl, substituted alkyl, $C_{1-3}$ alkoxy, —$S(O)_2NR^{50}R^{51}$, —$NR^{50}R^{51}$, —$CF_3$, —$OCF_3$, —CN, —$NR^{50}S(O)_2R^{51}$, —$NR^{50}C(O)R^{51}$, $C_{5-10}$ aryl, substituted $C_{5-10}$ aryl, $C_{5-10}$ heteroaryl, substituted $C_{5-10}$ heteroaryl, —$C(O)OR^{50}$, —$NO_2$, —$C(O)R^{50}$, —$C(O)NR^{50}R^{51}$, —$OCHF_2$, $C_{1-3}$ acyl, —$SR^{50}$, —$S(O)_2OH$, —$S(O)_2R^{50}$, —$S(O)R^{50}$, —$C(S)R^{50}$, —$C(O)O^-$, —$C(S)OR^{50}$, —$NR^{50}C(O)NR^{51}R^{52}$, —$NR^{50}C(S)NR^{51}R^{52}$, and —$C(NR^{50})NR^{51}R^{52}$, $C_{3-8}$cycloalkyl, and substituted $C_{3-8}$ cycloalkyl, wherein $R^{50}$, $R^{51}$, and $R^{52}$ are each independently selected from hydrogen and $C_1$-$C_4$ alkyl.

As used in this specification and the appended claims, the articles "a," "an," and "the" include plural referents unless expressly and unequivocally limited to one referent.

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

The phrase "an at least partial coating" means an amount of coating covering from a portion to the complete surface of the substrate. The phrase "an at least partially cured coating" refers to a coating in which the curable or crosslinkable components are at least partially cured, crosslinked and/or reacted. In alternate non-limiting embodiments, the degree of reacted components, can vary widely, e.g., from 5% to 100% of all the possible curable, crosslinkable and/or reactable components.

The phrase "an at least partially abrasion resistant coating or film" refers to a coating or film that demonstrates a Bayer Abrasion Resistance Index of from at least 1.3 to 10.0 in ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the untreated surface. Put another way, the percent transmittance of the treated surface can range from a percentage greater than the untreated surface up to 99.9.

Various non-limiting embodiments of the disclosure will now be described. One non-limiting embodiment provides a thermally reversible, photochromic compound comprising a Lengthening group L also described hereinafter. Another non-limiting embodiment provides a photochromic compound adapted to have at least a first state and a second state, wherein the thermally reversible, photochromic compound has an average absorption ratio greater than 1.5 in at least one state as determined according to the CELL METHOD, which is described in detail below. Further, according to various non-limiting embodiments, the thermally reversible, photochromic compound has an average absorption ratio greater than 1.5 in an activated state as determined according to the CELL METHOD. As used herein with respect to photochromic compounds, the term "activated state" refers to the photochromic compound when exposed to sufficient actinic radiation to cause the at least a portion of the photochromic compound to switch states.

Generally speaking, the CELL METHOD of measuring average absorption ratio of a photochromic compound involves obtaining an absorption spectrum for the photochromic compound, in an activated or unactived state, in each of two orthogonal polarization directions while the photochromic compound is at least partially aligned in an aligned liquid crystal medium that is contained within a cell assembly. More specifically, the cell assembly comprises two opposing glass substrates that are spaced apart by 20 microns +/−1 micron. The substrates are sealed along two opposite edges to form the cell. The inner surface of each of the glass substrates is coated with a polyimide coating, the surface of which has been at least partially ordered by rubbing. Alignment of the photochromic compound is achieved by introducing the photochromic compound and a liquid crystal medium into the cell assembly and allowing the liquid crystal medium to align with the rubbed polyimide surface. Because the photochromic compound is contained within the liquid crystal medium, alignment of the liquid crystal medium causes the photochromic compound to be aligned. It will be appreciated by those skilled in the art that the choice of the liquid crystal medium and the temperature used during testing can affect the measured absorption ratio. Accordingly, as set forth in more detail in the Examples, for purposes of the CELL METHOD, absorption ratio measurements are taken at room temperature (73° F. +/−0.5° F. or better) and the liquid crystal medium is Licristal® E7 (which is reported to be a mixture of cyanobiphenyl and cyanoterphenyl liquid crystal compounds).

Once the liquid crystal medium and the photochromic compound are aligned, the cell assembly is placed on an optical bench (which is described in more detail in the Examples). To obtain the average absorption ratio in the activated state, activation of the photochromic compound is achieved by exposing the photochromic compound to UV radiation for a time sufficient to reach a saturated or near saturated state (that is, a state wherein the absorption properties of the photochromic compound do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the cell is measured at each time interval for all of the wavelengths tested and the unactivated absorbance (i.e., the absorbance of the cell with the liquid crystal material and the unactivated photochromic compound) over the same range of wavelengths is subtracted to obtain absorption spectra for the photochromic compound in each of the 0° and 90° polarization planes to obtain an average difference absorption spectrum in each polarization plane for the photochromic compound in the saturated or near-saturated state.

For example, with reference to FIG. 1, there is shown the average difference absorption spectrum (generally indicated 10) in one polarization plane that was obtained for a photochromic compound according to one non-limiting embodiment disclosed herein. The average absorption spectrum (generally indicated 11) is the average difference absorption spectrum obtained for the same photochromic compound in the orthogonal polarization plane.

Based on the average difference absorption spectra obtained for the photochromic compound, the average absorption ratio for the photochromic compound is obtained as follows: The absorption ratio of the photochromic compound at each wavelength in a predetermined range of wavelengths corresponding to $\lambda_{max-vis}$ +/−5 nanometers (generally indicated as 14 in FIG. 1), wherein $\lambda_{max-vis}$ is the wavelength at which the photochromic compound had the highest average absorbance in any plane, is calculated according to the following equation:

$$AR_{\lambda i} = Ab^1_{\lambda i} / Ab^2_{\lambda i} \qquad \text{Eq. 1}$$

wherein, $AR_{\lambda i}$ is the absorption ratio at wavelength $\lambda i$, $Ab^1_{\lambda i}$ is the average absorption at wavelength $\lambda i$ in the polarization direction (i.e., 0° or 90°) having the higher absorbance, and $Ab^2_{\lambda i}$ is the average absorption at wavelength $\lambda i$ in the remaining polarization direction. As previously discussed, the "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average absorption ratio ("AR") for the photochromic compound is then calculated by averaging the individual absorption ratios obtained for the wavelengths within the predetermined range of wavelengths (i.e., $\lambda_{max-vis}$ +/−5 nanometers) according to the following equation:

$$AR = (\Sigma AR_{\lambda i}) / n_i \qquad \text{Eq. 2}$$

wherein, AR is average absorption ratio for the photochromic compound, $AR_{\lambda i}$ are the individual absorption ratios (as determined above in Eq. 1) for each wavelength within the predetermined the range of wavelengths (i.e., $\lambda_{max-vis}$ +/−5 nanometers), and $n_i$ is the number of individual absorption ratios averaged.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. However, as previously discussed, generally conventional thermally reversible photochromic compounds do not strongly demonstrate dichroism.

As discussed above, non-limiting embodiments disclosed herein provide a thermally reversible photochromic compound having an average absorption ratio greater than 1.5 in at least one state as determined according to CELL METHOD and/or a thermally reversible photochromic compound that can be used as an intermediate in the preparation of a photochromic compound having an absorption ratio greater than 1.5. Thus, the thermally reversible photochromic compound according to this non-limiting embodiment can display useful photochromic properties and/or useful photochromic and dichroic properties. That is, the thermally reversible, photochromic compound can be a thermally reversible, photochromic and/or photochromic-dichroic compound. As used herein with respect to the photochromic compounds described herein, the term "photochromic-dichroic" means displaying both photochromic and dichroic properties under certain conditions, which properties are at least detectable by instrumentation.

According to other non-limiting embodiments, the thermally reversible photochromic compounds can be thermally reversible photochromic-dichroic compounds having an average absorption ratio ranging from 4 to 20, from 3 to 30, or from 2.0 to 50 in at least one state as determined according to CELL METHOD. It will be appreciated by those skilled in the art that the higher the average absorption ratio of the photochromic compound the more linearly polarizing the photochromic compound will be. Therefore, according to various non-limiting embodiments, the thermally reversible photochromic compounds can have any average absorption ratio required to achieve a desired level of linear polarization.

In some embodiments, the compounds described herein may be photochromic and/or dichroic compounds, and may be represented by the following graphic Formula I, wherein the definitions of the substituents have the same meaning as described herein unless otherwise stated:

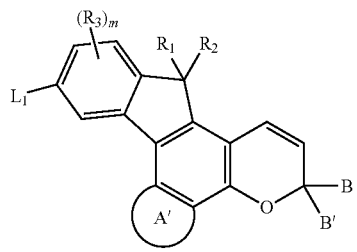

Formula I wherein A' represents an optionally substituted aryl or optionally substituted heteroaryl. With reference to Formula I, A' may comprise any of the "aryl" or "heteroaryl" groups previously defined above, including monocyclic and multicyclic groups. Further, A' may be unsubstituted, monosubstituted, or multisubstituted, wherein each substituent is independently selected from the groups as previously defined above for the term "substituted." Also, the optional substitutents may be independently selected from the groups defined below for $R_3$ and $R_4$ in Formula IA. Additionally, A' may be substituted with 0-10 groups, for example, A' may be substituted with 0-8 groups, or A' may be substituted with 0-6 groups, or A' may be substituted with 0-4 groups or A' may be substituted with 0-3 groups.

The compounds described herein may be represented by the following graphic formula, in which the numbers represent the numbers of the ring atoms of the naphthopyran and in the definitions of the substituents have the same meaning described herein unless stated otherwise:

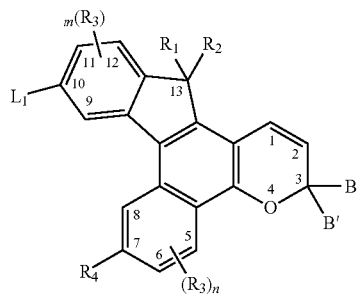

More specifically, the compounds described herein are represented by the following graphic Formula IA:

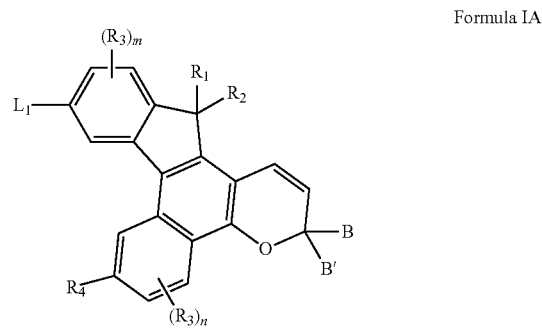

Formula IA wherein:

$R_1$ and $R_2$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_1$ and $R_2$ may be taken together with any intervening atoms to form a group selected from oxo, optionally substituted cycloalkyl, and optionally substituted heterocycloalkyl;

$R_3$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino;

$R_4$ is selected from hydrogen, $R_3$ and $L_2$;

m and n are each independently an integer selected from 0 to 3;

B and B' are each independently selected from $L_3$, hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl; and $L_1$, $L_2$, and $L_3$ for each occurrence, are independently selected from a chiral or achiral lengthening group represented by:

—[S$_1$]$_c$-[Q$_1$-[S$_2$]$_d$]$_{d'}$-[Q$_2$-[S$_3$]$_e$]$_{e'}$-[Q$_3$-[4]$_f$]$_{f'}$—S$_5$—P wherein:

(a) $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl;

wherein substituents are independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$) alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, (perfluoro($C_1$-$C_{18}$)alkyl)amino, perfluoro($C_1$-$C_{18}$)alkylthio, $C_1$-$C_{18}$ alkylthio, $C_1$-$C_{10}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;

wherein said straight-chain $C_1$-$C_{18}$ alkyl and branched $C_1$-$C_{18}$ alkyl are mono-substituted with a group selected from cyano, halogen, and $C_1$-$C_{18}$ alkoxy; or wherein said straight-chain $C_1$-$C_{18}$ alkyl and branched $C_1$-$C_{18}$ alkyl are poly-substituted with at least two groups independently selected from halogen, -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;

(b) c, d, e, and f are each independently chosen from an integer from 1 to 20; and each $S_1$, $S_2$, $S_3$, $S_4$, and $S_5$ is independently chosen for each occurrence from a spacer unit selected from:

(i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl;

(ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl; and (iii) —O—, —C(=O)—, —=C—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms of the first spacer unit are not directly linked to the heteroatoms of the second spacer unit, and provided that when $S_1$ and $S_5$ are linked to Formula I and P, respectively, they are linked so that two heteroatoms are not directly linked to each other;

(c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl ($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$) alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl ($C_1$-$C_{18}$)alkoxy($C_1$-$C_{18}$)alkyl, polyethyleneoxy, polypropyleneoxy, ethylene, acryloyl, acryloyloxy($C_1$-$C_{18}$) alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor or P is a substituted or unsubstituted photochromic compound; and (d) d', e' and f' are each independently chosen from 0, 1, 2, 3, and 4, provided that a sum of d'+e'+f' is at least 2.

With reference to Formula IA, $R_1$ and $R_2$ each independently can be selected from hydrogen, hydroxy, and chiral and achiral groups selected from optionally substituted heteroalkyl, optionally substituted alkyl, optionally substituted aryl, optionally substituted heteroaryl, optionally substituted cycloalkylhalogen, optionally substituted amino, carboxy, alkylcarbonyl, alkoxycarbonyl, optionally substituted alkoxy, and aminocarbonyl or $R_1$ and $R_2$ may be taken together with any intervening atoms to form a group selected from oxo, optionally substituted cycloalkyl and optionally substituted heterocycloalkyl;

$R_3$ for each occurrence, independently can be selected from formyl, alkylcarbonyl, alkoxycarbonyl, aminocarbonyl, arylcarbonyl, aryloxycarbonyl, optionally substituted alkyl, boronic acid ester, halogen, optionally substituted cycloalkyl, optionally substituted aryl, optionally substituted alkoxy, optionally substituted heteroalkyl, optionally substituted heterocycloalkyl and optionally substituted amino;

m and n each independently can be an integer selected from 0 to 2;

B and B' each independently can be selected from $L_3$, hydrogen, halogen, chiral or achiral groups selected from optionally substituted alkyl, optionally substituted alkenyl, optionally substituted heteroalkyl, optionally substituted alkoxy, optionally substituted aryl, optionally substituted heteroaryl, and optionally substituted cycloalkyl, or wherein B and B' are taken together with any intervening atoms to form a group selected from optionally substituted cycloalkyl and optionally substituted heterocycloalkyl;

$L_1$, $L_2$, and $L_3$ for each occurrence, independently can be selected from a chiral or achiral lengthening group represented by:

—[$S_1$]$_c$-[$Q_1$-[$S_2$]$_d$]$_{d'}$-[$Q_2$-[$S_3$]$_e$]$_{e'}$-[$Q_3$-[$S_4$]$_f$]$_{f'}$—$S_5$—P wherein:

(a) $Q_1$, $Q_2$, and $Q_3$ for each occurrence, are independently selected from a divalent group selected from optionally substituted aryl and optionally substituted heteroaryl, optionally substituted cycloalkyl and optionally optionally substituted heterocycloalkyl;

wherein substituents are independently selected from P, liquid crystal mesogens, halogen, poly($C_1$-$C_{12}$ alkoxy), $C_1$-$C_{12}$ alkoxycarbonyl, $C_1$-$C_{12}$ alkylcarbonyl, perfluoro($C_1$-$C_{12}$) alkoxy, perfluoro($C_1$-$C_{12}$)alkoxycarbonyl, perfluoro($C_1$-$C_{12}$)alkylcarbonyl, $C_1$-$C_{18}$ acetyl, $C_3$-$C_7$ cycloalkyl, $C_3$-$C_7$ cycloalkoxy, straight-chain $C_1$-$C_{12}$ alkyl, and branched $C_1$-$C_{12}$ alkyl, wherein said straight-chain $C_1$-$C_{12}$ alkyl and branched $C_1$-$C_{12}$ alkyl are mono-substituted with a group selected from, halogen, $C_1$-$C_{12}$ alkoxy, or wherein said straight-chain $C_1$-$C_{12}$ alkyl and branched $C_1$-$C_{12}$ alkyl are poly-substituted with at least two groups independently selected from halogen;

(b) c, d, e, and f are each independently chosen from an integer from 1 to 10; and each $S_1$, $S_2$, $S_3$, $S_4$, and $S_5$ is independently chosen for each occurrence from a spacer unit selected from:

(i) substituted or unsubstituted alkylene, substituted or unsubstituted haloalkylene, —Si(CH$_2$)$_g$—, and —(Si[(CH$_3$)$_2$]O)$_h$—, wherein g for each occurrence is independently chosen from an integer from 1 to 10; h for each occurrence is independently chosen from an integer from 1 to 8; and said substitutes for the alkylene and haloalkylene are independently selected from $C_1$-$C_{12}$ alkyl, $C_3$-$C_7$ cycloalkyl and phenyl;

(ii) —N(Z)—, —C(Z)=C(Z)—, and a single bond, wherein Z for each occurrence is independently selected from hydrogen, $C_1$-$C_{12}$ alkyl, $C_3$-$C_7$ cycloalkyl and phenyl; and (iii) —O—, —C(=O)—, —N=N—, —S—, and —S(=O)—, provided that when two spacer units comprising heteroatoms are linked together the spacer units are linked so that heteroatoms of the first spacer unit are not directly linked to the heteroatoms of the second spacer unit, and provided that when $S_1$ and $S_5$ are linked to Formula I and P, respectively, they are linked so that two heteroatoms are not directly linked to each other;

(c) P for each occurrence is independently selected from hydroxy, amino, $C_2$-$C_{12}$ alkenyl, $C_2$-$C_{12}$ alkenyl, silyl, siloxy, (tetrahydro-2H-pyran-2-yl)oxy, isocyanato, acryloyloxy, methacryloyloxy, epoxy, carboxylic acid, carboxylic ester, $C_1$-$C_{12}$ alkyloxycarbonyloxy, halocarbonyl, hydrogen, aryl, hydroxy($C_1$-$C_{12}$)alkyl, $C_1$-$C_{12}$ alkyl, $C_1$-$C_{12}$ alkoxy, ethylene, acryloyl, acryloyloxy($C_1$-$C_{12}$)alkyl, methacryloyl, methacryloyloxy($C_1$-$C_{12}$)alkyl, oxetanyl, glycidyl, vinyl ether, siloxane derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, wherein each substituent is independently chosen from $C_1$-$C_{12}$ alkyl, $C_1$-$C_{12}$ alkoxy, amino, $C_3$-$C_7$ cycloalkyl, $C_1$-$C_{12}$ alkyl($C_1$-$C_{12}$)alkoxy, or fluoro($C_1$-$C_{12}$)alkyl, or P is a structure having from 2 to 4 reactive groups; and (d) d', e' and f' are each independently chosen from 0, 1, 2, 3, and 4, provided that a sum of d'+e'+f' is at least 2.

Additionally, $R_1$ and $R_2$ are each independently can be selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or $R_1$ and $R_2$ may be taken together with any intervening atoms to form a group selected from oxo and optionally substituted cycloalkyl;

$R_3$ for each occurrence, independently can be selected from alkylcarbonyl, alkoxycarbonyl, aminocarbonyl, optionally substituted alkyl, boronic acid ester, halogen, optionally substituted cycloalkyl, optionally substituted aryl, optionally substituted alkoxy, optionally substituted heterocycloalkyl and optionally substituted amino;

where m and n are each independently an integer selected from 0 to 2;

B and B' are each independently selected from $L_3$, hydrogen, chiral groups selected from optionally substituted alkyl, optionally substituted alkenyl, optionally substituted aryl, optionally substituted heteroaryl, and optionally substituted cycloalkyl, or wherein B and B' are taken together with any intervening atoms to form a group selected from optionally substituted cycloalkyl;

$L_1$, $L_2$, and $L_3$ for each occurrence, are independently selected from a chiral or achiral lengthening group represented by:

—[S$_1$]$_c$-[Q$_1$-[S$_2$]$_d$]$_{d'}$-[Q$_2$-[S$_3$]$_e$]$_{e'}$-[Q$_3$-[S$_4$]$_f$]$_{f'}$—S$_5$—P wherein:

(a) $Q_1$, $Q_2$, and $Q_3$ for each occurrence, are independently selected from a divalent group selected from optionally substituted aryl and optionally substituted heteroaryl, optionally substituted cycloalkyl and optionally optionally substituted heterocycloalkyl;

wherein substituents are independently selected from P, $C_1$-$C_6$alkoxycarbonyl, perfluoro($C_1$-$C_6$)alkoxy, $C_3$-$C_7$ cycloalkyl, $C_3$-$C_7$ cycloalkoxy, straight-chain $C_1$-$C_6$ alkyl, and branched $C_1$-$C_6$ alkyl, wherein said straight-chain $C_1$-$C_6$alkyl and branched $C_1$-$C_6$ alkyl are mono-substituted with a group selected from halogen and $C_1$-$C_{12}$ alkoxy, or wherein said straight-chain $C_1$-$C_6$ alkyl and branched $C_1$-$C_6$ alkyl are poly-substituted with at least two groups independently selected from halogen;

(b) c, d, e, and f are each independently chosen from an integer from 1 to 10; and each $S_1$, $S_2$, $S_3$, $S_4$, and $S_5$ is independently chosen for each occurrence from a spacer unit selected from:

(i) substituted or unsubstituted alkylene;

(ii) —N(Z)—, —C(Z)=C(Z)—, and a single bond, wherein Z for each occurrence is independently selected from hydrogen and $C_1$-$C_6$ alkyl; and (iii) —O—, —C(=O)—, and —N=N—, —S—;

provided that when two spacer units comprising heteroatoms are linked together the spacer units are linked so that heteroatoms of the first spacer unit are not directly linked to the heteroatoms of the second spacer unit, and provided that when $S_1$ and $S_5$ are linked to Formula I and P, respectively, they are linked so that two heteroatoms are not directly linked to each other;

(c) P for each occurrence is independently selected from hydroxy, amino, $C_2$-$C_6$ alkenyl, $C_2$-$C_6$ alkenyl, siloxy, (tetrahydro-2H-pyran-2-yl)oxy, isocyanato, acryloyloxy, methacryloyloxy, epoxy, carboxylic acid, carboxylic ester, $C_1$-$C_6$ alkyloxycarbonyloxy, hydrogen, aryl, hydroxy($C_1$-$C_6$)alkyl, $C_1$-$C_6$ alkyl, ethylene, acryloyl, acryloyloxy($C_1$-$C_{12}$)alkyl, oxetanyl, glycidyl, vinyl ether, siloxane derivatives, and substituted or unsubstituted chiral or non-chiral monovalent or divalent groups chosen from steroid radicals, wherein each substituent is independently chosen from $C_1$-$C_6$ alkyl, $C_1$-$C_6$ alkoxy, amino, $C_3$-$C_7$ cycloalkyl.

More specifically, $R_1$ and $R_2$ are each independently can be selected from methyl, ethyl, propyl and butyl; $R_3$ and $R_4$ for each occurrence are independently can be selected from methyl, ethyl, bromo, chloro, fluoro, iodo, methoxy, ethoxy and $CF_3$; B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbony; and for $L_1$: $Q_1$ is unsubstituted aryl;

e' is 1 or 2; e each occurrence is 1; $S_3$ for each occurrence is a single bond; $Q_2$ for each occurrence is independently selected from optionally substituted aryl; f' is 1; f is 1; $S_4$ is a single bond; and $Q_3$ is optionally substituted cycloalkyl; $S_5$ is —$(CH_2)_g$—, wherein g is an integer from 1 to 20; and P is hydrogen.

Typically, $R_1$ and $R_2$ are methyl; $R_3$ and $R_4$ for each occurrence are independently selected from methyl, bromo, chloro, fluoro, methoxy, and $CF_3$; B and B' are each independently selected from phenyl substituted with one group selected from $C_1$-$C_4$ alkoxy, fluoro, $CF_3$, piperidinyl, and morpholino; and for $L_1$:$Q_1$ is unsubstituted phenyl; $Q_2$ for each occurrence is unsubstituted phenyl; $Q_3$ is unsubstituted cyclohexyl; and g is 5.

In the compounds of the present invention, $L_1$ can be selected from:

4-[4-(4-butyl-cyclohexyl)-phenyl]-cyclohexyloxy;
4'''-butyl-[1,1',4',1'']tercyclohexane-4-yloxy;
4-[4-(4-butyl-phenyl)cyclohexyloxycarbonyl]-phenoxy;
4'-(4-butyl-benzoyloxy)-biphenyl-4-carbonyloxy;
4-(4-pentyl-phenylazo)-phenylcarbamoyl;
4-(4-dimethylamino-phenylazo)-phenylcarbamoyl;
4-[5-(4-propyl-benzoyloxy)-pyrimidin-2-yl]-phenyl
4-[2-(4'-methyl-biphenyl-4-carbonyloxy)-1,2-diphenyl-ethoxycarbonyl]-phenyl;
4-(1,2-diphenyl-2-{3-[4-(4-propyl-benzoyloxy)-phenyl]-acryloyloxy}-ethoxycarbonyl)-phenyl;
4-[4-(4-{4-[3-(6-{4-[4-(4-nonyl-benzoyloxy)-phenoxycarbonyl]-phenoxy}-hexyloxycarbonyl)propionyloxy]-benzoyloxy}-benzoyloxyyphenyl]-piperazin-1-yl;
4-[4-(4-{4-[4-(4-nonyl-benzoyloxy)-benzoyloxy]-benzoyloxy}-benzoyloxy)-phenyl]-piperazin-1-yl;
4-(4'-propyl-biphenyl-4-ylethynyl)-phenyl;
4-(4-fluoro-phenoxycarbonyloxy)-piperidin-1-yl;
2-[17-(1,5-dimethyl-hexyl)-10,13-dimethyl-2,3,4,7,8,9,10, 11, 12,13,14,15,16,17-tetradecahydro-1H-cyclopenta[a]phenanthren-3-yloxy]-indan-5-yl;
4-[17-(1,5-dimethyl-hexyl)-10,13-dimethyl-2,3,4,7,8,9,10, 11, 12,13,14,15,16,17-tetradecahydro-1H-cyclopenta[a]phenanthren-3-yloxycarbonyloxy]-piperidin-1-yl;
4-(biphenyl-4-carbonyloxy)-piperidin-1-yl;
4-(naphthalene-2-carbonyloxy)-piperidin-1-yl;
4-(4-phenylcarbamoyl-phenylcarbamoyl)-piperidin-1-yl;
4-(4-(4-phenylpiperidin-1-yl)-benzoyloxy)-piperidin-1-yl;
4-butyl-[1,1';4',1'']terphenyl-4-yl;
4-(pentadecafluoroheptyloxy-phenylcarbamoyl)-benzyloxy;
4-(3-piperidin-4-yl-propyl)-piperidin-1-yl;
4-(4-{-4-[17-(1,5-dimethyl-hexyl)-10,13-dimethyl-2,3,4,7, 8,9,10,11,12,13,14,15,16,17-tetradecahydro-1H-cyclopenta[a]phenanthren-3-yloxycarbonyloxy]-benzoyloxy}-phenoxycarbonyl)phenoxymethyl;
4-[4-(4-cyclohexyl-phenylcarbamoyl)-benzyloxy]-piperidin-1-yl;
4-[4-(4-cyclohexyl-phenylcarbamoyl)-benzoyloxy]-piperidin-1-yl;
N-{4-[((4-pentyl-benzylidene)-amino]-phenyl}-acetamidyl;
4-(3-piperidin-4-yl-propyl)piperidin-1-yl;
4-(4-hexyloxy-benzoyloxy)-piperidin-1-yl;
4-(4'-hexyloxy-biphenyl-4-carbonyloxy)-piperidin-1-yl;
4-(4-butyl-phenylcarbamoyl)-piperidin-1-yl;
4-[4-[4-[4-piperidinyl-4-oxy]-phenyl]phenoxy]piperidin-4-yl;
4-(4-(9-(4-butylphenyl)-2,4,8,10-tetraoxaspiro[5.5]undec-3-yl)phenyl)piperazin-1-yl;
4-(6-(4-butylphenyl)carbonyloxy-(4,8-dioxabicyclo[3.3.0]oct-2-yl))oxycarbonyl)phenyl;
1-{4-[5-(4-butyl-phenyl)-[1,3]dioxan-2-A-phenyl}-4-methyl-piperazin-1-yl;
4-(7-(4-propylphenylcarbonyloxy)bicyclo[3.3.0]oct-2-yl) oxycarbonyl)phenyl;
4-[17-(1,5-dimethyl-hexyl)-10,13-dimethyl-2,3,4,7,8,9,10, 11, 12,13,14,15,16,17-tetradecahydro-1H-cyclopenta[a]phenanthren-3-yloxycarbonyloxy;
(4-trans-(4-pentylcyclohexyl)benzamido)phenyl;
(4-(4-trans-(4-pentylcyclohexyl)phenoxy)carbonyl)phenyl;
4-(4-(4-trans-(4-pentylcyclohexyl)phenyl)benzamido)phenyl;
4-((trans-(4'-pentyl-[1,1'-bi(cyclohexan)]-4-yl)oxy)carbonyl)phenyl;
4-(4'-(4-pentylcyclohexyl)-[1,1'-biphenyl]-4-ylcarboxamido)phenyl;
4-((4(4'-(4-pentylcyclohexyl)-[1,1-biphenyl]-4-carbonyl) oxy)benzamido;
4-(4'-(4-pentylcyclohexyl)-[1,1'-biphenyl]-4-carbonyl)piperazin-1-yl;
4-(4-(4-trans-(4-pentylcyclohexyl)phenyl)benzamido)-2-(trifluoromethyl)phenyl;
2-methyl-4-trans-(4((4'-trans-(4-pentylcyclohexyl)biphenyl-4-yloxy)carbonyl)cyclohexanecarboxamido)phenyl;
4'-(4'-pentylbi(cyclohexane-4-)carbonyloxy)biphenylcarbonyloxy;
4-(((3S,8S,9S,10R,13R,14S,17R)-10,13-dimethyl-17-(R)-6-methylheptan-2-yl)-2,3,4,7,8,9,10,11,12,13,14,15,16, 17-tetradecahydro-1H-cyclopenta[a]phenanthren-3-yloxy)carbonyl)piperazin-1-yl; and
4-((S)-2-methylbutoxy)phenyl)-10-(4-(((3R,3aS,6S,6aS)-6-(4'-trans-(4-pentylcyclohexyl)biphenylcarbonyloxy) hexahydrofuro[3,2-b]furan-3-yloxy)carbonyl)phenyl.

More specifically, the compounds described herein can be chosen from:

3,3-Bis(4-methoxyphenyl)-10-[4-(4-(trans-4-pentylcyclohexyl)benzamido)phenyl]-13,13-dimethyl-12-bromo-3, 13-dihydro-indeno[2',3':3,4]naphtho[1,2-b]pyran;
3,3-Bis(4-methoxyphenyl)-10-[4-((4-(trans-4-pentylcyclohexyl)phenoxy)carbonyl)phenyl]-6,13,13-trimethyl-3,13-dihydro-indeno[2', 3':3,4]naphtho[1,2-b]pyran;
3-(4-Fluorophenyl)-3-(4-piperidinophenyl)-10-[4-(4-(4-(trans-4-pentylcyclohexyl)phenyl)benzamido) phenyl]-6-trifluoromethyl-11,13,13-trimethyl-3,13-dihydro-indeno [2',3':3,4]naphtho[1,2-b]pyran;
3,3-Bis(4-methoxyphenyl)-10-[4-(4-(trans-4-pentylcyclohexyl)benzamido)phenyl]-5,7-difluoro-13,13-dimethyl-3, 13-dihydro-indeno[2',3':3,4]naphtho[1,2-b]pyran;
3-(4-Methoxyphenyl)-3-(4-piperidinophenyl)-10-[4-(4-(4-(trans-4-pentylcyclohexyl)phenyl)benzamido) phenyl]-5, 7-difluoro-13,13-dimethyl-3,13-dihydro-indeno[2',3':3,4] naphtho[1,2-b]pyran;
3-(4-Methoxyphenyl)-3-(4-morpholinophenyl)-10-[4-(4-(4-(trans-4-pentylcyclohexyl)phenyl)benzamido)phenyl]-5, 7-difluoro-13,13-dimethyl-3,13-dihydro-indeno[2',3':3,4] naphtho[1,2-b]pyran;
3-(4-Fluorophenyl)-3-(4-piperidinophenyl)-10-[4-((4-(trans-4-pentylcyclohexyl)phenoxy)carbonyl)phenyl]-12-bromo-5,7-difluoro-13,13-dimethyl-3,13-dihydro-indeno [2',3':3,4]naphtho[1,2-b]pyran;
3-Phenyl-3-(4-piperidinophenyl)-10-[4-(4-(4-(trans-4-pentylcyclohexyl)phenyl)benzamido)phenyl]-12-bromo-5,7-difluoro-13,13-dimethyl-3,13-dihydro-indeno[2',3':3,4] naphtho[1,2-b]pyran;
3-Phenyl-3-(4-piperidinophenyl)-10-[4-((4-(trans-4-pentylcyclohexyl)phenoxy)carbonyl)phenyl]-12-bromo-5,7-difluoro-13,13-dimethyl-3,13-dihydro-indeno[2',3':3,4] naphtho[1,2-b]pyran;

3-(4-Fluorophenyl)-3-(4-piperidinophenyl)-10-[4-(4-(4-(trans-4-pentylcyclohexyl)phenyp)benzamido)phenyl]-12-bromo-13,13-dimethyl-3,13-dihydro-indeno[2',3':3,4]naphtho[1,2-b]pyran;

3,3-Bis(4-methoxydinophenyl)-10-[4-(4-(4-(trans-4-pentylcyclohexyl)phenyl)benzamido)phenyl]-12-bromo-6,7-dimethoxy-11,13,13-trimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-6-trifluoromethyl-12-bromo-13,13-dimethyl-3,13-dihydro-indeno[2',3':3,4]naphtho[1,2-b]pyran;

3,3-Bis(4-methoxyphenyl)-10,12-bis[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-5,7-difluoro-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-5,7-difluoro-12-bromo-13,13-dimethyl-3,13-dihydro-indeno[2,3':3,4]naphtho[1,2-b]pyran;

3-(4-Fluorophenyl)-3-(4-morpholinophenyl)-10-[4-(4-(4-(trans-4-pentylcyclohexyl)phenyl)benzamido)phenyl]-6-trifluoromethyl-13-methyl-13-butyl-3,13-dihydro-indeno[2',3':3,4]naphtho[1,2-b]pyran;

3-(4-Fluorophenyl)-3-(4-morpholinophenyl)-10-[4-(4-(4-(trans-4-pentylcyclohexyl)phenyp)benzamido)phenyl]-5,7-difluoro-12-bromo-13,13-dimethyl-3,13-dihydro-indeno[2',3':3,4]naphtho[1,2-b]pyran;

3-Phenyl-3-(4-methoxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3-Phenyl-3-(4-morpholinophenyl)-10-[4-(4-(4-(trans-4-pentylcyclohexyl)phenyp)benzamido)phenyl]-6-trifluoromethyl-13,13-dimethyl-3,13-dihydro-indeno[2',3':3,4]naphtho[1,2-b]pyran;

3,3-Bis(4-fluorophenyl)-10-[4-(4-(4-(trans-4-pentylcyclohexyl)phenyl)benzamido)phenyl]-6-trifluoromethyl-12-bromo-13,13-dimethyl-3,13-dihydro-indeno[2',3':3,4]naphtho[1,2-b]pyran;

3,3-Bis(4-fluorophenyl)-10-[4-(4-(4-(trans-4-pentylcyclohexyl)phenyp)benzamido)phenyl]6-trifluoromethyl-13,13-dimethyl-3,13-dihydro-indeno[2',3':3,4]naphtho[1,2-b]pyran;

3-(4-Methoxyphenyl)-3-(4-butoxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3-(4-Fluorophenyl)-13,13-dimethyl-3-(4-morpholinophenyl)-10-(4-(4'-(trans-4-pentylcyclohexyl)-[1,1'-biphenyl]-4-ylcarboxamido)phenyl)-6-(trifluoromethyl)-3,13-dihydro-indeno[2',3':3,4]naphtho[1,2-b]pyran;

3-(4-Butoxyphenyl)-3-(4-fluorophenyl)-13,13-dimethyl-10-(4-(4'-(trans-4-pentylcyclohexyl)-[1,1'-biphenyl]-4-ylcarboxamido)phenyl)-6-(trifluoromethyl)-3,13-dihydro-indeno[2',3':3,4]naphtho[1,2-b]pyran;

3-(4-(4-(4-Methoxyphenyl)piperazin-1-yl)phenyl)-13,13-dimethyl-10-(4-(4'-(trans-4-pentylcyclohexyl)-[1,1'-biphenyl]-4-ylcarboxamido)phenyl)-3-phenyl-6-(trifluoromethyl)-3,13-dihydro-indeno[2',3':3',4]naphtho[1,2-b]pyran;

3-(4-Butoxyphenyl)-3-(4-fluorophenyl)-13,13-dimethyl-10-(4-(((trans,trans-4'-pentyl-[1,1'-bi(cyclohexan)]-4-yl)oxy)carbonyl)phenyl)-6-(trifluoromethyl)-3,13-dihydro-indeno[2',3':3,4]naphtho[1,2-b]pyran;

3-(4-Fluorophenyl)-13,13-dimethyl-10-(4-(4'-(trans-4-pentylcyclohexyl)-[1,1'-biphenyl]-4-ylcarboxamido)phenyl)-3-(4-butoxyphenyl)-6-(trifluoromethyl)-3,13-dihydro indeno[2',3':3,4]naphtho[1,2-b]pyran;

3-(4-Methoxyphenyl)-13,13-dimethyl-10-(4-(4'-(trans-4-pentylcyclohexyl)-[1,1'-biphenyl]-4-ylcarboxamido)phenyl)-3-(4-(trifluoromethoxy)phenyl)-6-(trifluoromethyl)-3,13-dihydro-indeno[2',3':3,4]naphtho[1,2-b]pyran;

3,3-Bis(4-hydroxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

12-Bromo-3-(4-butoxyphenyl)-3-(4-fluorophenyl)-13,13-dimethyl-10-(4-((4'-(trans-4-pentylcyclohexyl)-[1,1'-biphenyl]-4-carbonyl)oxy)benzamido)-6-(trifluoromethyl)-3,13-dihydro-indeno[2',3':3,4]naphtho[1,2-b]pyran;

3-(4-Butoxyphenyl)-5,7-dichloro-11-methoxy-3-(4-methoxyphenyl)-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

3-(4-Butoxyphenyl)-3-(4-fluorophenyl)-13,13-dimethyl-10-(4-((4'-(trans-4-pentylcyclohexyl)-[1,1'-biphenyl]-4-carbonyl)oxy)benzamido)-6-(trifluoromethyl)-3,13-dihydro-indeno[2',3':3,4]naphtho[1,2-b]pyran;

5,7-Dichloro-3,3-bis(4-hydroxyphenyl)-11-methoxy-13,13-dimethyl-10-(4-(4'-(trans-4-pentylcyclohexyl)-[1,1-biphenyl]-4-ylcarboxamido)phenyl)-3,13-dihydro-indeno[2',3':3,4]naphtho[1,2-b]pyran;

6,8-Dichloro-3,3-bis(4-hydroxyphenyl)-11-methoxy-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

3-(4-Butoxyphenyl)-5,8-difluoro-3-(4-fluorophenyl)-13,13-dimethyl-10-(4-(4'-(trans-4-pentylcyclohexyl)-[1,1-biphenyl]-4-ylcarboxamido)phenyl)-3,13-dihydro-indeno[2',3':3,4]naphtho[1,2-b]pyran;

3-(4-Butoxyphenyl)-3-(4-fluorophenyl)-13,13-dimethyl-10-(4-(4'-(trans-4-pentylcyclohexyl)-[1,1'-biphenyl]-4-carbonyl)piperazin-1-yl)-6-(trifluoromethyl)-3,13-dihydro-indeno[2',3':3,4]naphtho[1,2-b]pyran;

3-(4-Morpholinophenyl)-3-(4-methoxyphenyl)-10,7-bis[4-(4-(4-(trans-4-pentylcyclohexyl)phenyl)benzamido)phenyl]-5-fluoro-13,13-dimethyl-3,13-dihydro-indeno[2',3':3,4]naphtho[1,2-b]pyran;

3-(4-Morpholinophenyl)-3-(4-methoxyphenyl)-10-[4-(4-(4-(trans-4-pentylcyclohexyl)phenyl)benzamido)-2-(trifluoromethyl)phenyl]-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)-2-(trifluoromethyl)phenyl]-13,13-dimethyl-3,13-dihydro-indeno[2',3':3,4]naphtho[1,2-b]pyran;

3-(4-Morpholinophenyl)-3-(4-methoxyphenyl)-10-[4-(4-(4-(trans-4-pentylcyclohexyl)phenyl)benzamido)-2-(trifluoromethyl)phenyl]-13,13-dimethyl-3,13-dihydro-indeno[2',3':3,4]naphtho[1,2-b]pyran;

3,3-Bis(4-methoxyphenyl)-13,13-dimethyl-10-(2-methyl-4-(trans-4-((4'-(((trans-4-pentylcyclohexyl)biphenyl-4-yloxy)carbonyl)cyclohexanecarboxamido)phenyl)-3,13-dihydro-indeno[2',3':3,4]naphtho[1,2-b]pyran;

3-(4-(4-(4-Butylphenyl)piperazin-1-yl)phenyl)-3-(4-methoxyphenyl)-13,13-dimethyl-10-(4-(4'-(trans-4-pentylcyclohexyl)biphenyl-4-ylcarboxamido)-2-(trifluoromethyl)phenyl)-3,13-dihydro-indeno[2',3':3,4]naphtho[1,2-b]pyran;

3-(4-(4-(4-Butylphenyl)piperazin-1-yl)phenyl)-3-(4-methoxyphenyl)-13,13-dimethyl-10-(2-methyl-4-(4'-(trans-4-pentylcyclohexyl)biphenyl-4-ylcarboxamido)phenyl)-7-(4-(4-(trans-4-pentylcyclohexyl)benzamido)phenyl)-3,13-dihydro-indeno[2',3':3,4]naphtho[1,2-b]pyran;

3-(4-Methoxyphenyl)-13,13-dimethyl-7,10-bis(4-(4'-(trans-4-pentylcyclohexyl)biphenyl-4-ylcarboxamido)phenyl)-3-phenyl-3,13-dihydro-indeno[2',3':3,4]naphtho[1,2-b]pyran;

3-p-Tolyl-3-(4-methoxyphenyl)-6-methoxy-13,13-dimethyl-7-(4'-(trans,trans-4'-pentylbi(cyclohexane-4-)carbonyloxy)biphenylcarbonyloxy)-10-(4-(4'-(trans-4-pentylcyclohexyl)biphenyl-4-ylcarboxamido)phenyl)-3,13-dihydro-indeno[2',3':3,4]naphtho[1,2-b]pyran;

10-(4-(((3S,8S,9S,10R,13R,14S,17R)-10,13-Dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl)-3-(4-methoxyphenyl)-13,13-dimethyl-3-(4-morpholinophenyl)-3,13-dihydro-indeno[2',3':3,4]naphtho[1,2-b]pyran;

6-Methoxy-3-(4-methoxyphenyl)-13,13-dimethyl-3-(4-((S)-2-methylbutoxy)phenyl)-10-(4-(4'-(trans-4-pentylcyclohexyl)biphenyl-4-ylcarboxamido)phenyl)-3,13-dihydro-indeno[2',3':3,4]naphtho[1,2-b]pyran;

6-Methoxy-3-(4-methoxyphenyl)-13,13-dimethyl-3-(4-((S)-2-methylbutoxy)phenyl)-7-(4'-(trans,trans-4'-pentylbi(cyclohexane-4-)carbonyloxy)biphenylcarbonyloxy)-10-(4-(4'-(trans-4-pentylcyclohexyl)biphenyl-4-ylcarboxamido)phenyl)-3,13-dihydro-indeno[2',3':3,4]naphtho[1,2-b]pyran; and 6-Methoxy-3-(4-methoxyphenyl)-13,13-dimethyl-3-(4-((S)-2-methylbutoxy)phenyl)-10-(4-(((3R,3aS,6S,6aS)-6-(4'-(trans-4-pentylcyclohexyl)biphenylcarbonyloxy)hexahydrofuro[3,2-b]furan-3-yloxy)carbonyl)phenyl)-3,13-dihydro-indeno[2',3':3,4]naphtho[1,2-b]pyran.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the reaction schemes and examples below, and in the references cited herein.

In the schemes and examples below, the following abbreviations have the following meanings. If an abbreviation is not defined, it has its generally accepted meaning.

| | |
|---|---|
| BINAP = | 2,2'-bis(diphenylphosphino)-1,1'-binaphthyl |
| Bi(OTf)$_3$ = | bismuth triflate |
| CuI = | copper iodide |
| DHP = | 3,4-dihydro-2H-pyran |
| DCC = | dicyclohexylcarbodiimide |
| DCM = | dichloromethane |
| DBSA = | dodecylbenzenesulfonic acid |
| DIBAL = | diisobutylaluminium hydride |
| DMAP = | 4-dimethylaminopyridine |
| DME = | dimethyl ether |
| DMF = | N,N-dimethylformamide |
| DMSO = | dimethylsulfoxide |
| Dppf = | 1,1'-bis(diphenylphosphino)ferrocene |
| EtMgBr = | ethyl magnesium bromide |
| Et$_2$O = | diethylether |
| g = | gram |
| h = | hour |
| HPLC = | high-performance liquid chromatography |
| (iPr)$_2$NH = | diisopropyl amine |
| HOAc = | acetic acid |
| LDA = | lithium diisopropylamide |
| KMnO$_4$ = | potassium permanganate |
| M = | molar (molarity) |
| mCPBA = | meta-Chloroperoxybenzoic acid |
| MeLi = | methyl lithium |
| mg = | milligram |
| min = | minutes |
| mL = | milliliter |
| mmol = | millimoles |
| mM = | millimolar |
| NatOBu = | sodium tert-butoxide |
| N = | normal (normality) |
| ng = | nanogram |
| nm = | nanometer |
| nM = | nanomolar |
| NMP = | N-methyl pyrrolidone |
| NMR = | nuclear magnetic resonance |
| Pd(OAc)$_2$ = | palladium acetate |
| Pd$_2$(dba)$_3$ = | tris(dibenzylideneacetone)dipalladium(0) |
| PPh$_3$ = | triphenyl phosphine |
| PPTS = | pyridine p-toluenesulfonate |
| pTSA = | p-toluenesulfonic acid |
| PdCl$_2$(PPh$_3$)$_2$ = | bis(triphenylphosphine)palladium(II) chloride |
| PBS = | phosphate buffered saline |
| TBAF = | Tetra-n-butylammonium fluoride |
| THF = | tetrahyrdofuran |
| TLC = | thin layer chromatography |
| t-BuOH = | t-butanol |
| (Tf)$_2$O = | trifluoromethanesulfonic acid anhydride |
| μL = | microliter |
| μM = | micromolar |
| Zn(OAc)$_2$ = | zinc acetate |
| Zn(CN)$_2$ = | Zinc cyanide |

As discussed in the schemes outlined further below, compound 105 represents one intermediate that may serve as the basis for preparing the photochromic dichroic dyes described herein. For example, it can be prepared as shown in Scheme 1, 2, 3, 4 and 5. Once prepared, the hydroxy functionality of compound 105 can be used for pyran formation as observed in Scheme 6. The halogen of 105 can be either converted into a lengthening group via Suzuki Reaction or converted into other functional group Q as illustrated in Scheme 6. Chemistries that can be used for functional group conversion can be observed in Scheme 7, 8 and 9. The new functional group Q can either be a lengthening group or be converted to lengthening group.

In all schemes, X may be selected from halogen, e.g., F, Br, Cl and I. Each m and n is an integer chosen from 0 to the total number of available positions. From Scheme 1 to Scheme 9, $R_3$ for each occurrence, may be independently selected from hydrogen, halogen and optionally substituted chiral or achiral groups selected from alkyl, perfluoroalkyl, alkenyl, alkynyl, cycloalkyl, aryl, heteroaryl, alkoxy, perfluoroalkoxy, heteroalkyl, heterocycloalkyl, alkylthiol, arylthiol, amino aminocarbonyl, aryloxycarbonyl, alkyloxycarbonyl, aminocarbonyloxy, alkoxycarbonylamino, aryloxycarbonylamino, cycloalkoxycarbonylamino, heterocycloalkyloxycarbonylamino and heteroaryloxycarbonylamino. $R_4$ is selected from $R_3$.

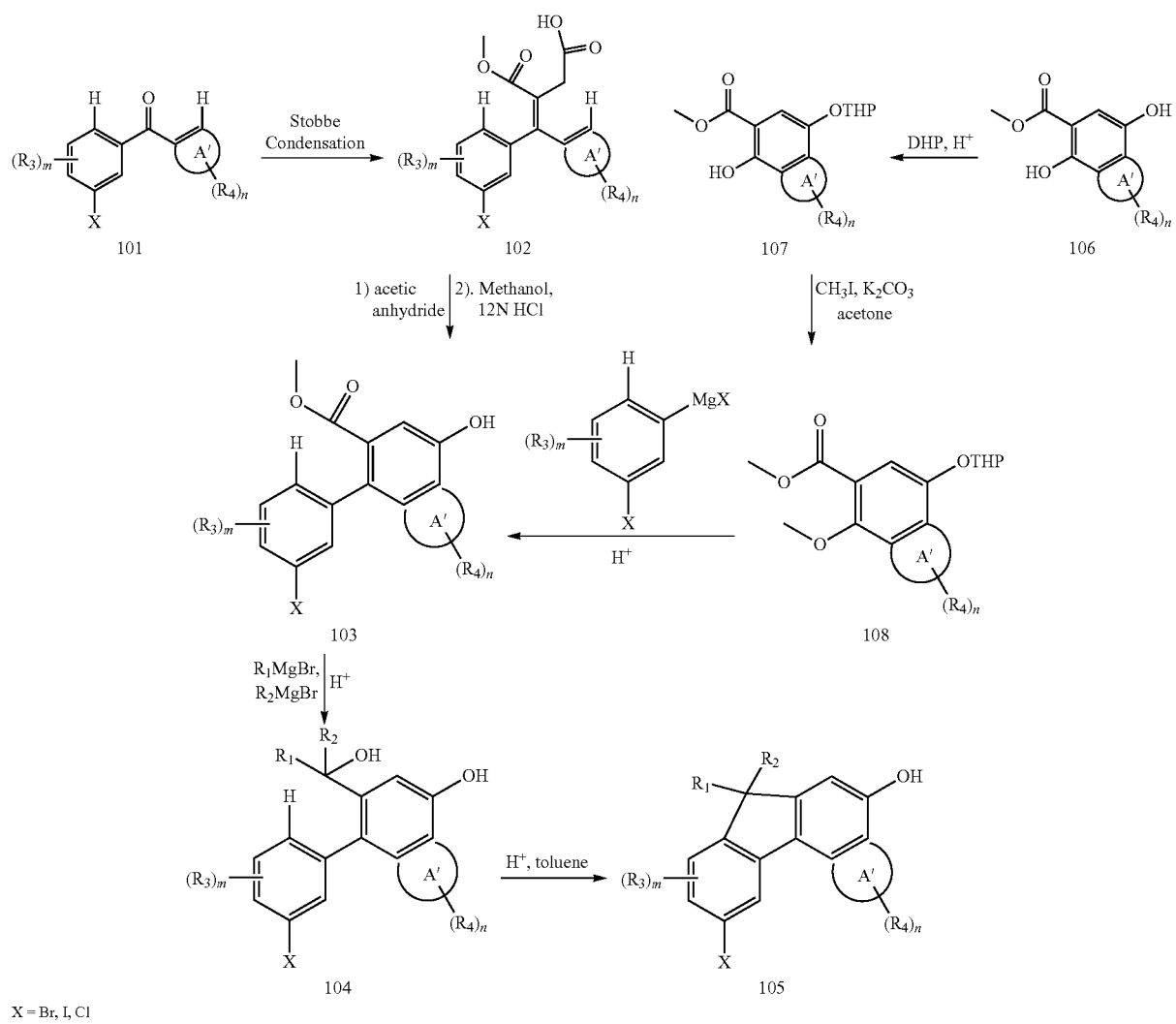

Scheme 1

X = Br, I, Cl

Scheme 1 shows one way of preparing compound 105. $R_1$ and $R_2$ may be selected from optionally substituted chiral or achiral groups such as heteroalkyl, alkyl, perfluoroalkyl, alkenyl, alkynyl, aryl, heteroaryl, cycloalkyl, and heterocycloalkyl.

The aryl ketone 101 can either be purchased or prepared by Friedel-Crafts methods or Grignard or Cuperate methods known in the art. For example, see the publication *Friedel-Crafts and Related Reactions*, George A. Olah, Interscience Publishers, 1964, Vol. 3, Chapter XXXI (Aromatic Ketone Synthesis); "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; "Addition of Grignard Reagents to Aryl Acid Chlorides: An efficient synthesis of aryl ketones" by Wang, Xiaojun et al, Organic Letters, Vol. 7, No. 25, 5593-5595, 2005, and references cited therein, which disclosures related to the aforementioned synthetic methods are incorporated herein by reference in their entireties. A Stobbe reaction of aryl ketone 101 with dimethyl succinate in the presence of potassium t-butoxide provides the condensed product of compound 102, which undergoes a ring closure reaction in acetic anhydride followed by methanolysis to form the product of compound 103.

Compound 103 can also be prepared from an ester-mediated nucleophilic aromatic substitution reaction starting from compound 106 by methods known to those skilled in the art, for example, as further described in Synthesis, January 1995, pages 41-43; The Journal of Chemistry Society Perkin Transaction 1, 1995, pages 235-241 and U.S. Pat. No. 7,557,208 B2, which disclosures related to such synthetic methods are incorporated herein by reference in their entireties.

Once prepared, compound 103 can be further converted to indeno-fused product of compound 105 with various substitutions on the bridge carbon via various multistep reactions that can be found in U.S. Pat. Nos. 5,645,767; 5,869,658; 5,698,141; 5,723,072; 5,961,892; 6,113,814; 5,955,520; 6,555,028; 6,296,785; 6,555,028; 6,683,709; 6,660,727; 6,736,998; 7,008,568; 7,166,357; 7,262,295; 7,320,826 and 7,557,208, which disclosures related to the substituents on the bridge carbon are incorporated herein by reference in their entireties. What is shown in Scheme 1 illustrates that compound 103 reacts with Grignard reagent followed by a ring closure reaction to provide compound 105.

Scheme 2

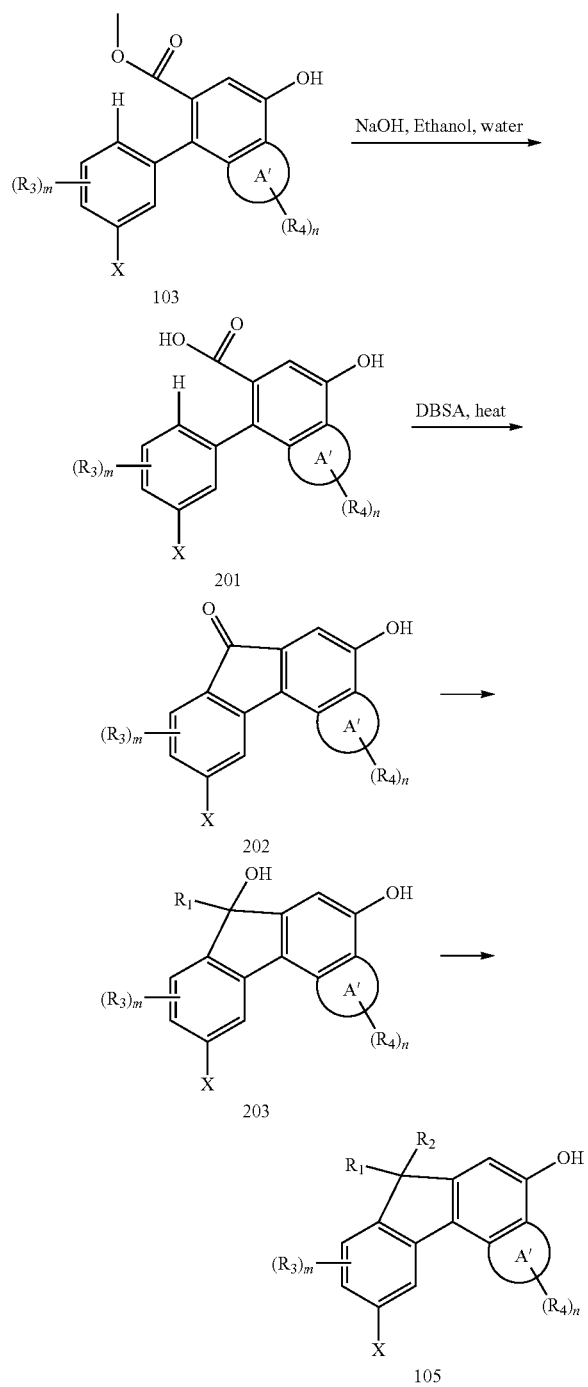

Scheme 3

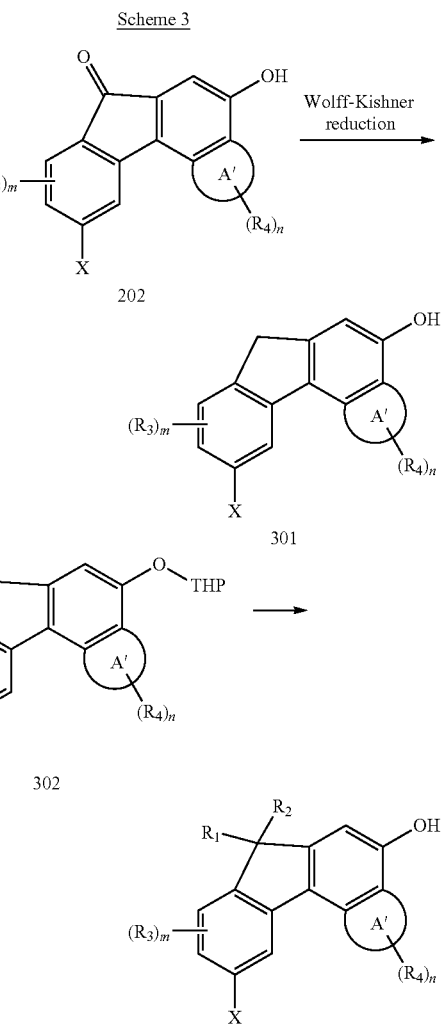

Scheme 2 illustrates a second way of converting compound 103 to compound 105. After hydrolysis of compound 103 followed by a ring closure reaction, compound 202 was obtained. The carbonyl of compound 202 can react with a nucleophile, like Grignard reagent, Organo lithium reagent, or perfluoalkyl trimethylsilane to form compound 203. $R_1$ may be selected from optionally substituted chiral or achiral groups such as heteroalkyl, alkyl, perfluoroalkyl, alkenyl, alkynyl, aryl, heteroaryl, cycloalkyl and heterocycloalkyl. The hydroxyl group of compound 203 can be easily converted into $R_2$, which may be selected from halogen and optionally substituted chiral or achiral groups such as alkoxy, silanoxy, heteroaryloxy and aryloxy.

Scheme 3 illustrates a third way of converting compound 103 to compound 105. Compound 202 from Scheme 2 can be reduced to 301 using a Wolff-Kishner reduction or its modified version. Examples can be found in "Practical procedures for the preparation of N-tert-butyldimethylsilylhydrozones and their use in modified Wolff-Kishner reductions and in the synthesis of vinyl halides and gem-dihalides" by Furrow, M. E., et al, J Am Chem Soc: 126(17): 5436-45, May 5, 2004, and references therein, which disclosures related to the Wolff-Kishner reduction are incorporated herein by reference. After hydroxy protection, compound 302 has a very nucleophilic gem-carbon once deprotonated by base like LDA or methyl Grignard reagent. By those skilled in the art, the deprotonated compound 302 can be converted to $R_1$ and $R_2$ by reacting it with electrophiles such as alkyl halides, carbon dioxide, acid chlorides, nitriles and chloroformate derivatives. As a result, compound 105 can be prepared with $R_1$ and $R_2$ selected from hydrogen, optionally substituted chiral or achiral groups selected from heteroalkyl, alkyl, cycloalkyl, carboxy, alkylcarbonyl, alkoxycarbonyl, alkylcarbonyl, alkoxycarbonyl, aminocarbonyl, arylcarbonyl, aryloxycarbonyl, or $R_1$ and $R_2$ may be taken together with any intervening atoms to form a group selected from oxo, optionally substituted cycloalkyl, and optionally substituted heterocycloalkyl.

Schemes 4 and 5 summarize two novel methods of preparing compound 105, which are not believed to have been previously described.

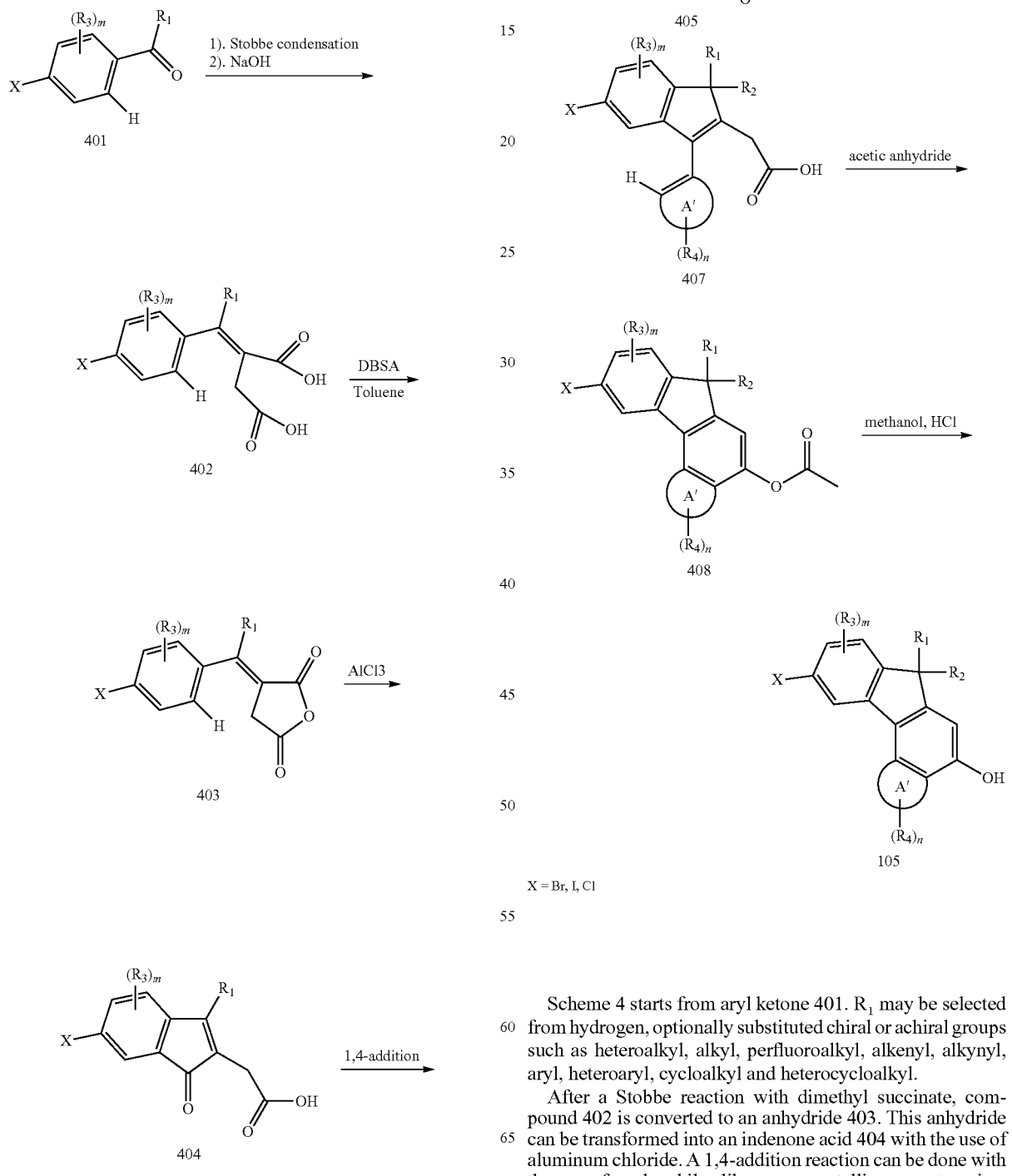

X = Br, I, Cl

Scheme 4 starts from aryl ketone 401. $R_1$ may be selected from hydrogen, optionally substituted chiral or achiral groups such as heteroalkyl, alkyl, perfluoroalkyl, alkenyl, alkynyl, aryl, heteroaryl, cycloalkyl and heterocycloalkyl.

After a Stobbe reaction with dimethyl succinate, compound 402 is converted to an anhydride 403. This anhydride can be transformed into an indenone acid 404 with the use of aluminum chloride. A 1,4-addition reaction can be done with the use of nucleophiles like organometallic reagent, amine, alcohol and thiol. The reaction provides indano acid 405. R₂ may be selected from hydrogen, optionally substituted chiral or achiral groups such as heteroalkyl, alkyl, alkenyl, alkynyl, aryl, heteroaryl, cycloalkyl, heterocycloalkyl, amino, alkoxy, and thiol. Compound 405 can react with a Grignard reagent 406 to form compound 407 after acidic workup. Compound 407 undergoes a ring closure reaction in acetic anhydride followed by methanolysis to form product 408, which can be either used directly in Scheme 6 or converted to compound 105 by hydrolysis.

Scheme 5 starts from Stobbe product 102, which reacts with Grignard reagents to provide compound 501. $R_1$ and $R_2$ may be selected from optionally substituted chiral or achiral groups such as heteroalkyl, alkyl, perfluoroalkyl, alkenyl, alkynyl, aryl, heteroaryl, cycloalkyl and heterocycloalkyl. After treating with bismuth triflate in toluene and then acetic anhydride, two ring closure reactions occur in the same pot sequentially. The efficient reaction results in compound 408, which can be converted into compound 105.

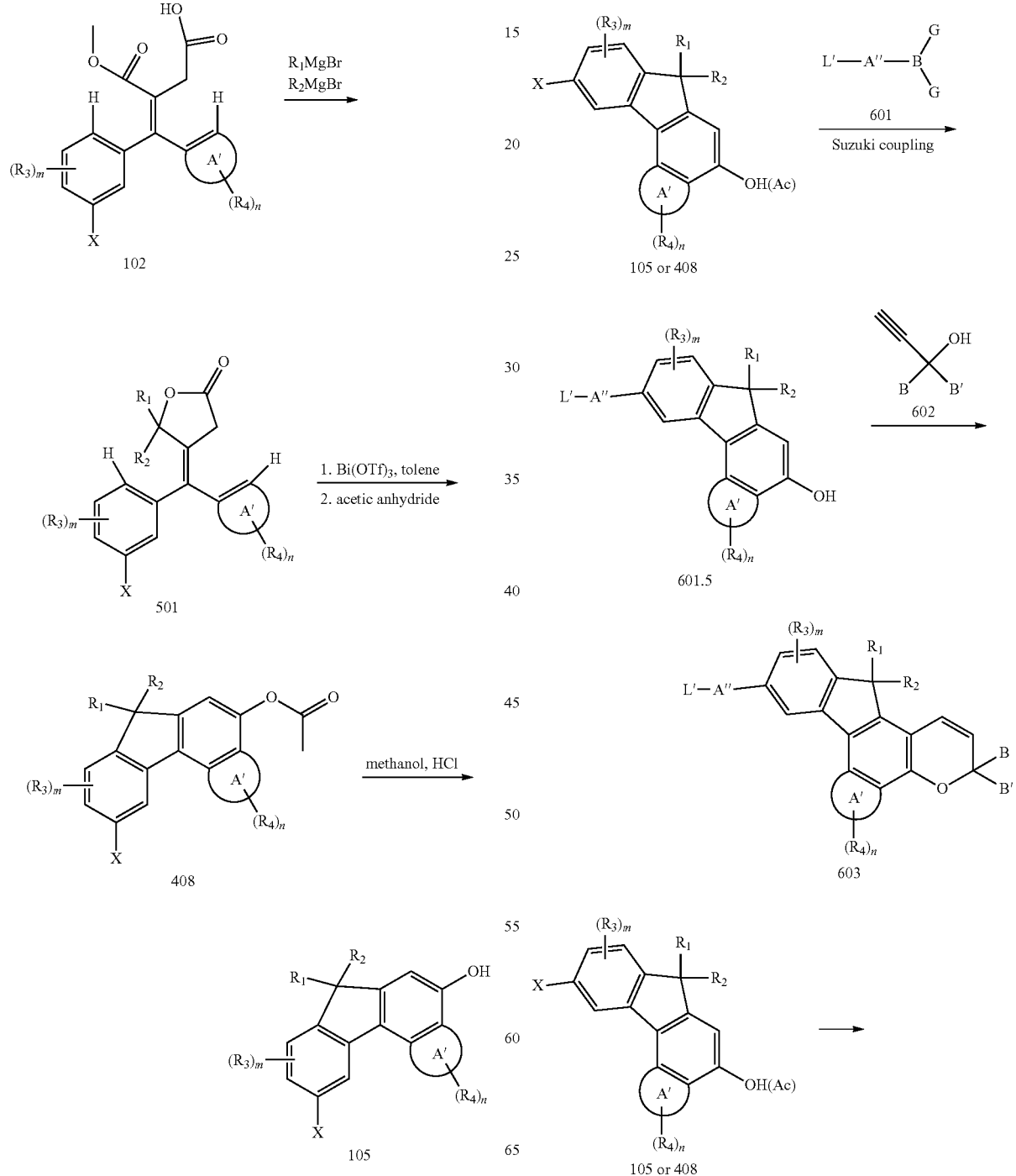

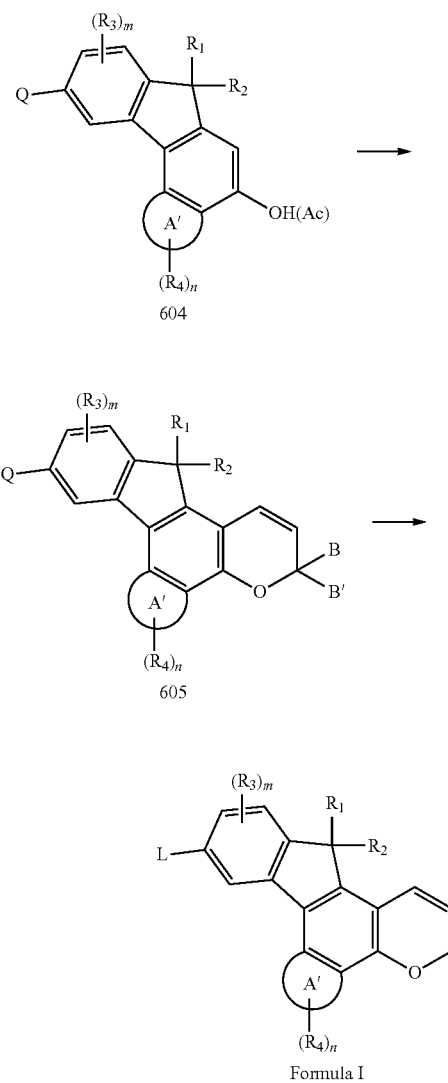

604

605

Formula I

Scheme 6 illustrates methods of converting compounds 105 and 408 into photochromic dichroic dyes. When Suzuki reaction is applied, the lengthening group is added with the use of a boronic derivative 601, the synthesis of which can be found from "Palladium(0)-Catalyzed Cross-Coupling Reaction of Alkoxydiboron with Haloarenes: A Direct Procedure for Arylboronic Esters, J. Org. Chem. 60, page 7508-7519, 1995" by Miyaura, Norio et als and references therein, which disclosures related to such synthetic methods are incorporated herein by reference. The pyran ring of compound 603 is formed with the coupling with a propargyl alcohol 602. Compound 603 may also be obtained when the sequence of the two reactions are changed. As described herein, G may be —OH or —O-Alkyl; A" may be selected from aryl, alkenyl, alkynyl and heteroaryl; A" and L' together form the $L_1$, $L_2$ or $L_3$ group; and B and B' may be each independently selected from $L_3$, hydrogen, halogen, and optionally substituted chiral or achiral groups such as metallocenyl, alkyl or perfluoroalkyl, alkenyl, alkynyl, heteroalkyl, alkoxy, perfluoroalkoxy, aryl, heteroaryl, heterocycloalkyl, and cycloalkyl, or wherein B and B' are taken together with any intervening atoms to form a group such as optionally substituted cycloalkyl and optionally substituted heterocycloalkyl.

Also shown in Scheme 6 as alternative ways of incorporating lengthening groups, halogen X can be converted to other functional group Q with the formation of compound 604. Compound 604 can react with a propargyl alcohol to form pyran dye 605, which can be a photochromic dichroic dye itself or can be converted to photochromic dichroic dye Formula I. These new functional groups Q may include: —$N_3$, —CN, —COOR', —CCR', —CHCHR', —OCOR', —OCOOR', —SR', —$OSO_2R'$, —OR', —OTf, —CHO, —OCHO, —OCONR', —NR'R', —NR'CONR'R', —NR'COR', —NR'COOR', —CHNR', and —CONR'R', wherein R' may be independently chosen from hydrogen, L, an unsubstituted or substituted alkyl group having from 1 to 18 carbon atoms, an unsubstituted or substituted aryl group, an unsubstituted or substituted alkene or alkyne group having from 2 to 18 carbon atoms, —$CF_3$ and a perfluorinated alkyl group having from 2 to 18 carbon atoms or two R' can come together with —N and form a heterocycloalkyl such as piperazinyl.

Schemes 7, 8 and 9 illustrate details of converting halogen to other functional groups that can be either further converted to lengthening groups or are lengthening groups themselves. The chemistries are done at hydroxy stage starting from compound 105, which is simplified as compound 701 in Schemes 7 and 8. Each of the hydroxy products of compounds 702, 706, 708, 709, 710, 802, 803, 807, 809, 810, 811, 812, 901, 903, 904 and 906 can be converted to pyran photochromic compounds using the propargyl alcohol chemistry shown in Scheme 6.

Scheme 7

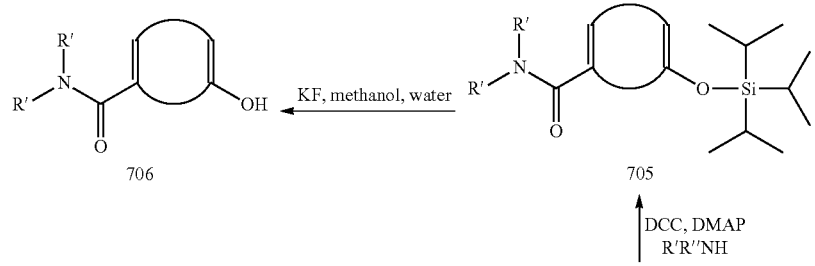

-continued
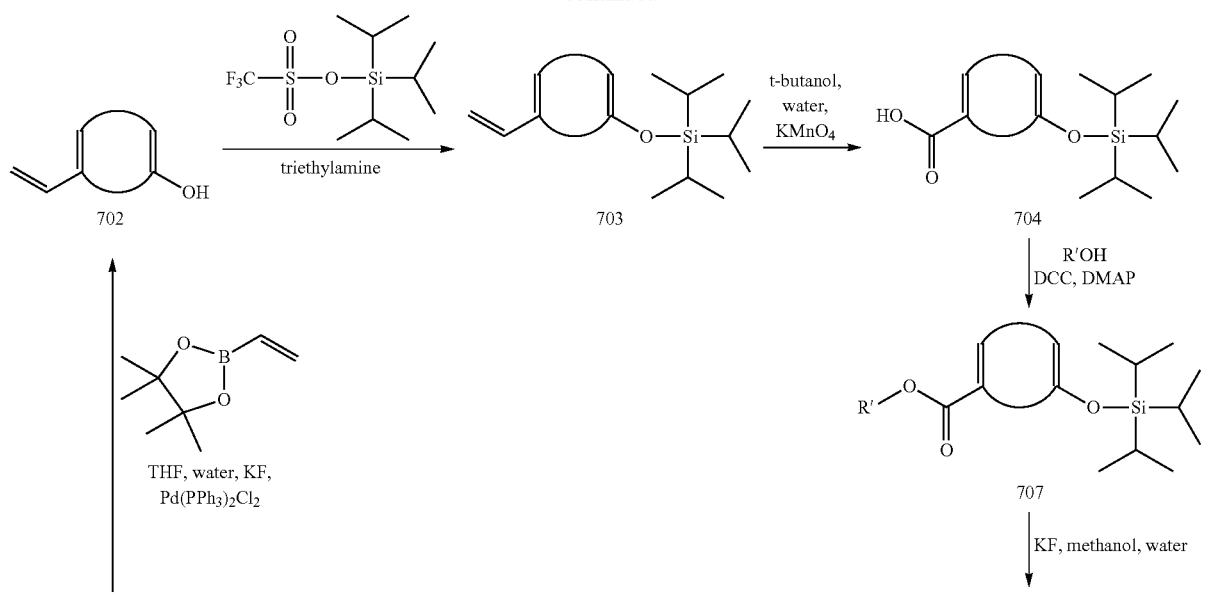
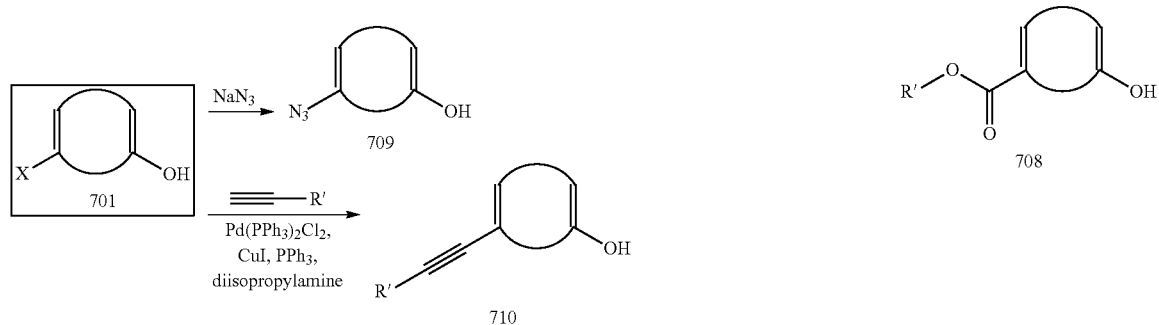
Scheme 8
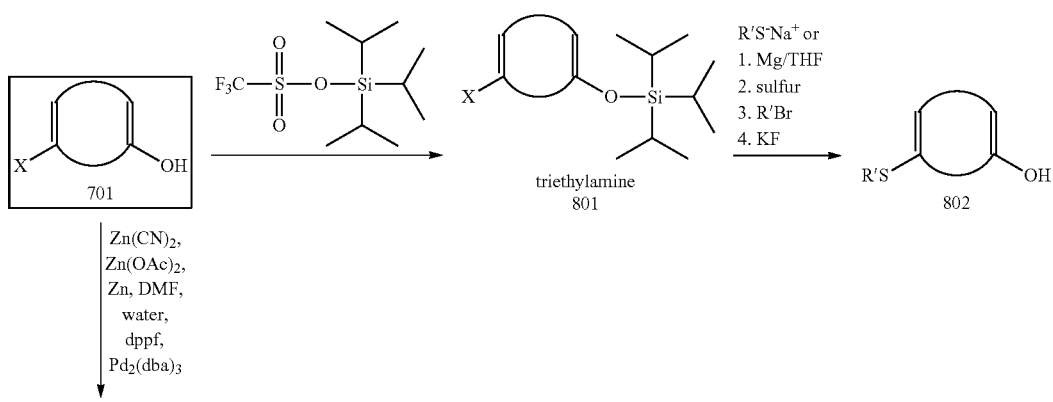

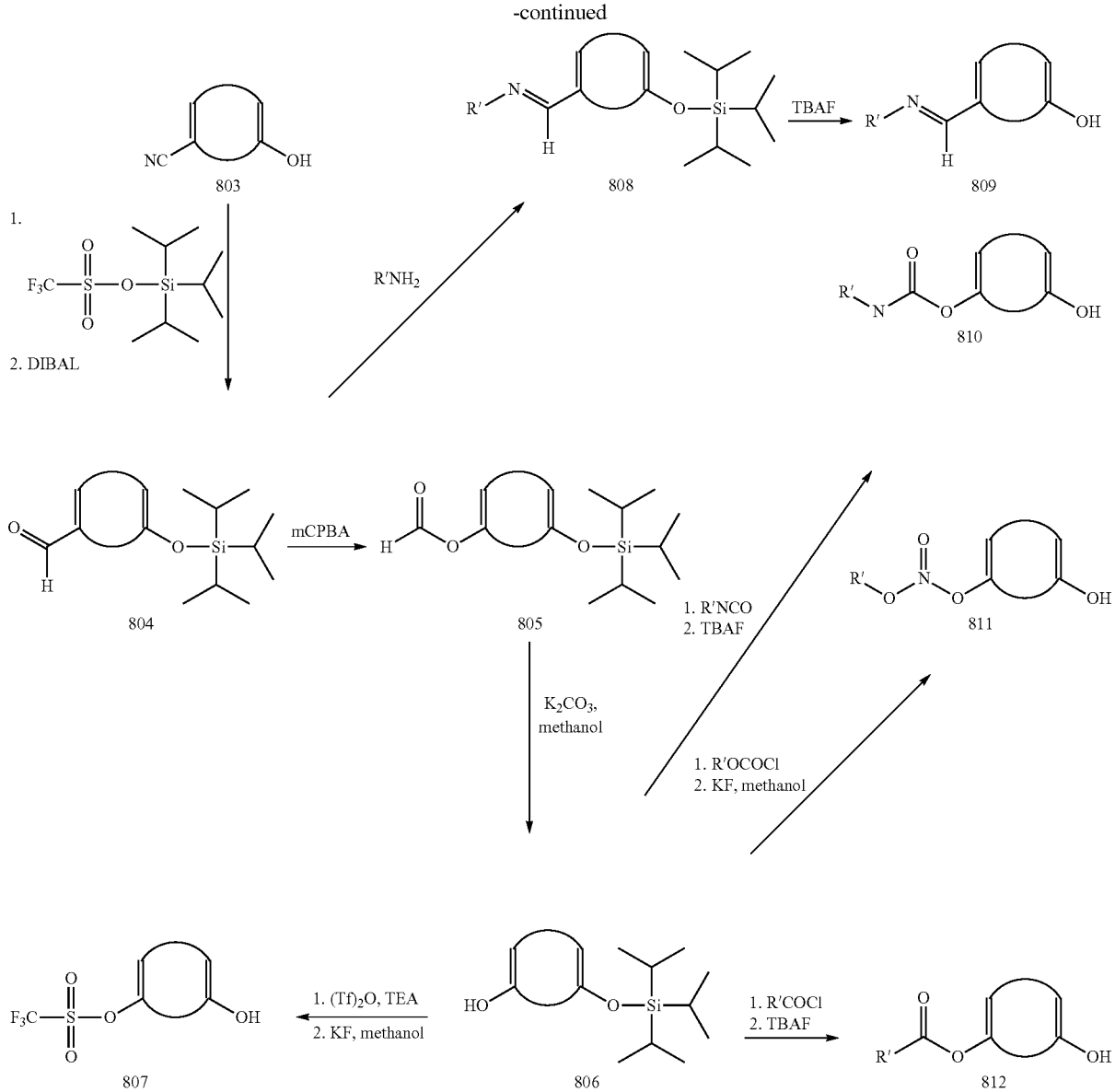
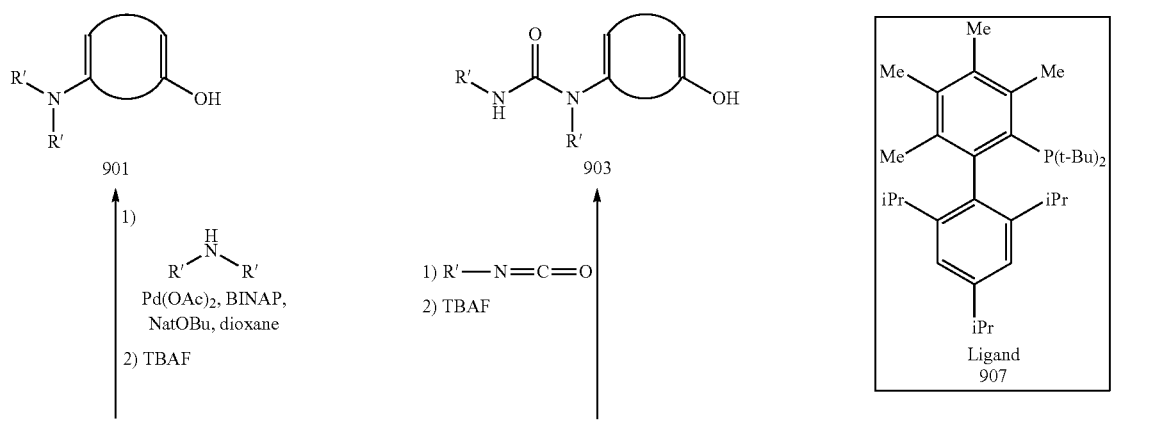
Scheme 9

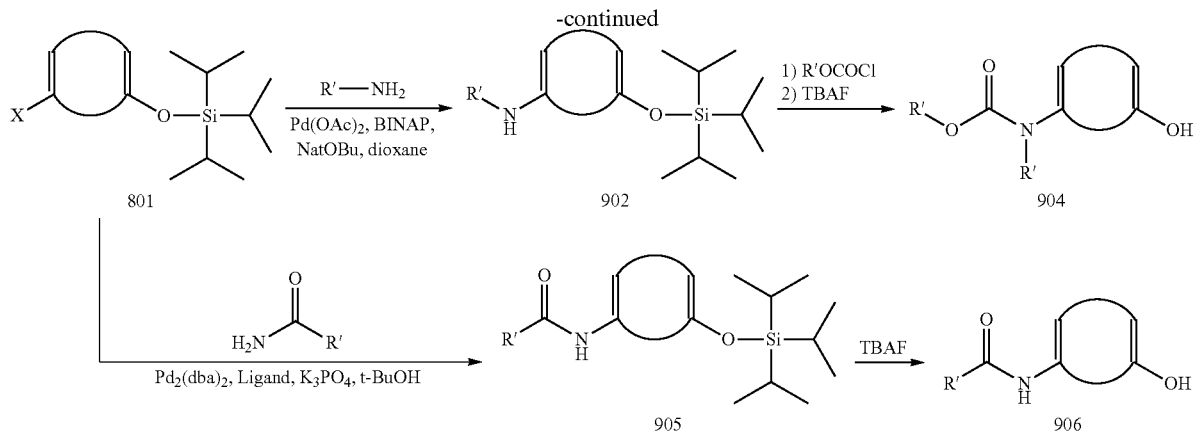

Scheme 10 shows chemistries that can be done on the photochromic dichroic dye. A''' is a simplified version of Formula I with one of $R_3$ or $R_4$ selected from halogen X. X is located at one of the positions where $R_3$ and $R_4$ would be located. This Scheme compliments what can be done from Scheme 1 to 9 for $R_3$ and $R_4$ and install groups like cyano, aldehyde, carboxylic acid, and optionally substituted chiral or achiral groups selected from imine, alkoxycarbonyl, aminocarbonyl and aryloxycarbonyl as $R_3$ and $R_4$. The cyanation and oxidation methods have been described in U.S. Patent Pub. No. 2009/0309076A1, wherein these cyanation and oxidation methods are incorporated herein by reference.

(a) a single photochromic compound;
(b) a mixture of photochromic compounds;
(c) a material comprising at least one photochromic compound such as a polymeric resin or an organic monomer solution;
(d) a material such as a monomer or polymer to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

Scheme 10

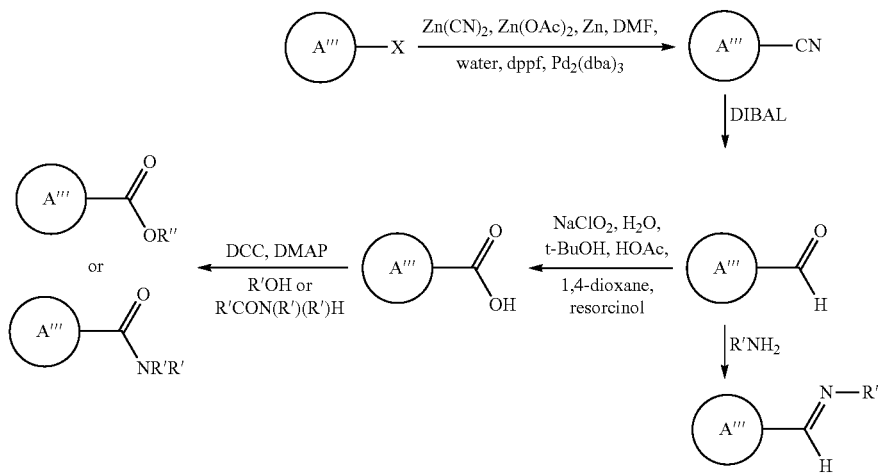

The compounds described herein may be useful as thermally reversible photochromic compounds and/or compositions according to various non-limiting embodiments disclosed herein. Such compounds may be useful in a variety of applications to provide photochromic and/or photochromic-dichroic properties.

The photochromic compositions of the present invention may comprise at least one of the compounds described herein, and optionally at least one other photochromic compound. The photochromic composition can be chosen from a variety of materials. Examples of such materials may be selected from:

The present invention further provides a photochromic article comprising an organic material and a photochromic compound/composition of the present disclosure connected to at least a portion of the organic host material. As used herein the term "connected to" means in direct contact with an object or indirect contact with an object through one or more other structures or materials, at least one of which is in direct contact with the object. Further, the photochromic compound can be connected to at least a portion of the host by incorporation into the host material or by application onto the host material, for example, as part of a coating or layer. In addition to the photochromic compound, the photochromic composition may further comprise at least one additive chosen from dyes, alignment promoters, antioxidants, kinetic enhancing additives, photoinitiators, thermal initiators, polymerization inhibitors, solvents, light stabilizers, e.g., ultraviolet light absorbers and hindered amines stabilizers, heat stabilizers, mold release agents, rheology control agents, leveling agents, free radical scavengers, gelators and adhesion promoters.

Examples of dyes that can be present in the at least partial coating according to various embodiments disclosed herein include organic dyes that are capable of imparting a desired color or other optical property to the at least partial coating.

As used herein, the term "alignment promoter" means an additive that can facilitate at least one of the rate and uniformity of the alignment of a material to which it is added. Examples of alignment promoters that can be present in the at least partial coatings according to various embodiments disclosed herein include those described in U.S. Pat. No. 6,338,808 and U.S. Patent Publication No. 2002/0039627.

Antioxidants, e.g., polyphenolic antioxidants, are organic compounds used to retard oxidation. Examples of antioxidants are described in U.S. Pat. Nos. 4,720,356, 5,391,327 and 5,770,115, the disclosures of which are incorporated herein by reference.

Examples of kinetic enhancing additives that can be present in the at least partial coating according to various embodiments disclosed herein include epoxy-containing compounds, organic polyols, and/or plasticizers. More specific examples of such kinetic enhancing additives are disclosed in U.S. Pat. No. 6,433,043 and U.S. Patent Publication No. 2003/0045612.

Examples of photoinitiators that can be present in the at least partial coating according to various embodiments disclosed herein include cleavage-type photoinitiators and abstraction-type photoinitiators. Examples of cleavage-type photoinitiators include acetophenones, α-aminoalkylphenones, benzoin ethers, benzoyl oximes, acylphosphine oxides and bisacylphosphine oxides or mixtures of such initiators. A commercial example of such a photoinitiator is DAROCURE® 4265, which is available from Ciba Chemicals, Inc. Examples of abstraction-type photoinitiators include benzophenone, Michler's ketone, thioxanthone, anthraquinone, camphorquinone, fluorone, ketocoumarin or mixtures of such initiators.

Another Example of a photoinitiator that can be present in according to various embodiments disclosed herein is a visible light photoinitiator. Examples of suitable visible light photoinitiators are set forth at column 12, line 11 to column 13, line 21 of U.S. Pat. No. 6,602,603.

Examples of thermal initiators include organic peroxy compounds and azobis(organonitrile) compounds. Specific examples of organic peroxy compounds that are useful as thermal initiators include peroxymonocarbonate esters, such as tertiarybutylperoxy isopropyl carbonate; peroxydicarbonate esters, such as di(2-ethylhexyl) peroxydicarbonate, di(secondary butyl) peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide and p-chlorobenzoyl peroxide; peroxyesters such as t-butylperoxy pivalate, t-butylperoxy octylate and t-butylperoxyisobutyrate; methylethylketone peroxide, and acetylcyclohexane sulfonyl peroxide. In one embodiment the thermal initiators used are those that do not discolor the resulting polymerizate. Examples of azobis(organonitrile) compounds that can be used as thermal initiators include azobis(isobutyronitrile), azobis(2,4-dimethylvaleronitrile) or a mixture thereof.

Examples of polymerization inhibitors include: nitrobenzene, 1,3,5,-trinitrobenzene, p-benzoquinone, chloranil, DPPH, $FeCl_3$, $CuCl_2$, oxygen, sulfur, aniline, phenol, p-dihydroxybenzene, 1,2,3-trihydroxybenzene, and 2,4,6-trimethylphenol.

Examples of solvents that can be present in the LC compositions according to various embodiments disclosed herein include those that will dissolve solid components of the LC compositions, that are compatible with the LC compositions and the elements and substrates, and/or can ensure uniform coverage of a surface(s) to which the LC composition is applied. Potential solvents include the following: propylene glycol monomethyl ether acetate and their derivates (sold as DOWANOL® industrial solvents), acetone, amyl propionate, anisole, benzene, butyl acetate, cyclohexane, dialkyl ethers of ethylene glycol, e.g., diethylene glycol dimethyl ether and their derivates (sold as CELLOSOLVE® industrial solvents), diethylene glycol dibenzoate, dimethyl sulfoxide, dimethyl formamide, dimethoxybenzene, ethyl acetate, isopropyl alcohol, methyl cyclohexanone, cyclopentanone, methyl ethyl ketone, methyl isobutyl ketone, methyl propionate, propylene carbonate, tetrahydrofuran, toluene, xylene, 2-methoxyethyl ether, 3-propylene glycol methyl ether, and mixtures thereof.

Examples of thermal stabilizers may include a basic nitrogen-containing compound for example, biurea, allantoin or a metal salt thereof, a carboxylic acid hydrazide, e.g., an aliphatic or aromatic carboxylic acid hydrazide, a metal salt of an organic carboxylic acid, an alkali or alkaline earth metal compound, a hydrotalcite, a zeolite and an acidic compound (e.g., a boric acid compound, a nitrogen-containing cyclic compound having a hydroxyl group, a carboxyl group-containing compound, a (poly)phenol, butylated hydroxytoluene, and an aminocarboxylic acid) or mixtures thereof.

Examples of mold release agents include esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

Rheology control agents are thickeners that are typically powders that may be inorganic, such as silica, organic such as microcrystalline cellulose or particulate polymeric materials. Gelators or gelling agents are often organic materials that can also affect the thixotropy of the material in which they are added. Examples of suitable gelators or gelling agents include natural gums, starches, pectins, agar-agar, and gelatins. Gelators or gelling agents may often be based on polysaccharides or proteins.

In certain embodiments, one or more surfactants may be used. Surfactants include materials otherwise known as wetting agents, anti-foaming agents, emulsifiers, dispersing agents, leveling agents etc. Surfactants can be anionic, cationic and nonionic, and many surfactants of each type are available commercially. Examples of nonionic surfactants that may be used include ethoxylated alkyl phenols, such as the IGEPAL® DM surfactants or octyl-phenoxypolyethoxyethanol sold as TRITON® X-100, an acetylenic diol such as 2,4,7,9-tetramethyl-5-decyne-4,7-diol sold as SURFYNOL® 104, ethoxylated acetylenic diols, such as the SURFYNOL®400 surfactant series, fluoro-surfactants, such as the FLUORAD® fluorochemical surfactant series, and capped nonionics such as the benzyl capped octyl phenol ethoxylates sold as TRITON® $CF_{87}$, the propylene oxide capped alkyl ethoxylates, which are available as the PLURAFAC® RA series of surfactants, octylphenoxyhexadecylethoxy benzyl ether, polyether modified dimethylpolysiloxane copolymer in solvent sold as BYK®-306 additive by Byk Chemie and mixtures of such recited surfactants.

Free radical scavengers include synthetic pseudopeptides resistant to hydrolysis such as Carcinine hydrochloride; lipoamino acids such as L-lysine lauroylmethionine; plant extracts containing multi-enzymes; natural tocopherol and related compounds as well as compounds containing an active hydrogen such as —OH, —SH, or —NRH group. Further examples of free radical scavengers are chosen from the group of sterically hindered amines (HALS=hindered amine light stabilizer) which, unlike customary light protection agents, are not based on the absorption of the irradiated light or on the quenching of the absorbed light, but essentially on the ability to scavenge or to replace free radicals and hydroperoxides formed during the photodegradation of polymeric materials and antioxidants.

Adhesion promoters include adhesion promoting organosilane materials, such as aminoorganosilane materials, silane coupling agents, organic titanate coupling agents and organic zirconate coupling agents described in U.S. Patent Application Publication 2004/0207809 at paragraphs [0033] to [0042]. Further examples of adhesion promoters include zircon-aluminate adhesion promoting compounds that are commercially available from Rhone-Poulenc. Preparation of aluminum-zirconium complexes is described in the U.S. Pat. Nos. 4,539,048 and 4,539,049. These patents describe zircoaluminate complex reaction products corresponding to the empirical formula: $(Al_2(OR_1O)_aA_bB_c)_X(OC(R_2)O)_Y(ZrA_dB_e)_Z$ wherein X, Y, and Z are at least 1, $R_2$ is an alkyl, alkenyl, aminoalkyl, carboxyalkyl, mercaptoalkyl, or epoxyalkyl group, having from 2 to 17 carbon atoms, and the ratio of X:Z is from about 2:1 to about 5:1. Additional zircoaluminate complexes are described in U.S. Pat. No. 4,650,526.

Non-limiting examples of organic host materials that may be used in conjunction with various non-limiting embodiments disclosed herein include liquid crystal materials and polymeric materials. Liquid crystal materials may be chosen from liquid crystal polymers, liquid crystal pre-polymers and liquid crystal monomers. As used herein the term "pre-polymer" means partially polymerized materials. Liquid crystal polymers ("LCPs") are polymers capable of forming regions of highly ordered structure while in a liquid phase. As used herein, the term "liquid crystal monomer" means a monomeric compound that may display liquid crystal properties in the monomeric state and/or in the polymeric state. That is, the liquid crystal monomer may display liquid crystal properties by itself and/or after it has been incorporated into a polymer or copolymer to form a liquid crystal polymer (LCP). The LCPs may display at least one of a nematic phase, a smectic phase, a chiral nematic phase (i.e., a cholesteric phase), a discotic phase (including chiral discotic), a discontinuous cubic phase, a hexagonal phase, a bicontinuous cubic phase, a lamellar phase, a reverse hexagonal columnar phase, or an inverse cubic phase. In addition, in certain LCPs of the present disclosure, the LC monomers or residues thereof may transition from one phase to another, for example, in response to thermal energy or actinic radiation.

Examples of polymeric materials include homopolymers and copolymers, prepared from the monomers and mixtures of monomers disclosed in U.S. Pat. No. 5,962,617 and in U.S. Pat. No. 5,658,501 from column 15, line 28 to column 16, line 17, wherein the disclosures of such polymeric materials in these U.S. patents are specifically incorporated herein by reference, an oligomeric material, a monomeric material or a mixture or combination thereof. Polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly (ethylene glycol) bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products. Polymeric materials can also be self-assembled materials.

In specific embodiments, the polymer may be a block or non-block copolymer. In certain embodiments, the block copolymer may comprise hard blocks and soft blocks. In other embodiments, the polymer may be a non-block copolymer (i.e., a copolymer that does not have large blocks of specific monomer residues), such as a random copolymer, an alternating copolymer, periodic copolymers, and statistical copolymers. The present disclosure is also intended to cover copolymers of more than two different types of co-monomer residues.

According to one specific non-limiting embodiment, the organic host material is chosen from polyacrylates, polymethacrylates, poly($C_1$-$C_{12}$) alkyl methacrylates, polyoxy (alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

According to another specific non-limiting embodiment, the organic host material is a homopolymer or copolymer of monomer(s) chosen from acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate. The polymeric material most often comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and/or mixtures thereof.

Further, according to various non-limiting embodiments disclosed herein, the organic host material can form an optical element or portion thereof. Non-limiting examples of optical elements include ophthalmic elements, display elements, windows, and mirrors. As used herein the term "optical" means pertaining to or associated with light and/or vision. For example, although not limiting herein, according to various non-limiting embodiments, the optical element or device can be chosen from ophthalmic elements and devices, display elements and devices, windows, mirrors, packaging material such as shrinkwrap, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

For example, the organic host material can be an ophthalmic element, and more particularly, an ophthalmic lens.

Further, it is contemplated that the photochromic compounds disclosed herein can be used alone or in conjunction with at least one other complementary organic photochromic compound having at least one activated absorption maxima within the range of 300 nm to 1000 nm, inclusive (or substances containing the same). For example, the photochromic compound disclosed herein can be combined with at least one other conventional organic photochromic compound such that the combination of photochromic compound, when activated, exhibits a desired hue. Non-limiting examples of suitable conventional organic photochromic compounds include the pyrans, oxazines, fulgides and fulgimides described hereinafter.

Non-limiting examples of thermally reversible complementary photochromic pyrans include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference for the disclosure of such naphthopyrans; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, the disclosures of which are hereby specifically incorporated by reference. Spiro(indoline)pyrans are also described in the text, *Techniques in Chemistry*, Volume III, "Photochromism", Chapter 3, Glenn H. Brown, Editor, John Wiley and Sons, Inc., New York, 1971, the disclosure of which is hereby incorporated by reference.

Non-limiting examples of thermally reversible complementary photochromic oxazines include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline) naphthoxazines, spiro(indoline)benzoxazines, spiro (indoline)fluoranthenoxazine, and spiro(indoline) quinoxazine.

More non-limiting examples of thermally reversible complementary photochromic fulgides include: fulgimides, and the 3-furyl and 3-thienyl fulgides and fulgimides, which are disclosed in U.S. Pat. No. 4,931,220 (wherein the disclosures of such fulgimides are hereby specifically incorporated by reference) and mixtures of any of the aforementioned photochromic materials/compounds.

For example, it is contemplated that the photochromic compounds disclosed herein can be used alone or in conjunction with another conventional organic photochromic compound (as discussed above), in amounts or ratios such that the organic host material into which the photochromic compounds are incorporated, or onto which the organic host materials are applied, can exhibit a desired color or colors, either in an activated or a "bleached" state. Thus the amount of the photochromic compounds used is not critical provided that a sufficient amount is present to produce a desired photochromic effect. As used herein, the term "photochromic amount" refers to the amount of the photochromic compound necessary to produce the desired photochromic effect.

The present invention also provides a photochromic article comprising a substrate, and an at least partial coating of a coating composition having a photochromic amount of a photochromic compound of the present disclosure connected to at least a portion of at least one surface thereof of the substrate. Further, although not limiting herein, at least a portion of the at least partial coating can be at least partially set. As used herein the term "set" means to fix in a desired orientation.

For example, according to the above-mentioned non-limiting embodiment, the coating composition can be chosen from, without limitation, polymeric coating compositions, paints, and inks. Further, in addition to the photochromic compounds disclosed herein, the coating compositions according to various non-limiting embodiments can further comprise at least one other conventional organic photochromic compounds having at least one activated absorption maxima within the range of 300 nm to 1000 nm, inclusive.

Non-limiting examples of suitable substrates to which the coating composition comprising the photochromic amount of the photochromic compounds can be applied include glass, masonry, textiles, ceramics, metals, wood, paper and polymeric organic materials. Non-limiting examples of suitable polymeric organic materials are set forth above.

Further provided are optical elements comprising a substrate and an at least partial coating comprising at least one photochromic compound of the present disclosure connected to at least a portion of the substrate. Non-limiting examples of optical elements include, ophthalmic elements, display elements, windows, and mirrors. For example, the optical element can be an ophthalmic element, and the substrate can be an ophthalmic substrate chosen from corrective and non-corrective lenses, partially formed lenses, and lens blanks.

Although not limiting herein, the optical elements can comprise any amount of the photochromic compound necessary to achieve the desired optical properties, such as but not limited to, photochromic properties and dichroic properties.

Other non-limiting examples of substrates that are suitable for use in conjunction with the foregoing non-limiting embodiment include untinted substrates, tinted substrates, photochromic substrates, tinted-photochromic substrates, linearly polarizing substrates, circularly polarizing substrates, elliptically polarizing substrates, reflective substrates, and wave plates or retarder substrates, e.g., quarter wave plate and half wave plate. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation (i.e., confine the vibrations of the electric vector of light waves to one direction). As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation and is thermally reversible. Further, as used herein with reference to substrates, the term "tinted-photochromic" means substrates containing a coloring agent addition as well as a photochromic compound, and having an absorption spectrum for visible radiation that varies in response to at least actinic radiation and is thermally reversible. Thus for example, the tinted-photochromic substrate can have a first color characteristic of the coloring agent and a second color characteristic of the combination of the coloring agent and the photochromic compound when exposed to actinic radiation.

The present invention also is directed to an optical element comprising a substrate and an at least partial coating comprising at least one photochromic compound of the present disclosure connected to at least a portion of the substrate. Further, the at least one thermally reversible photochromic compound can be a photochromic-dichroic compound having an average absorption ratio greater than 1.5 in an activated state as determined according to CELL METHOD.

As discussed above, the optical elements according to the present invention can be display elements, such as, but not limited to screens, monitors, and security elements. For example, the optical element can be a display element comprising a first substrate having a first surface, a second substrate having a second surface, wherein the second surface of the second substrate is opposite and spaced apart from the first surface of the first substrate so as to define a gap; and a fluid material comprising at least one photochromic compound of the present disclosure positioned within the gap defined by the first surface of the first substrate and the second surface of the second substrate. Further, the at least one photochromic compound can be a photochromic-dichroic compound having an average absorption ratio greater than 1.5 in an activated state as determined according to CELL METHOD.

Further, according to this non-limiting embodiment, the first and second substrates can be independently chosen from untinted substrates, tinted substrates, photochromic substrates, tinted-photochromic substrates, linearly polarizing substrates, circularly polarizing substrates, elliptically polarizing substrates and reflective substrates and retarder substrates.

The present invention also provides a security element comprising a substrate and at least one photochromic compound of the present disclosure connected to at least a portion of the substrate. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

Although not limiting herein, the security element can be connected to at least a portion of a substrate chosen from a transparent substrate and a reflective substrate. Alternatively, wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing, circularly polarizing substrates, and elliptically polarizing substrates.

Additionally, the at least one photochromic compound can be a thermally reversible photochromic-dichroic compound having an average absorption ratio greater than 1.5 in the activated state as determined according to CELL METHOD.

Furthermore, the aforementioned security element can further comprise one or more other coatings or sheets to form a multi-layer reflective security element with viewing angle dependent characteristics as described in U.S. Pat. No. 6,641,874, which disclosure related to multireflective films is hereby specifically incorporated by reference herein.

The photochromic articles and optical elements described above can be formed by methods known in the art. Although not limiting herein, it is contemplated that the photochromic compounds disclosed herein can be connected to a substrate or host by incorporation into the host material or application onto the host or substrate, such as in the form of a coating.

For example, the photochromic-dichroic compound can be incorporated into an organic host material by dissolving or dispersing the photochromic compound within the host material, e.g., casting it in place by adding the photochromic compound to the monomeric host material prior to polymerization, imbibition of the photochromic compound into the host material by immersion of the host material in a hot solution of the photochromic compound or by thermal transfer. As used herein the term "imbibition" includes permeation of the photochromic compound alone into the host material, solvent assisted transfer of the photochromic compound into a porous polymer, vapor phase transfer, and other such transfer methods.

Additionally, the photochromic compound disclosed herein can be applied to the organic host material or other substrate as part of a coating composition (as discussed above) or a sheet comprising the photochromic compound. As used herein the term "coating" means a supported film derived from a flowable composition, which may or may not have a uniform thickness. As used herein the term "sheet" means a pre-formed film having a generally uniform thickness and capable of self-support. In such cases ultraviolet light absorbers can be admixed with the photochromic materials before their addition to the coating or sheet or such absorbers can be superposed, e.g., superimposed, as a coating or film between the photochromic article and the incident light.

Non-limiting methods of applying coating compositions comprising the photochromic compounds disclosed herein include those methods known in the art for applying coatings, such as, spin coating, spray coating, spray and spin coating, curtain coating, flow coating, dip coating, injection molding, casting, roll coating, wire coating, and overmolding. The coating comprising the photochromic compound can be applied to a mold and the substrate can be formed on top of the coating (i.e., overmolding). Additionally or alternatively, a coating composition without the photochromic compound can be first applied to the substrate or organic host material using any of the aforementioned techniques and thereafter imbibed with the photochromic compound as described above.

Non-limiting examples of coating compositions of film forming polymers that can include photochromic materials are as follows: photochromic/dichroic liquid crystal coatings, such as those described in U.S. Pat. No. 7,256,921 at column 2, line 60 to column 94, line 23; photochromic polyurethane coatings, such as those described in U.S. Pat. No. 6,187,444 at column 3, line 4 to column 12, line 15; photochromic aminoplast resin coatings, such as those described in U.S. Pat. No. 6,432,544 at column 2, line 52 to column 14, line 5 and U.S. Pat. No. 6,506,488 at column 2, line 43 to column 12, line 23; photochromic polysiloxane coatings, such as those described in U.S. Pat. No. 4,556,605 at column 2, line 15 to column 7, line 27; photochromic poly(meth)acrylate coatings, such as those described in U.S. Pat. No. 6,602,603 at column 3, line 15 to column 7, line 50, U.S. Pat. No. 6,150,430 at column 8, lines 15-38, and U.S. Pat. No. 6,025,026 at column 8, line 66 to column 10, line 32; polyanhydride photochromic coatings, such as those described in U.S. Pat. No. 6,436,525 at column 2, line 52 to column 11, line 60; photochromic polyacrylamide coatings such as those described in U.S. Pat. No. 6,060,001 at column 2, line 6 to column 5, line 40; photochromic epoxy resin coatings, such as those described in U.S. Pat. No. 6,268,055 at column 2, line 63 to column 15, line 12; and photochromic poly(urea-urethane) coatings, such as those described in U.S. Pat. No. 6,531,076 at column 2, line 60 to column 10, line 49. The disclosures in the aforementioned U.S. Patents that relate to the film-forming polymers are hereby incorporated herein by reference.

Non-limiting methods of applying sheets comprising the photochromic compound disclosed herein to a substrate include, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet. Further, it is contemplated that the photochromic compound can be applied to the sheet as a coating, incorporated into the sheet by imbibition or by other suitable methods, either prior to applying the sheet to the substrate or thereafter.

The polymeric sheet can comprise a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly(urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric sheet also may comprise functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation e.g., acrylate groups), vinyl groups, and combinations thereof. Appropriate mixtures of film-forming resins may also be used in the preparation of the coating compositions. If the polymer composition from which the polymeric sheet is formed comprises functional group-containing polymers (such as any of the previously mentioned functional group-containing polymers), the polymer composition can further comprise a material having functional groups reactive with those of said polymer. Reaction may be facilitated, for example, by thermal, photoinitiated, oxidative, and/or radiative curing techniques. Also contemplated are mixtures of any of the foregoing polymers.

Further non-limiting examples of polymers suitable for use in forming the polymeric sheet of the present invention are the thermoplastic block copolymers of polyalkyl(meth)acrylate and polyamide described in Published U.S. Patent Application 2004/0068071 A1 at paragraphs [0020]-[0042], the specified portions of which is incorporated by reference herein; and U.S. Pat. No. 6,096,375 at column 18, line 8 to column 19, line 5, the specified portions of which are incorporated by reference herein.

In a particular embodiment of the present invention, the polymeric sheet comprises an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement; and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer".

The elastomeric polymer can comprise any of wide variety of art recognized elastomers including but not limited to copolymers of any of the previously mentioned polymers. In an embodiment of the present invention, the elastomeric polymer can comprise a block copolymer having ether and/or ester linkages in the polymer backbone. Examples of suitable block copolymers can include, but are not limited to, poly(amide-ether) block copolymers, poly(ester-ether) block copolymers, poly(ether-urethane) block copolymers, poly(ester-urethane) block copolymers, and/or poly(ether-urea) block copolymers. Suitable specific examples of such elastomeric polymers can include, but are not limited to, those commercially available under the tradenames DESMOPAN® and TEXIN® from Bayer Material Science; ARNITEL® from Royal DSM; and PEBAX® from Atofina Chemicals or Cordis Corporation.

Moreover, as discussed above, the photochromic compounds disclosed herein can be incorporated or applied alone, or in combination with at least one other conventional organic photochromic compound, which can also be applied or incorporated into the host materials and substrates as described above. Additional coatings may be applied to the photochromic article including other photochromic coatings, anti-reflective coatings, linearly polarizing coatings, transitional coatings, primer coatings, adhesive coatings, mirrored coatings and protective coatings including antifogging coatings, oxygen barrier coatings and ultraviolet light absorbing coatings.

The embodiments described herein are further illustrated by the following non-limiting examples.

EXAMPLES

Part 1 describes the preparation of Examples 1-34. Part 2 describes the testing of the photochromic properties of the Examples. Part 3 describes the testing of the dichroic properties of the Examples.

Part 1—Preparation of Examples 1-34

Example 1

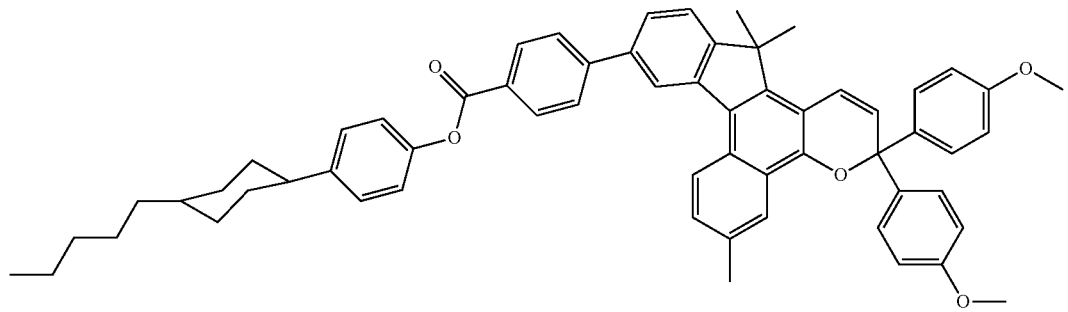 [SMILES: CCCCCC1CCC(c2ccc(OC(=O)c3ccc(-c4ccc5c(c4)-c4c(c6c(c7cc(C)ccc47)OC(c4ccc(OC)cc4)(c4ccc(OC)cc4)C=C6)C5(C)C)cc3)cc2)CC1]

Step 1

3-Bromo-4'-methylbenzophenone (50 g), dimethyl succinate (34.5 g) and toluene (1 liter (L)) were added to a reaction flask equipped with a mechanical stirrer, a solid addition funnel and a nitrogen blanket. The mixture was stirred at room temperature until the solids were dissolved. Solid potassium t-butoxide (22.4 g) was added through the solid addition funnel and the mixture was stirred at room temperature for 4 hours. The resulting reaction mixture was poured into 1 L of water and the aqueous layer, which contained the product, was collected. The toluene layer was extracted with 200 mL water. The combined water solution was washed with toluene. HCl (2 N, 20 mL) was added to the water solution. A yellow oil precipitated. The resulting mixture was extracted with ethyl acetate, dried over magnesium sulfate, concentrated and dried in a vacuum. A yellow glassy oil (55 g) was obtained as product. It was used directly in the next step.

Step 2

A mixture of the Stobbe acid products from Step 1 (55 g) and acetic anhydride (300 mL) was mixed and refluxed in a reaction flask equipped with a condenser. After one hour, the acetic anhydride was removed by vacuum evaporation and 55 grams of oil was obtained as the product. It was used directly in the next step.

Step 3

To a reaction flask containing the 55 grams of oil obtained from Step 2 was added methanol (300 mL) of and HCl (12 N, 1 ml). The mixture was refluxed for four hours. Methanol was removed by vacuum evaporation. The recovered oil was dissolved in methylene chloride, washed with sodium bicarbonate saturated water, dried over magnesium sulfate, concentrated and dried in vacuum. The resulting oil (51 g) was used directly in the next step.

Step 4

The product (51 g) from Step 3 was dissolved in 500 ml of anhydrous THF in an oven dried flask equipped with a dropping funnel and a magnetic stir bar. The mixture was stirred mixture at room temperature, and 1.6 M toluene/THF (1:1) solution of methyl magnesium bromide was added dropwise. After the addition, the mixture was stirred at room temperature for about 16 hours. The reaction mixture was then poured into 2 L of ice water. The pH value of the mixture was adjusted to ~2 using HCl (12 N). Ethyl acetate (500 mL) was added. The resulting organic layer was separated, dried over magnesium sulfate, concentrated and dried in vacuum. The recovered product (50 g of oil) was used directly in the next step.

Step 5

The product from Step 4 (50 g) and xylene (300 mL) were added to a reaction flask equipped with a magnetic stir bar. p-Toluenesulfonic acid (1 g) was added and the resulting mixture was refluxed for eight hours. Xylene was removed by vacuum evaporation and the resulting oily product was dissolved in ethyl acetate, washed with water, dried over magnesium sulfate and concentrated. A small portion of the product (50 g of oil) contained four naphthol isomers. The product (1.8 g) was purified using a CombiFlash® Rf from Teledyne ISCO. After separation, four grouped fractions were obtained. NMR analysis showed the products to have structures consistent with: 8-bromo-3,7,7-trimethyl-7H-benzo[c]fluoren-8-ol (0.32 g); 4-bromo-7,7,9-trimethyl-7H-benzo[c]fluoren-5-ol (0.08 g); and a mixture (0.36 g) of 10-bromo-3,7,7-trimethyl-7H-benzo[c]fluoren-5-ol (the desired isomer, being 55 weight % of the mixture) and 2-bromo-7,7,9-trimethyl-7H-benzo[c]fluoren-5-ol (the undesired isomer being 45 weight % of the mixture).

Step 6

The mixture of naphthols from Step 5, (0.36 g) of 10-bromo-3,7,7-trimethyl-7H-benzo[c]fluoren-5-ol and 2-bromo-7,7,9-trimethyl-7H-benzo[c]fluoren-5-ol was placed in a reaction flask. To the flask was added 0.27 grams of 1,1-bis(4-methoxyphenyl)prop-2-yn-1-ol, a few crystals of p-toluenesulfonic acid and methylene chloride (10 ml). The mixture was stirred at room temperature for 18 hours. The formation of a blue dye and a purple dye was observed from TLC. The product was purified using a CombiFlash® Rf. A product (0.5 g) with two isomers was obtained. It was used directly in the next step.

Step 7

The dye mixture from Step 6 (0.5 g) was placed in a reaction flask and the following were added: 4-(4-trans-pentylcyclohexyl)phenyl 4-(4,4,5,5-tetramethyl-1,3,2-dioxaborolan-2-yl)benzoate (0.39 g, prepared following the procedure from Step 2 of Example 3 except that 4-(trans-4-pentylcyclohexyl)phenol and 4-(4,4,5,5-tetramethyl-1,3,2-dioxaborolan-2-yl)benzoic acid was used in place of 4-(4,4,5,5-tetramethyl-1,3,2-dioxaborolan-2-yl)aniline and 4-(trans-4 pentylcyclohexyl)benzoic acid); potassium fluoride (0.19 g); dichlorobis(triphenylphosphine)palladium (II) (0.012 g); THF (20 mL) and water (20 mL). The mixture was degassed, protected by nitrogen and heated to reflux. After 18 hours, TLC showed the formation of a grey dye and a purple dye. The mixture was extracted using methylene chloride and water. The organic layer was recovered, isolated, dried over magnesium sulfate and concentrated. The resulting product was purified using CombiFlash®Rf. The grey dye was obtained as a green solid (0.25 g, less polar). The purple dye was obtained as an off-white solid (0.18 g, more polar). NMR analysis showed the more polar purple dye to have a structure consistent with 3,3-bis(4-methoxyphenyl)-10-[4-((4-(trans-4-pentylcyclohexyl)phenoxy)carbonyl)phenyl]-6,13,13-trimethyl-3,13-dihydro-indeno[2',3':3,4]naphtho[1,2-b]pyran.

Example 2

Step 1

Magnesium (3.2 g) and THF (50 ml) was placed in a dry flask equipped with a dropping funnel which contained a mixture of 1-bromo-4-(trifluoromethyl)benzene (30 g) and THF (200 ml). 20 ml of the solution in the dropping funnel was added to the flask. A few drops of dibromoethane were also added to the flask to help initiate the reaction. Few minutes later, solvent in the reaction flask started to boil. Rest of the solution in the dropping funnel was added drop wise. Ice water was used occasionally to cool the reaction mixture. After the addition, the mixture was stirred at room temperature for two hours. 3-bromo-4-methylbenzonitrile (26 g) was then added to the reaction mixture. Mixture was stirred at room temperature over night. 3 N HCl (200 ml) was added. The mixture was stirred for 4 hours. Organic layer was collected by a seperatory funnel and then concentrated. A silica gel plug column separation was used to clean up the product with the use of mixture solvent 90/10 Hexanes/ethyl acetate. The type of silica gel used in this step and others was Grade 60, 230-400 mesh. White crystals (19 g) were obtained as the product. NMR showed that the product had a structure consistent with 3-bromo-4-methyl-4'-trifluoromethylbenzophenone.

Step 2

A suspension of 1-bromo-4-(trans-4-pentylcyclohexyl)benzene (96 g), 4-(methoxycarbonyl)phenylboronic acid (56 g), $K_2CO_3$ (17 g), $Pd(Pph_3)_4$ (1.5 g), 1,4-dioxane (400 mL) and water (12 mL) was placed in a reaction flask and stirred at 105□ for 10 hours. After the reaction, the mixture was poured into water (1 L) under stirring. Grey solid was obtained after filtration. The solid was washed with water, dissolved in $CH_2Cl_2$ (400 mL), dried over $MgSO_4$ and filtered through celite. The filtrate was concentrated and poured into methanol (600 mL) under stirring. The precipitate was collected by filtration, washed with methanol and dried. White solid was obtained (80.4 g) as product. NMR showed that the product had a structure consistent with methyl 4'-(4-pentylcyclohexyl)biphenyl-4-carboxylate.

Step 3

Product from Step 2 (20 g) was mixed with sodium hydroxide (6.57 g) and ethanol (500 mL) in a reaction flask. The mixture was heated to reflux for 4 hours, cooled to room temperature and acidified using conc. HCl. The precipitate was collected by filtration, washed with water and dried. White solid was obtained (18.2 g) as product. NMR showed that the product had a structure consistent with 4'-(4-pentylcyclohexyl)biphenyl-4-carboxylic acid.

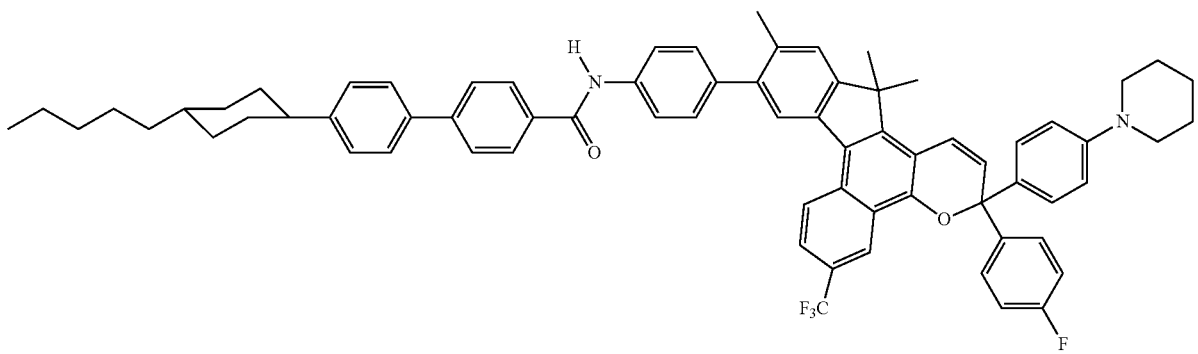 [SMILES: CCCCCC1CCC(c2ccc(-c3ccc(C(=O)Nc4ccc(-c5cc6c(cc5C)C(C)(C)c5c7c(c8cc(C(F)(F)F)ccc8c5-6)OC(c5ccc(F)cc5)(c5ccc(N6CCCCC6)cc5)C=C7)cc4)cc3)cc2)CC1]

Step 4

Product from Step 3 (18.2 g) was mixed with SOCl$_2$ (300 mL) and DMF (three drops) in a reaction flask and heated to reflux for 8 hours. The solution was concentrated under atmospheric pressure and the resulting residue was poured into 200 mL hexane under stirring. The precipitated white solid was collected by filtration, washed with hexane and dried. White solid (17.53 g) was obtained as product. NMR showed that the product had a structure consistent 4'-(4-pentylcyclohexyl) biphenyl-4-carbonyl chloride.

Step 5

Product from Step 4 (10 g) in methylene chloride (30 ml) was dropped into a solution of 4-(4,4,5,5-tetramethyl-1,3,2-dioxaborolan-2-yl)aniline (5.94 g) and TEA (4.13 g) in CH$_2$Cl$_2$ (60 ml) under stirring. After addition, the solution was kept stirring for 24 hours. The solution was then washed with water (50 mL) three times, dried over MgSO$_4$, concentrated under reduced pressure and then poured into methanol (200 ml) under stirring. The precipitate was filtered, washed with methanol and dried. White solid (12.24 g) was obtained as product. NMR showed that the product had a structure consistent with 4'-(4-pentylcyclohexyl)-N-(4-(4,4,5,5-tetramethyl-1,3,2-dioxaborolan-2-yl)phenyl)biphenyl-4-carboxamide.

Step 6

The procedures from Step 1 to Step 7 of Example 1 were followed except that 3-bromo-4-methyl-4'-trifluoromethylbenzophenone from step 1 of this example was used in place of 3-bromo-4'-methylbenzophenone in Step 1 of Example 1, 1-(4-fluorophenyl)-1-(4-(piperidin-1-yl)phenyl)prop-2-yn-1-ol was used in place of 1,1-bis(4-methoxyphenyl)prop-2-yn-1-ol in Step 6 of Example 1 and 4'-(4-trans-pentylcyclohexyl)-N-(4-(4,4,5,5-tetramethyl-1,3,2-dioxaborolan-2-yl)phenyl)-[1,1-biphenyl]-4-carboxamide from step 5 of this example was used in place of 4-(4-trans-pentylcyclohexyl) phenyl 4-(4,4,5,5-tetramethyl-1,3,2-dioxaborolan-2-yl)benzoate in Step 7 of Example 1. Blue solid was obtained as the product. NMR showed that the product had a structure consistent with 3-(4-fluorophenyl)-3-(4-piperidinophenyl)-10-[4-(4-(4-trans-pentylcyclohexyl)phenyl)benzamido)phenyl]-6-trifluoromethyl-11,13,13-trimethyl-3,13-dihydro-indeno[2',3':3,4]naphtho[1,2-b]pyran.

Example 3

Step 1

Magnesium (5.26 g) and THF (50 ml) was placed in a dry flask equipped with a dropping funnel, which contained THF (400 ml) solution of 1-bromo-3,5-difluorobenzene (44 g). One tenth of the solution in the dropping funnel was added to the flask. A few drops of dibromoethane were also added to the flask to help initiate the reaction. Few minutes later, solvent in the reaction flask started to boil. Ice bath was applied. Rest of the solution in the dropping funnel was added drop wise at 0° C. in half an hour. Half an hour after the addition, most Mg disappeared. Mixture was let stir at room temperature for 2 more hours. All Mg went into solution. At 0° C., bis[2-(N,N-dimethylamino)ethyl]ether (35 g) was added. Stir for 15 minutes. Then 3-bromobenzoyl chloride (50 g) was added in one portion. Mixture was stirred for 2 hours at 0° C. water (500 mL) was added to the mixture. 12N HCl was used to adjust pH to ~2. DCM was added to the mixture (500 ml). Organic layer was collected, washed with water once, washed with sodium bicarbonate once, dried over magnesium sulfate and concentrated. A viscous oil (57 g) was obtained. The oil was used directly in the next step. NMR showed that 3-bromo-3',5'-difluorobenzophenone was the major component in the oil.

Step 2

A mixture of 4-(4,4,5,5-tetramethyl-1,3,2-dioxaborolan-2-yl)aniline (52 g), 4-(trans-4-pentylcyclohexyl)benzoic acid (65 g), DCC (64.4 g), DMAP (3 g) and methylene chloride (500 ml) was placed in a reaction flask and stirred for 24 hours. Solid was filtered off. The filtrate was concentrated. Methanol (1 L) was added. The formed crystals were collected by filtration and dried. White crystals (91 g) were obtained as the product. NMR showed that the product had a structure consistent with 4-(4-trans-pentylcyclohexyl)-N-(4-(4,4,5,5-tetramethyl-1,3,2-dioxaborolan-2-yl)phenyl)benzamide.

Step 3

The procedures from Step 1 to Step 7 of Example 1 were followed except that 3-bromo-3',5'-difluorobenzophenone from Step 1 of this example was used in place of 3-bromo-4'-methylbenzophenone in Step 1 of Example 1, and 4-(4-trans-pentylcyclohexyl)-N-(4-(4,4,5,5-tetramethyl-1,3,2-dioxaborolan-2-yl)phenyl)benzamide from Step 2 of this example was used in place of 4-(4-trans-pentylcyclohexyl) phenyl 4-(4,4,5,5-tetramethyl-1,3,2-dioxaborolan-2-yl)benzoate in Step 7 of Example 1. Grey solid was obtained as the product. NMR showed that the product had a structure consistent with 3,3-bis(4-methoxyphenyl)-10-[4-(4-(4-trans-pentylcyclohexyl)benzamido)phenyl]-5,7-difluoro-13,13-dimethyl-3,13-dihydro-indeno[2',3':3,4]naphtho[1,2-b] pyran.

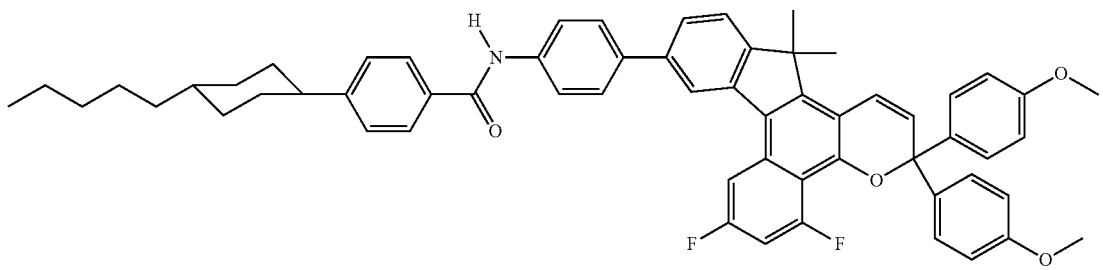 [SMILES: CCCCCC1CCC(c2ccc(C(=O)Nc3ccc(-c4ccc5c(c4)-c4c(c6c(c7c(F)cc(F)cc47)OC(c4ccc(OC)cc4)(c4ccc(OC)cc4)C=C6)C5(C)C)cc3)cc2)CC1]

Example 4

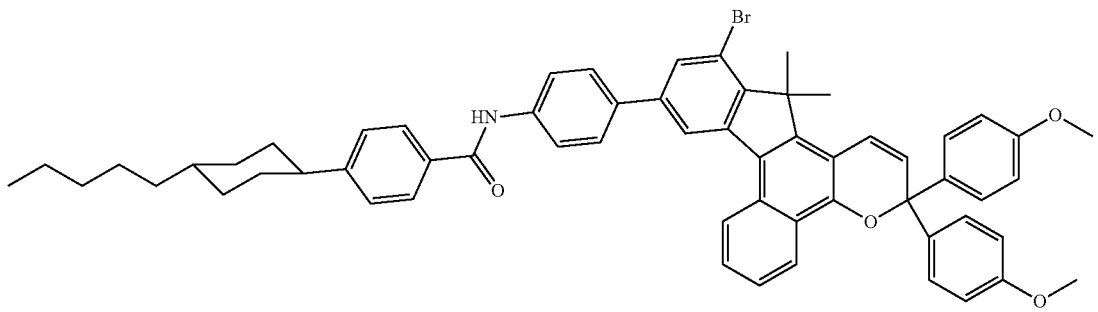 [SMILES: CCCCCC1CCC(c2ccc(C(=O)Nc3ccc(-c4cc(Br)c5c(c4)-c4c(c6c(c7ccccc47)OC(c4ccc(OC)cc4)(c4ccc(OC)cc4)C=C6)C5(C)C)cc3)cc2)CC1]

The procedures from Example 3 were followed except that in Step 1, tribromobenzene was used in place of 1-bromo-3,5-difluorobenzene and benzoyl chloride was used in place of 3-bromobenzoyl chloride. Black solid was obtained as the product. NMR analysis showed that the product had a structure consistent with 3,3-bis(4-methoxyphenyl)-10-[4-(4-(4-trans-pentylcyclohexyl)benzamido)phenyl]-13,13-dimethyl-12-bromo-3,13-dihydro-indeno[2',3':3,4]naphtho[1,2-b]pyran.

Example 5

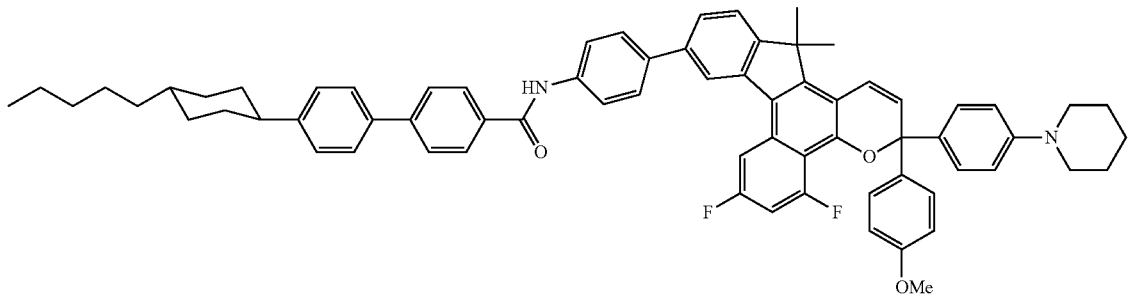 [SMILES: CCCCCC1CCC(c2ccc(-c3ccc(C(=O)Nc4ccc(-c5ccc6c(c5)-c5c(c7c(c8c(F)cc(F)cc58)OC(c5ccc(OC)cc5)(c5ccc(N8CCCCC8)cc5)C=C7)C6(C)C)cc4)cc3)cc2)CC1]

The procedures from Example 1 were followed except that 3-bromo-3',5'-difluorobenzophenone from Step 1 of Example 3 was used in place of 3-bromo-4'-methylbenzophenone in Step 1, 1-(4-methoxyphenyl)-1-(4-(N-piperidino)phenyl)prop-2-yn-1-ol was used in place of 1,1-bis(4-methoxyphenyl)prop-2-yn-1-ol in step 6 and 4'-(4-trans-pentylcyclohexyl)-N-(4-(4,4,5,5-tetramethyl-1,3,2-dioxaborolan-2-yl)phenyl)-[1,1'-biphenyl]-4-carboxamide was used in place of 4-(4-trans-pentylcyclohexyl)-N-(4-(4,4,5,5-tetramethyl-1,3,2-dioxaborolan-2-yl)phenyl)benzamide in step 7. NMR analysis showed that the product had a structure consistent with 3-(4-methoxyphenyl)-3-(4-(N-piperidino)phenyl)-10-[4-(4-(4-(4-trans-pentylcyclohexyl)phenyl)benzamido)phenyl]-5,7-difluoro-13,13-dimethyl-3,13-dihydro-indeno[2',3':3,4]naphtho[1,2-b]pyran.

Example 6

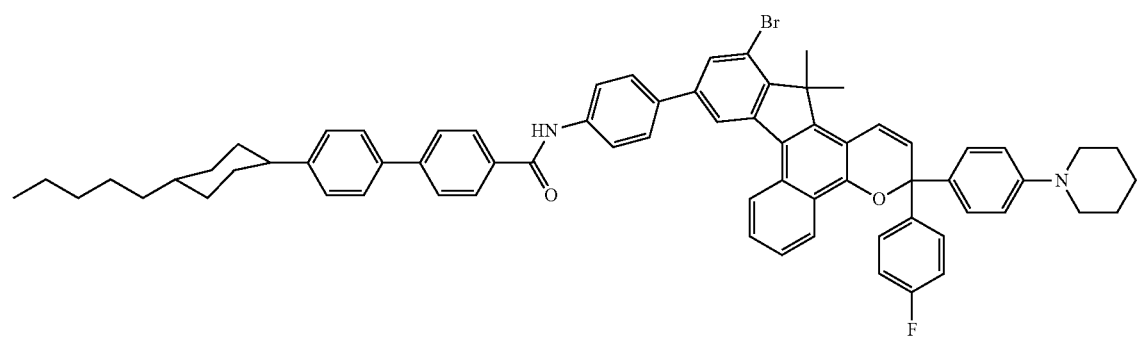 [SMILES: CCCCCC1CCC(c2ccc(-c3ccc(C(=O)Nc4ccc(-c5cc(Br)c6c(c5)-c5c(c7c(c8ccccc58)OC(c5ccc(F)cc5)(c5ccc(N8CCCCC8)cc5)C=C7)C6(C)C)cc4)cc3)cc2)CC1]

The procedures from Step 1 and Step 3 of Example 3 were followed except that: in Step 1, tribromobenzene was used in place of 1-bromo-3,5-difluorobenzene and benzoyl chloride was used in place of 3-bromobenzoyl chloride; in Step 3,1-(4-fluorophenyl)-1-(4-(N-piperidino)phenyl)prop-2-yn-1-ol was used in place of 1,1-bis(4-methoxyphenyl)prop-2-yn-1-ol; 4'-(4-trans-pentylcyclohexyl)-N-(4-(4,4,5,5-tetramethyl-1,3,2-dioxaborolan-2-yl)phenyl)-[1,1'-biphenyl]-4-carboxamide was used in place of 4-(4-trans-pentylcyclohexyl)-N-(4-(4,4,5,5-tetramethyl-1,3,2-dioxaborolan-2-yl)phenyl)benzamide. NMR analysis showed that the product had a structure consistent with 3-(4-fluorophenyl)-344-(N-piperidino)phenyl)-10-[4-(4-(4-(4-trans-pentylcyclohexyl)phenyl)benzamido)phenyl]-12-bromo-13,13-dimethyl-3,13-dihydro-indeno[2',3':3,4]naphtho[1,2-b]pyran.

Example 7

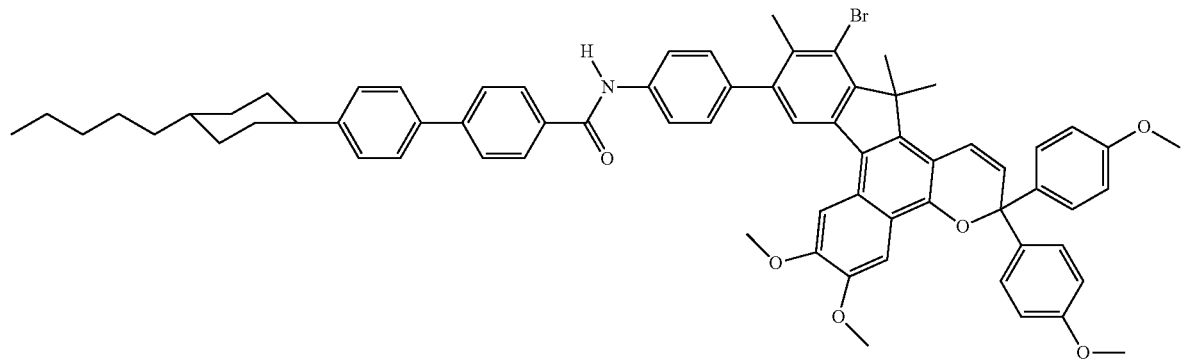 [SMILES: CCCCCC1CCC(c2ccc(-c3ccc(C(=O)Nc4ccc(-c5cc6c(c(Br)c5C)C(C)(C)c5c7c(c8cc(OC)c(OC)cc8c5-6)OC(c5ccc(OC)cc5)(c5ccc(OC)cc5)C=C7)cc4)cc3)cc2)CC1]

The procedures from Step 1 and Step 3 of Example 3 were followed except that: in Step 1,2,4,6-tribromotoluene was used in place of 1-bromo-3,5-difluorobenzene and 3,4-dimethoxybenzoyl chloride was used in place of 3-bromobenzoyl chloride; in Step 3,4'-(4-trans-pentylcyclohexyl)-N-(4-(4,4,5,5-tetramethyl-1,3,2-dioxaborolan-2-yl)phenyl)-[1,1'-biphenyl]-4-carboxamide was used in place of 4-(4-trans-pentylcyclohexyl)-N-(4-(4,4,5,5-tetramethyl-1,3,2-dioxaborolan-2-yl)phenyl)benzamide. NMR analysis showed that the product had a structure consistent with 3,3-bis(4-methoxyphenyl)-10-[4-(4-(4-(4-trans-pentylcyclohexyl)phenyl)benzamido)phenyl]-12-bromo-6,7-dimethoxy-11,13,13-trimethyl-3,13-dihydro-indeno[2',3':3,4]naphtho[1,2-b]pyran.

Example 8

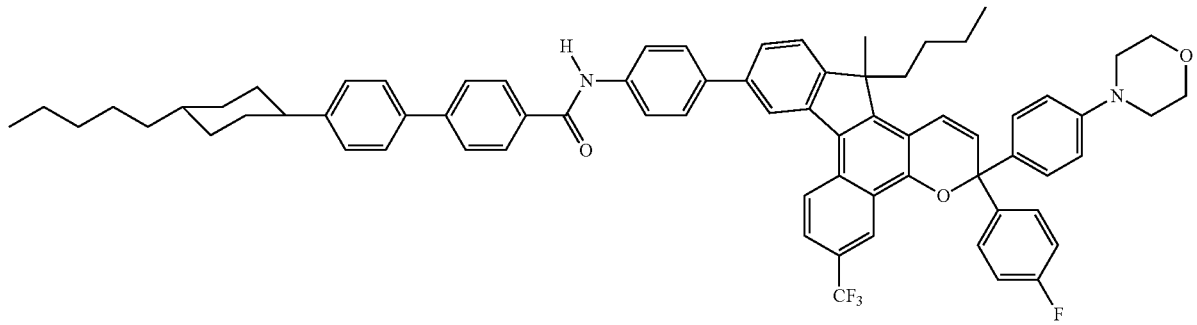 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(F)cc5)(c5ccc(N8CCOCC8)cc5)C=C7)C6(C)CCCC)cc4)cc3)cc2)CC1]

Step 1

A mixture of 4-bromoacetophenone (148 g), dimethyl succinic ester (130 g) and toluene (2.5 L) was mechanically stirred in a reaction flask. Potassium t-butoxide (100 g) was added in one portion. A yellow color was observed. A lot of precipitate was formed. One hour later, water (1 L) was added. Water layer was collected and washed with toluene twice. It was then neutralized by 12 N HCl. The product was extracted out by ethyl acetate and then recrystallized from ethyl ether/hexanes. 170 g white crystals were obtained. NMR analysis showed that the product had a structure consistent with (E)-4-(4-bromophenyl)-3-(methoxycarbonyl)pent-3-enoic acid.

Step 2

(E)-4-(4-bromophenyl)-3-(methoxycarbonyl)pent-3-enoic acid (160 g) from Step 1 was mixed with 50% sodium hydroxide water solution (200 g) and water (4 liters) in a four liter beaker. The mixture was heated to boil. One hour later, TLC showed that reaction was completed. The pH of the solution was adjusted to 2 using 12 N HCl. The precipitate was collected by filtration. Off-white crystals (152 grams) were obtained. NMR analysis showed that the product had a structure consistent with (E)-2-(1-(4-bromophenyl)ethylidene)succinic acid.

Step 3

A mixture of (E)-2-(1-(4-bromophenyl)ethylidene)succinic acid (152 g) from Step 2, DBSA (5 g) and toluene (1 L) was heated up to reflux with water removal by a Dean-Stark trap. Solid starting material eventually disappeared in one hour. After 2 hours, TLC showed that the reaction was completed. Mixture was passed through a silica gel plug column. Product was washed off plug column with ¼ ethyl acetate/hexanes. After concentration, oil was obtained: To the oil, hexanes (1 L) was added. Product crystallized out. It was collected by filtration and dried in vacuum. Off-white crystals (130 grams) were obtained. NMR analysis showed that the product had a structure consistent with (E)-3-(1-(4-bromophenyl)ethylidene)dihydrofuran-2,5-dione.

Step 4

To a stirred mixture of the aluminum chloride (130 g) and methylene chloride (1 L), (E)-3-(1-(4-bromophenyl)ethylidene)dihydrofuran-2,5-dione (125 g) from Step 3 was added in three portions in 5 minutes. Mixture turned dark. After stirring at room temperature for 2 hours, the reaction mixture was poured into water (2 L) slowly. Smoke generation was observed. A large amount of yellow solid was formed. THF (1 L) was added to the mixture to dissolve the yellow solid. The water layer was saturated with solid NaCl and then removed by a separatory funnel. The organic solution was dried over magnesium sulfate and concentrated to viscous. Ethyl acetate (200 ml) was added and the mixture was let sitting at room temperature. Yellow crystals crashed out and were collected and dried (50 grams). NMR analysis showed that the product had a structure consistent with 2-(6-bromo-3-methyl-1-oxo-1H-inden-2-yl)acetic acid.

Step 5

A mixture of manganese chloride (7.46 g) and lithium chloride (5 g) was dried at 200° C. in a vacuum oven for an hour. Under the protection of nitrogen, THF was added (200 ml). The dissolution took about 30 minutes. To the solution, copper (I) chloride (0.59 g) and 2-(6-bromo-3-methyl-1-oxo-1H-inden-2-yl)acetic acid (19.4 g) from Step 4 was added. The mixture was stirred to clear and then cooled to 0° C. To the mixture, 2M THF solution of butylmagnesium bromide (99 ml) was added dropwise. The reaction mixture turned black eventually with the addition of more BuMgBr. The addition was finished in 2 hours. After the addition, the mixture was stirred at 0° C. for 2 more hours and then quenched using water (200 ml). The pH of the mixture was adjusted to ~2 using 12 N HCl. Ethyl acetate (200 ml) was added. The organic portion was collected by a separatory funnel, dried, and concentrated. The product was purified by CombiFlash®. Rf Oil (4 g) was obtained as the product. NMR analysis showed that the product had a structure consistent with 2-(5-bromo-1-butyl-1-methyl-3-oxo-2,3-dihydro-1H-inden-2-yl)acetic acid.

Step 6

Solid magnesium (1.5 g) was placed in a reaction flask equipped with a dropping funnel and dried in an oven. THF (60 ml) and 1-bromo-4-trifluoromethylbenzene (15.3 g) was added. With the initiation of one drop of 1,2-dibromoethane, Grignard started to form. Ice bath was used occasionally to control the rate of the reaction. Two hours later, all magnesium was gone. In the dropping funnel, 2-(5-bromo-1-butyl-1-methyl-3-oxo-2,3-dihydro-1H-inden-2-yl)acetic acid (4.2 g) from Step 5 was mixed with anhydrous THF (20 ml) and dropped into the Grignard solution. The addition was completed in 10 minutes. After the addition, the mixture was stirred at room temperature for 2 hours. The reaction was stopped by the addition of water (100 ml). The pH was adjusted to 2 using 12 N HCl. Ethyl acetate was added (100 ml). The organic phase was collected by a separatory funnel, washed with NaCl/water, dried over magnesium sulfate and concentrated. The obtained oil was re-dissolved in toluene (100 ml) in a reaction flask. Acetic anhydride (10 grams) and bismuth triflate (0.5 g) was added. The mixture was refluxed for 1 hour and cooled to room temperature. Methanol (100 ml) and 12 N HCl (1 ml) was added. The mixture was refluxed for 12 hours. All the solvent was removed. A silica gel plug column separation was applied to the product. Oil (3 g) was obtained as the product.

NMR analysis supported that the product had a structure consistent with 10-bromo-7-butyl-7-methyl-3-(trifluoromethyl)-7H-benzo[c]fluoren-5-ol.

Step 7

The 10-bromo-7-butyl-7-methyl-3-(trifluoromethyl)-7H-benzo[c]fluoren-5-ol (3 g) from Step 6 was placed in a reaction flask. To the flask, 1-(4-fluorophenyl)-1-(4-(N-morpholino)phenyl)prop-2-yn-1-ol (2.1 g), 1,2-dichloroethane (30 ml) and p-toluenesulfonic acid (70 mg) was added. The mixture was refluxed for 4 hours. All solvent was removed. A silica gel plug column was used to purify the product. A brownish oil (2 grams) was obtained as the product. NMR analysis showed that the product had a structure consistent with 3-(4-fluorophenyl)-3-(4-(N-morpholino)phenyl)-10-bromo-6-trifluoromethyl-13-methyl-13-butyl-3,13-dihydro-indeno[2',3':3,4]naphtho[1,2-b]pyran.

Step 8

A mixture of 3-(4-fluorophenyl)-3-(4-(N-morpholino)phenyl)-10-bromo-6-trifluoromethyl-13-methyl-13-butyl-indeno[2',3':3,4]naphtho[1,2-b]pyran (1.4 g) from Step 7, 4'-(4-trans-pentylcyclohexyl)-N-(4-(4,4,5,5-tetramethyl-1,3,2-dioxaborolan-2-yl)phenyl)-[1,1'-biphenyl]-4-carboxamide (1.5 g), palladium acetate (24 mg), triphenyl phosphine (112 mg), sodium carbonate (0.8 g), THF (20 ml) and water (10 ml) was degassed and refluxed for 4 hours. The reaction mixture was passed through CELITE® filtering aid elite to get rid of the insoluble solid in the mixture. The product was washed off using methylene chloride. After extraction with water, organic layer was collected and concentrated. The product was purified by CombiFlash® Rf. Blue solid (0.7 g) was obtained as the product. NMR showed that the product had a structure consistent with 3-(4-fluorophenyl)-3-(4-(N-morpholino)phenyl)-10-[4-(4-(4-(4-trans-pentylcyclohexyl)phenyl)benzamido)phenyl]-6-trifluoromethyl-13-methyl-13-butyl-3,13-dihydro-indeno[2',3':3,4]naphtho[1,2-b]pyran.

Example 9

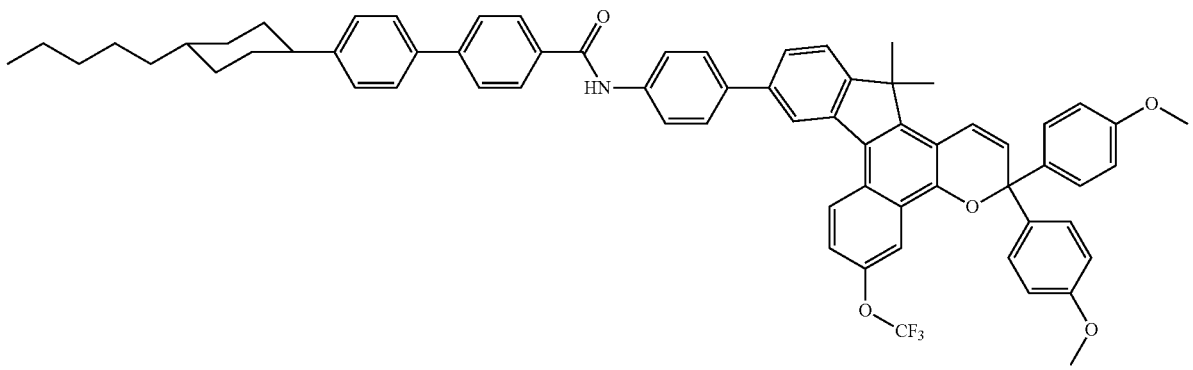 [SMILES: CCCCCC1CCC(c2ccc(-c3ccc(C(=O)Nc4ccc(-c5ccc6c(c5)-c5c(c7c(c8cc(OC(F)(F)F)ccc58)OC(c5ccc(OC)cc5)(c5ccc(OC)cc5)C=C7)C6(C)C)cc4)cc3)cc2)CC1]

The procedures from Example 8 were followed except that: in Step 5, 1.4 M THF solution of methyl magnesium bromide was used in place of butyl magnesium bromide; in Step 6,1-bromo-4-trifluoromethoxybenzene was used in place of 1-bromo-4-trifluoromethylbenzene; in Step 7,1,1-bis(4-methoxyphenyl)prop-2-yn-1-ol was used in place of 1-(4-fluorophenyl)-1-(4-(N-morpholino)phenyl)prop-2-yn-1-ol. NMR analysis showed that the product had a structure consistent with 3,3-bis(4-methoxyphenyl)-10-[4-(4-(4-(4-trans-pentylcyclohexyl)phenyl)benzamido)phenyl]-6-trifluoromethoxy-13-methyl-13-butyl-3,13-dihydro-indeno[2',3':3,4]naphtho[1,2-b]pyran.

Example 10

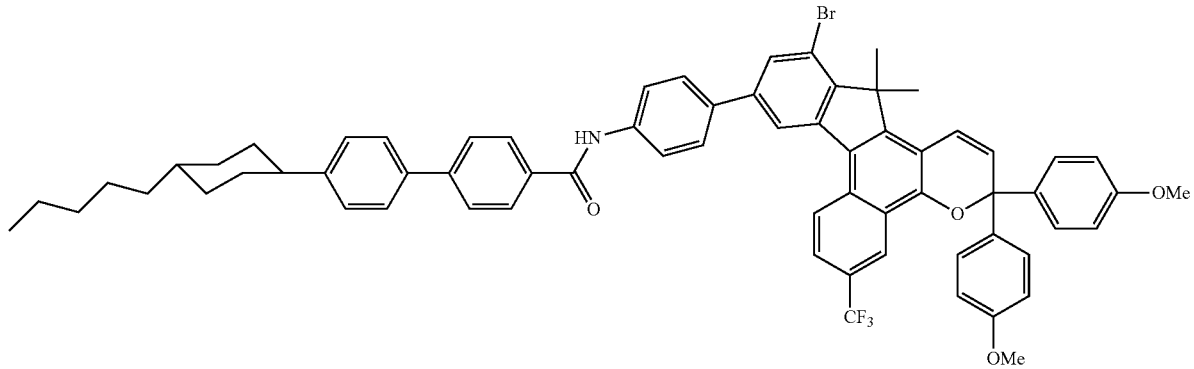 [SMILES: CCCCCC1CCC(c2ccc(-c3ccc(C(=O)Nc4ccc(-c5cc(Br)c6c(c5)-c5c(c7c(c8cc(C(F)(F)F)ccc58)OC(c5ccc(OC)cc5)(c5ccc(OC)cc5)C=C7)C6(C)C)cc4)cc3)cc2)CC1]

Step 1

A 2 L flask with tribromobenzene (100 g) and a magnetic stir bar was dried in a vacuum oven at 80° C. for 4 hours. Dry THF (500 ml) was added. The resulting mixture was placed in an NaCl saturated ice bath. 3M Isopropyl magnesium chloride (160 ml) was added drop wise to the solution at a rate so that the inside temperature was controlled to −20 to 0° C. The addition was finished in about 30 minutes to 1 hour. The mixture was stirred for half an hour at the same temperature and bis[2-(N,N-dimethylamino)ethyl]ether (61 g) was added slowly over a 5 minutes interval and a large amount of precipitate formed. The resulting mixture was stirred for 20 more minutes and a mixture of 4-trifluoromethylbenzoyl chloride (73 g) and THF (100 ml) was added over a 5 minute interval. The resulting mixture was stirred overnight. Water (100 ml) was added slowly and the pH was adjusted to 2 with 3N HCl. The organic layer was collected by a separatory funnel, washed with 5% NaOH/water and NaCl/water, dried and concentrated. To the recovered oil, methanol (300 ml) was added and the product crystallized. The product was collected by filtration. NMR showed that the obtained white crystals (87 g) have a structure consistent with 3,5-dibromo-4'-trifluoromethylbenzophenone.

Step 2

A mixture of 3,5-dibromo-4'-trifluoromethylbenzophenone (75 g) from Step 1, dimethyl succinic ester (32.2 g) and toluene (800 ml) were placed in a three neck 5 L flask equipped with a mechanical stir. Solid of potassium t-butoxide (22.6 g) was added batchwise over a 30 minute interval. An exothermic reaction along with the formation of a large amount of precipitate was observed. After two hours, water (500 ml) was added and a milky mixture was obtained. The pH of the mixture was adjusted to ~2 using 3 N HCl. After stirring at room temperature for 10 minutes, the organic layer was collected, washed with NaCl/HCl, dried over MgSO4. After concentration, hexanes were added and white crystals formed. The crystals were collected by filtration. NMR showed that the obtained product (62 grams) had a structure consistent with (E)-4-(3,5-dibromophenyl)-3-(methoxycarbonyl)-4-(4-(trifluoromethyl)phenyl)but-3-enoic acid.

Step 3

Solid anhydrous lanthanum (III) chloride (100 g) was ground to a very fine powder and then mixed with lithium chloride (52 g) and dry THF (1 liter) in a 5 liter three-neck flask equipped with a mechanical stir and a dropping funnel. The mixture was refluxed for few hours until it dissolved. Solid (E)-4-(3,5-dibromophenyl)-3-(methoxycarbonyl)-4-(4-(trifluoromethyl)phenyl)but-3-enoic acid (106 g) from Step 2 was dissolved in the mixture. The mixture was then cooled to −15° C. A solution of 3M methyl magnesium chloride (238 ml) was placed in the dropping funnel. The first 30% of the Grignard was added slowly to the mixture. Generation of gas bubbles was observed. After the temperature returned to −15° C., the remainder of the Grignard was added to the mixture in 2 minutes. After 30 minutes, water (1 L) was added slowly to the mixture and the pH was adjusted to acidic using acetic acid. The mixture turned clear with formation of two layers. Water layer was drained off. Organic layer was washed with NaCl/water four times and then concentrated to dry. A light yellowish solid was recovered and dissolved in toluene. The solution was filtered using a silica gel plug column and the recovered clear solution was concentrated to dryness. White solid product was obtained and used in the next Step without further purification. A portion of the product was recrystallized from methanol and NMR analysis showed that the purified crystals had a structure consistent with (E)-4-((3,5-dibromophenyl)(4-(trifluoromethyl)phenyl)methylene)-5,5-dimethyldihydrofuran-2(3H)-one.

Step 4

Into a reaction flask was added the product from Step 3, toluene (500 ml), bismuth triflate (20 g) and acetic acid (0.24 g). The resulting mixture was stirred at reflux for 1 hour. After it cooled to room temperature, acetic anhydride (100 ml) was added. The mixture was heated to reflux again and after one hour, the mixture was cooled to room temperature and filtered through a silica gel plug column. The recovered clear solution was concentrated to dryness. Acetone (50 ml) was added to the obtained solid to form a slurry and methanol (250 ml) was subsequently added. The resulting mixture was cooled to form crystals. The recovered white crystals (58 g) were analyzed by NMR which showed that the product had a structure consistent with 8,10-dibromo-7,7-dimethyl-3-(trifluoromethyl)-7H-benzo[c]fluoren-5-yl acetate.

Step 5

To a flask containing 8,10-dibromo-7,7-dimethyl-3-(trifluoromethyl)-7H-benzo[c]fluoren-5-yl acetate (2.42 g) from Step 4 was added methanol (20 mL) and tetrahydrofuran (10 mL). Concentrated hydrochloric acid (1 mL) was added and the solution was heated to reflux for 4 h. The solvent was removed under vacuum and the residue was purified by filtration through a plug of silica gel, using 4:1 hexane/ethyl acetate mixture as the eluent. Fractions containing the desired material were grouped and concentrated to provide a cream colored solid (1.63 g). NMR analysis of the cream colored solid indicated a structure that was consistent with 8,10-dibromo-7,7-dimethyl-3-(trifluoromethyl)-7H-benzo[c]fluoren-5-ol.

Step 6

Into a reaction flask containing a chloroform solution (50 mL) of the product from Step 6,8,10-dibromo-7,7-dimethyl-3-(trifluoromethyl)-7H-benzo[c]fluoren-5-ol (1.63 g) was added 1,1-bis(4-methoxyphenyl)prop-2-yn-1-ol (1.08 g), tri-isopropylorthoformate (0.90 mL) and pyridinium p-toluenesulfonate (0.10 g). The solution was heated to reflux for 2 h. The reaction mixture was concentrated under reduced pressure to provide an oily residue. Diethyl ether was added to the residue to provide a cream colored precipitate. The cream colored precipitate was collected by vacuum filtration (2.30 g) and used directly in the next Step. NMR analysis of the cream colored precipitate indicated a structure that was consistent with 3,3-bis(4-methoxyphenyl)-10,12-dibromo-6-trifluoromethyl-13,13-dimethyl-3,13-dihydro-indeno[2',3':3,4]naphtho[1,2-b]pyran.

Step 7

Into a reaction flask containing the product from Step 6 (2.30 g) and 4'-(4-trans-pentylcyclohexyl)-N-(4-(4,4,5,5-tetramethyl-1,3,2-dioxaborolan-2-yl)phenyl)-[1,1'-biphenyl]-4-carboxamide (1.72 g) in a 1:1 mixture of THF (40 mL) and water (40 mL) was added potassium fluoride (1.81 g, 30.68 mmol). The solution was degassed by bubbling with nitrogen for 10 min. To the resulting solution, bis(triphenylphosphine) palladium(II) chloride (0.22 g, 0.31 mmol) was added. The solution was heated to reflux for 16 h. The reaction mixture was cooled to room temperature and diluted with ethyl acetate. The mixture was filtered through a bed of CELITE® filtering aid and the filtrate was partitioned with ethyl acetate and water. The ethyl acetate extract was collected, dried with anhydrous sodium sulfate and concentrated to provide an oily residue. The residue was purified by column chromatography using 4:1 hexane and ethyl acetate mixture as the eluent. Fractions that contained the desired product were grouped and concentrated in vacuo to provide an oily residue. The oil was dissolved in a minimum amount of dichloromethane and added drop-wise to a vigorously stirred solution of methanol. The resulting precipitate was collected by vacuum filtration and dried to yield a purple solid (0.90 g). NMR analysis of the purple solid indicated a structure that was consistent with 3,3-bis(4-methoxyphenyl)-10-[4-(4-(4-(4-trans-pentylcyclohexyl)phenyl)benzamido) phenyl]-6-trifluoromethyl-12-bromo-13,13-dimethyl-3,13-dihydro-indeno[2',3':3,4]naphtho[1,2-b]pyran.

Example 11

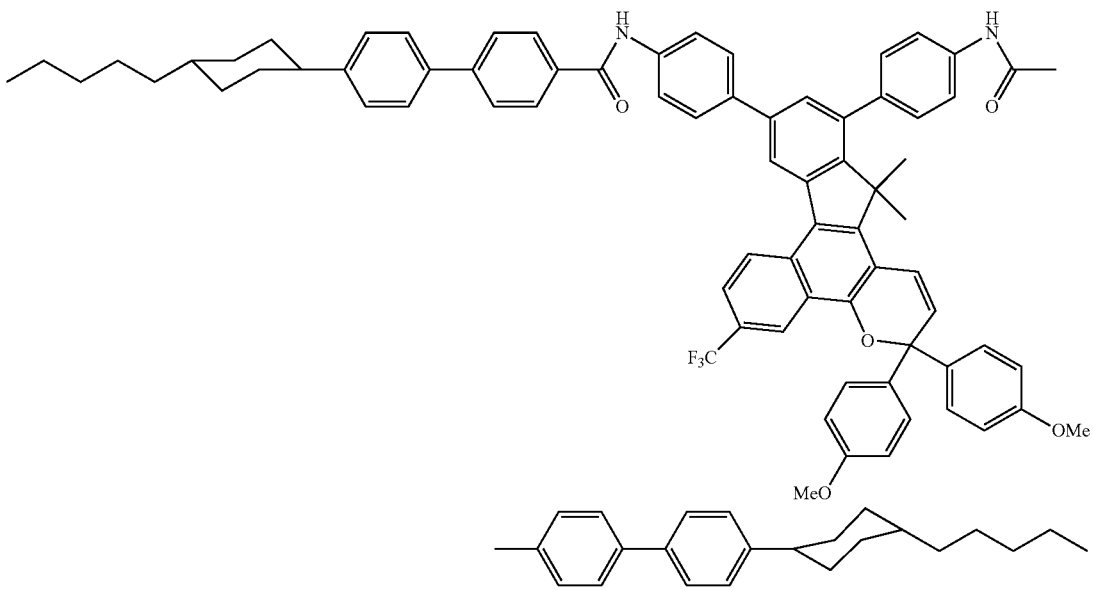

The product of Example 10 was fractionated using column chromatography by increasing the polarity of the hexane and ethyl acetate (1:1) eluent to provide polar fractions. The fractions were grouped and concentrated in vacuo to yield an oily residue. The oil was dissolved in a minimum amount of dichloromethane and added drop-wise to vigorously stirred solution of methanol. The resulting precipitate was collected by vacuum filtration and dried to provide blue-purple solid (0.30 g). NMR analysis of the purple solid indicated a structure that was consistent with 3,3-bis(4-methoxyphenyl)-10,12-bis[4-(4-(4-(4-trans-pentylcyclohexyl)phenyl)benzamido)phenyl]-6-trifluoromethyl-13,13-dimethyl-3,13-dihydro-indeno[2,3':3,4]naphtho[1,2-b]pyran.

Example 12

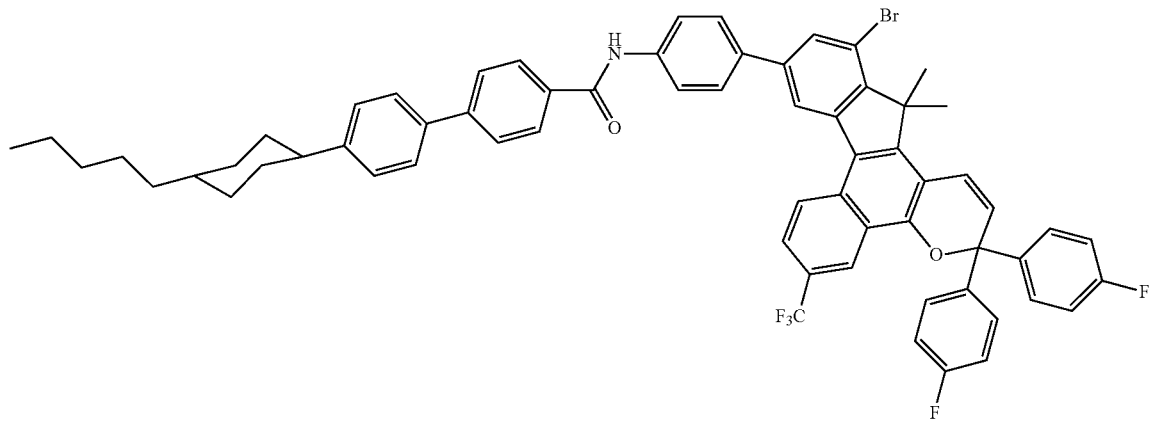 [SMILES: CCCCCC1CCC(c2ccc(-c3ccc(C(=O)Nc4ccc(-c5cc(Br)c6c(c5)-c5c(c7c(c8cc(C(F)(F)F)ccc58)OC(c5ccc(F)cc5)(c5ccc(F)cc5)C=C7)C6(C)C)cc4)cc3)cc2)CC1]

The procedures of Example 10 were followed except that 1,1-bis(4-fluorophenyl)prop-2-yn-1-ol was used in place of 1,1-bis(4-methoxyphenyl)prop-2-yn-1-ol in Step 6. NMR analysis showed that the final product had a structure consistent with 3,3-bis(4-fluorophenyl)-10-[4-(4-(4-(4-trans-pentylcyclohexyl)phenyl)benzamido)phenyl]-6-trifluoromethyl-12-bromo-13,13-dimethyl-3,13-dihydro-indeno[2',3':3,4]naphtho[1,2-b]pyran.

Example 13

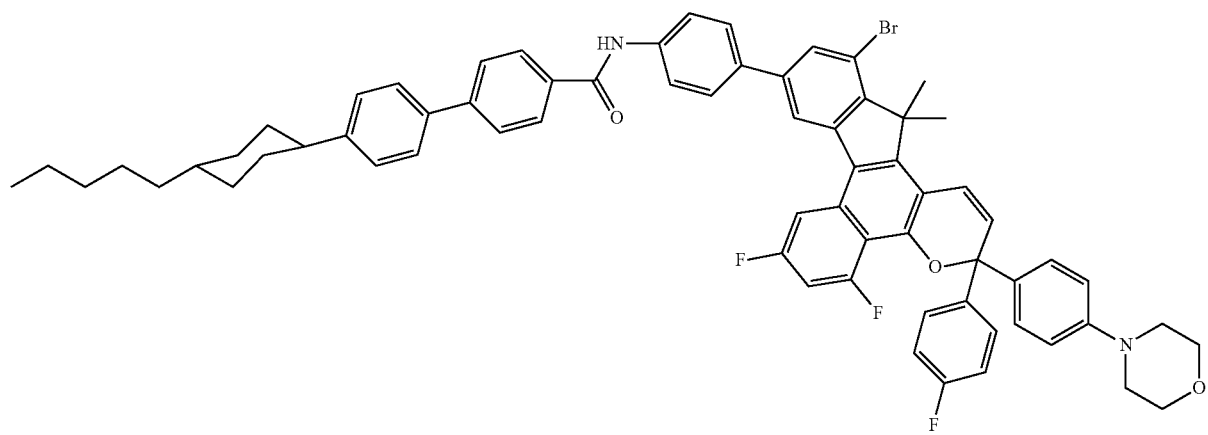 [SMILES: CCCCCC1CCC(c2ccc(-c3ccc(C(=O)Nc4ccc(-c5cc(Br)c6c(c5)-c5c(c7c(c8c(F)cc(F)cc58)OC(c5ccc(F)cc5)(c5ccc(N8CCOCC8)cc5)C=C7)C6(C)C)cc4)cc3)cc2)CC1]

The procedures of Example 10 were followed except for the following: in Step 1, 3,5-difluorobenzoyl chloride was used in place of 4-trifluoromethylbenzoyl chloride; in Step 4, the product was used without purification in the next Step; in Step 5, the desired 8,10-dibromo-2,4-difluoro-7,7-dimethyl-7H-benzo[c]fluoren-5-ol was recrystallized using ethyl acetate as solvent; in Step 6,1-(4-fluorophenyl)-1-(4-(N-morpholino)phenyl)prop-2-yn-1-ol was used in place of 1,1-bis(4-methoxyphenyl)prop-2-yn-1-ol; in Step 7, a different catalysis system of palladium acetate/triphenylphosphine/sodium carbonate/dimethoxymethane/ethanol was used in place of bis(triphenylphosphine)palladium(II) chloride/potassium fluoride/THF/water. NMR analysis showed that the final product had a structure consistent with 3-(4-fluorophenyl)-3-(4-morpholinophenyl)-10-[4-(4-(4-(4-trans-pentylcyclohexyl)phenypbenzamido)phenyl]-5,7-difluoro-12-bromo-13,13-dimethyl-3,13-dihydro-indeno[2',3':3,4]naphtho[1,2-b]pyran.

Example 14

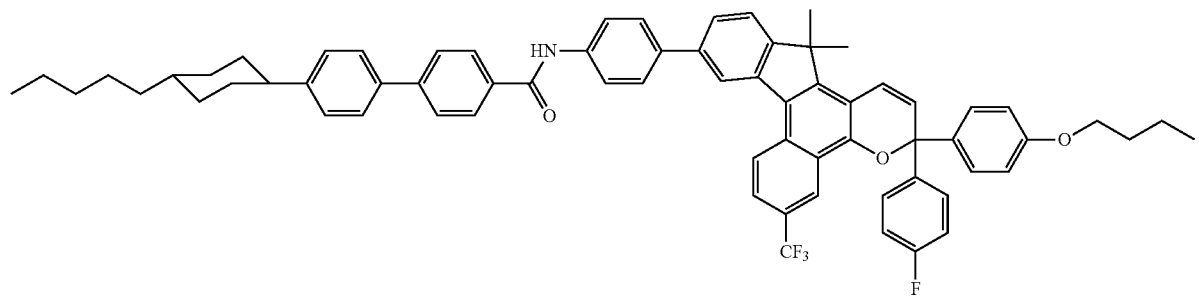 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

Step 1 to Step 4

Procedures from Step 1 to Step 4 of Example 10 were followed.

Step 5

8,10-Dibromo-7,7-dimethyl-3-(trifluoromethyl)-7H-benzo[c]fluoren-5-yl acetate (53.88 g) from Step 4 and 4'-(4-trans-pentylcyclohexyl)-N-(4-(4,4,5,5-tetramethyl-1,3,2-dioxaborolan-2-yl)phenyl)-[1,1'-biphenyl]-4-carboxamide (56.27 g) were added to reaction flask and dissolved in a 1:1 mixture of toluene (1000 mL) and ethanol (1000 mL). Potassium carbonate (42.26 g) and triphenylphosphine (8.02 g) were added to the solution which was degassed by bubbling nitrogen for 20 min. To the resulting solution, palladium acetate (2.29 g) was added and the mixture was heated to reflux for 3 h. The reaction mixture was cooled to room temperature and a degassed suspension of bis(triphenylphosphine)palladium(II) chloride (7.15 g) in toluene (100 mL) and ethanol (100 mL) was added. The reaction mixture was heated to reflux for 16 h. The reaction mixture was cooled to room temperature and diluted with ethyl acetate (500 mL). The mixture was filtered through CELITE® filtering aid and the filtrate was collected and concentrated in vacuo to provide a residue. The residue was purified by column chromatography using 19:1 toluene and ethyl acetate mixture as the eluent. Fractions that contained the desired product were grouped and concentrated in vacuo to provide a cream colored residue. Toluene was added to the residue to precipitate the product. The resulting precipitate was collected by vacuum filtration and dried to provide a cream colored solid (32 g). NMR analysis of the cream colored solid indicated a structure that was consistent 7,7-dimethyl-3-trifluoromethyl-10-[4-(4-(4-(4-trans-pentylcyclohexyl)phenyl)benzamido)phenyl]-7H-benzo[c]fluoren-5-ol.

Step 6

7,7-Dimethyl-3-trifluoromethyl-10-[4-(4-(4-(4-trans-pentylcyclohexyl)phenyl)benzamido)phenyl]-7H-benzo[c]fluoren-5-yl from Step 5 (18.00 g) was added to a reaction flask and dissolved in tetrahydrofuran (200 mL). 4-Dodecylbenzenesulfonic acid (0.54 g) was added as a solution in toluene (20 mL). 1-(4-Butoxyphenyl)-1-(4-fluorophenyl)prop-2-yn-1-ol (14.52 g) was added in 5 portions as a solution in toluene (20 mL) and the mixture was heated to reflux for 6 h. The reaction mixture was cooled to room temperature and the solvent was removed in vacuo to provide a residue. The residue was purified by column chromatography using 1:1 hexane and toluene mixture as the eluent. Fractions containing the desired product were grouped and concentrated in vacuo to provide an oily residue. The oil was dissolved in a minimum amount of dichloromethane and added drop-wise to a vigorously stirred solution of methanol. The resulting precipitate was collected by vacuum filtration and dried to provide purple solid (9.97 g). NMR analysis of the purple solid indicated a structure that was consistent with 3-(4-fluorophenyl)-3-(4-butoxyphenyl)-10-[4-(4-(4-(4-trans-pentylcyclohexyl)phenypbenzamido)phenyl]-6-trifluoromethyl-13,13-dimethyl-3,13-dihydro-indeno[2',3':3,4]naphtho[1,2-b]pyran.

Example 15

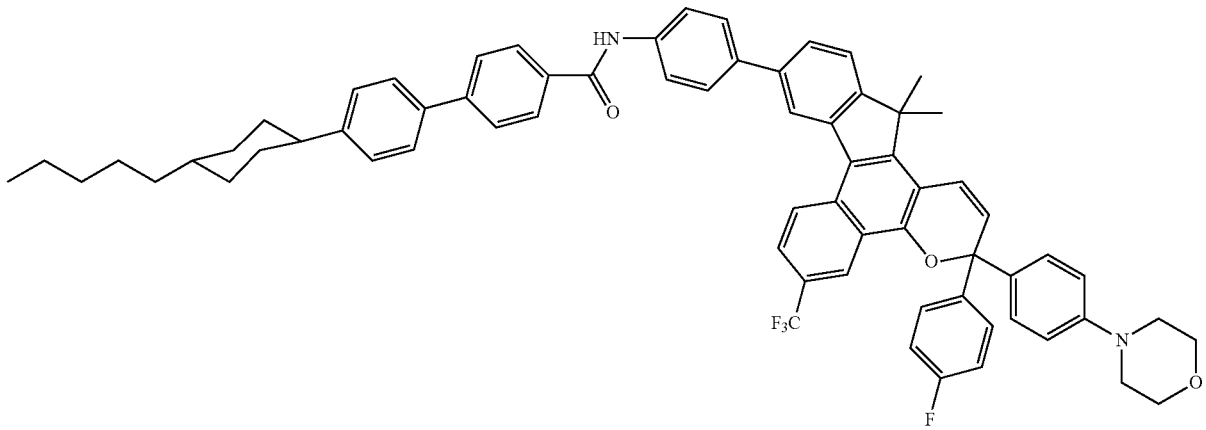 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(F)cc5)(c5ccc(N8CCOCC8)cc5)C=C7)C6(C)C)cc4)cc3)cc2)CC1]

The procedures from Example 14 were followed except that 1-(4-fluorophenyl)-1-(4-(N-morpholino)phenyl)prop-2-yn-1-ol was used in place of 1-(4-butoxyphenyl)-1-(4-fluorophenyl)prop-2-yn-1-ol in Step 6. NMR analysis showed that the structure was consistent with 3-(4-florophenyl)-3-(4-(N-morpholino)phenyl)-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 16

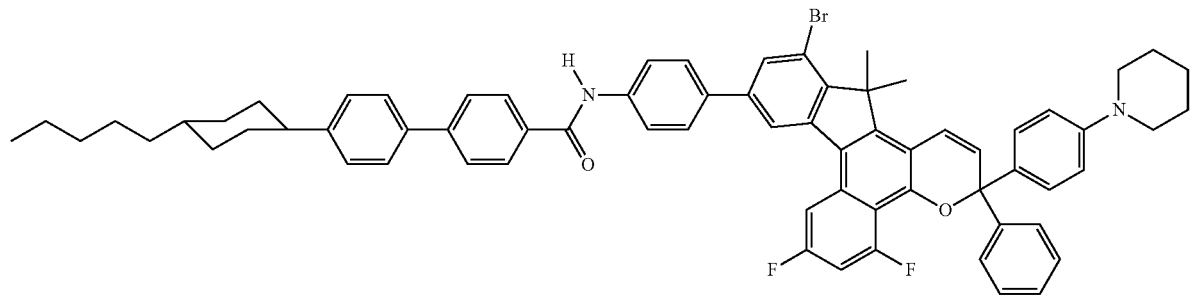 [SMILES: CCCCCC1CCC(c2ccc(-c3ccc(C(=O)Nc4ccc(-c5cc(Br)c6c(c5)-c5c(c7c(c8c(F)cc(F)cc58)OC(c5ccccc5)(c5ccc(N8CCCCC8)cc5)C=C7)C6(C)C)cc4)cc3)cc2)CC1]

The procedures from Example 13 were followed except that 1-phenyl-144-piperidinophenyl)prop-2-yn-1-ol was used in place of 1-(4-N-morpholinophenyl)-1-(4-fluorophenyl)prop-2-yn-1-ol. NMR analysis showed that the structure was consistent with 3-phenyl-3-(4-piperidinophenyl)-10-[4-(4-(4-(4-trans-pentylcyclohexyl)phenyl)benzamido)phenyl]-5,7-difluoro-12-bromo-13,13-dimethyl-3,13-dihydro-indeno[2',3':3,4]naphtho[1,2-b]pyran.

Example 17

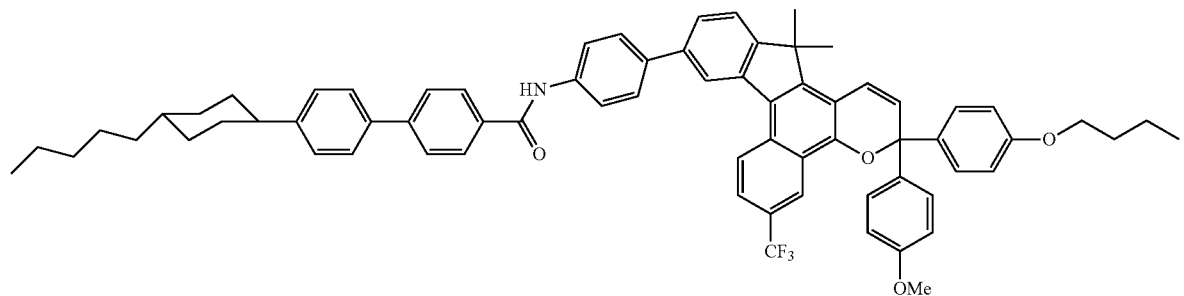 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(OC)cc5)(c5ccc(OCCCC)cc5)C=C7)C6(C)C)cc4)cc3)cc2)CC1]

The procedures from Example 14 were followed except that 1-(4-butoxyphenyl)-1-(4-methoxyphenyl)prop-2-yn-1-ol was used in place of 1-(4-butoxyphenyl)-1-(4-fluorophenyl)prop-2-yn-1-ol. NMR analysis showed that the product had a structure consistent with 3-(4-methoxyphenyl)-3-(4-butoxyphenyl)-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 18

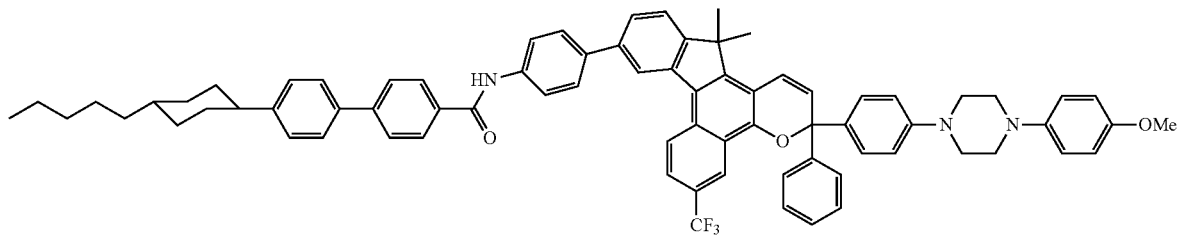 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccccc5)(c5ccc(N8CCN(c9ccc(OC)cc9)CC8)cc5)C=C7)C6(C)C)cc4)cc3)cc2)CC1]

The procedures from Example 14 were followed except that 1-(4-(4-(4-methoxyphenyl)piperazin-1-yl)phenyl)-1-phenylprop-2-yn-1-ol was used in place of 1-(4-butoxyphenyl)-1-(4-fluorophenyl)prop-2-yn-1-ol. NMR analysis showed that the product had a structure consistent with 3-(4-(4-(4-methoxyphenyl)piperazin-1-yl)phenyl)-3-phenyl-10-[4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 19

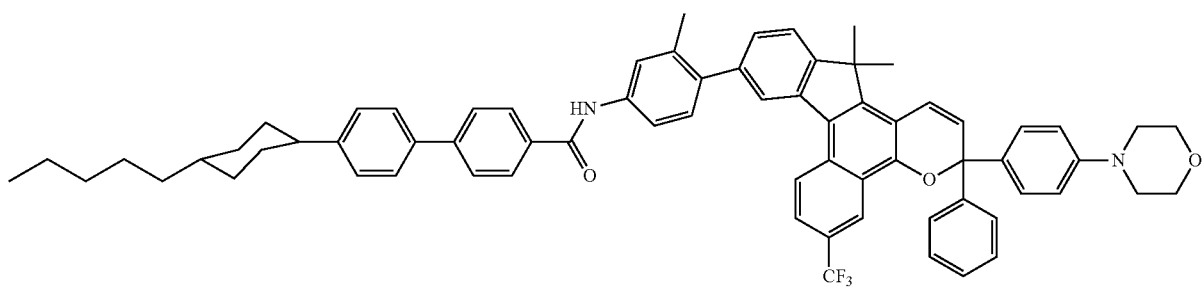 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccccc5)(c5ccc(N8CCOCC8)cc5)C=C7)C6(C)C)c(C)c4)cc3)cc2)CC1]

The procedures from Example 14 were followed except that 1-phenyl-1-(4-(N-morpholino)phenyl)prop-2-yn-1-ol was used in place of 1-(4-butoxyphenyl)-1-(4-fluorophenyl)prop-2-yn-1-ol and N-(3-methyl-4-(4,4,5,5-tetramethyl-1,3,2-dioxaborolan-2-yl)phenyl)-4'-(4-pentylcyclohexyl)-[1,1'-biphenyl]-4-carboxamide was used in place of 4'-(4-trans-pentylcyclohexyl)-N-(4-(4,4,5,5-tetramethyl-1,3,2-dioxaborolan-2-yl)phenyl)-[1,1'-biphenyl]-4-carboxamide. NMR indicated that the structure was consistent with 3-phenyl-3-(4-(N-morpholino)phenyl)-10-[4-(4-(4-(4-trans-pentylcyclohexyl)phenyl)benzamido)-2-methylphenyl]-6-trifluoromethyl-13,13-dimethyl-3,13-dihydro-indeno[2',3':3,4]naphtho[1,2-b]pyran.

Example 20

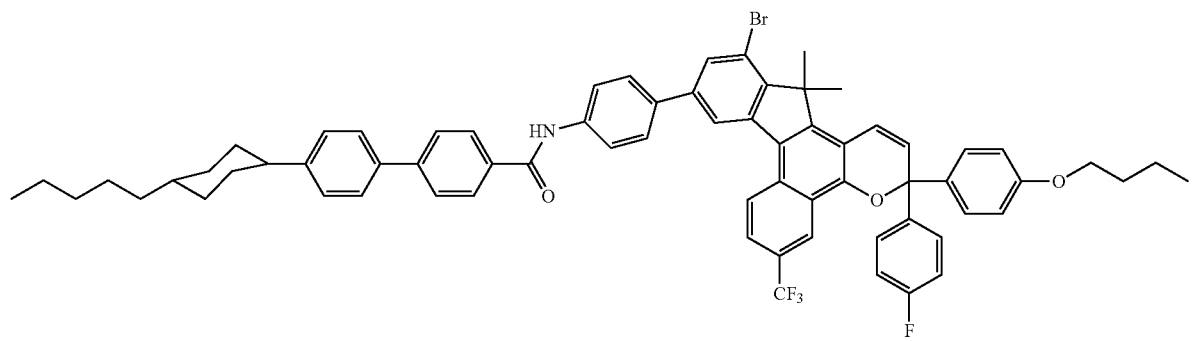 [SMILES: CCCCCC1CCC(c2ccc(-c3ccc(C(=O)Nc4ccc(-c5cc(Br)c6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

The procedures of Example 10 were followed except that in Step 6,1-(4-fluorophenyl)-1-(4-butoxyphenyl)prop-2-yn-1-ol was used in place of 1,1-bis(4-methoxyphenyl)prop-2-yn-1-ol. NMR analysis showed that the final product had a structure consistent with 3-(4-fluorophenyl)-3-(4-butoxyphenyl)-10-[4-(4-(4-(4-trans-pentylcyclohexyl)phenyl)benzamido)phenyl]-6-trifluoromethyl-12-bromo-13,13-dimethyl-3,13-dihydro-indeno[2',3':3,4]naphtho[1,2-b]pyran.

Example 21

Product from Example 20, 3-(4-fluorophenyl)-3-(4-butoxyphenyl)-10-[4-(4-(4-(4-trans-pentylcyclohexyl)phenyl)benzamido)phenyl]-6-trifluoromethyl-12-bromo-13,13-dimethyl-indeno[2',3':3,4]naphtho[1,2-b]pyran (3.77 g), was added to a reaction flask and dissolved in tetrahydrofuran (10 mL) and cooled to −78° C. n-Butyl lithium (6 mL, 2.5 M in hexanes) was added and stirred for 30 min. Brine was added to the reaction mixture and it was warmed to room temperature. The aqueous layer was extracted with ethyl acetate. The recovered organic layer was dried with anhydrous sodium sulfate, filtered and concentrated to provide an oily residue. Two photochromic compounds were present in the oily residue. They were separated by column chromatography using 9:1 hexane and ethyl acetate mixture as the eluent. Fractions containing the more polar compound were grouped and concentrated to provide an oil. The oil was dissolved in a minimum amount of dichloromethane and added drop-wise to vigorously stirred methanol. The resulting precipitate was collected by vacuum filtration and dried to a purple solid (0.3 g). NMR analysis of the purple solid indicated a structure that was consistent with 3-(4-butoxyphenyl)-3-(4-fluorophenyl)-12-hydroxyl-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

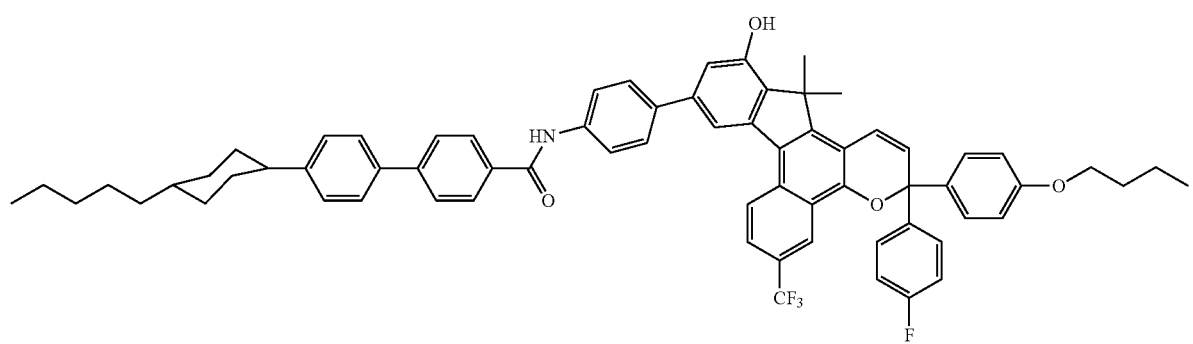 [SMILES: CCCCCC1CCC(c2ccc(-c3ccc(C(=O)Nc4ccc(-c5cc(O)c6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

Example 22

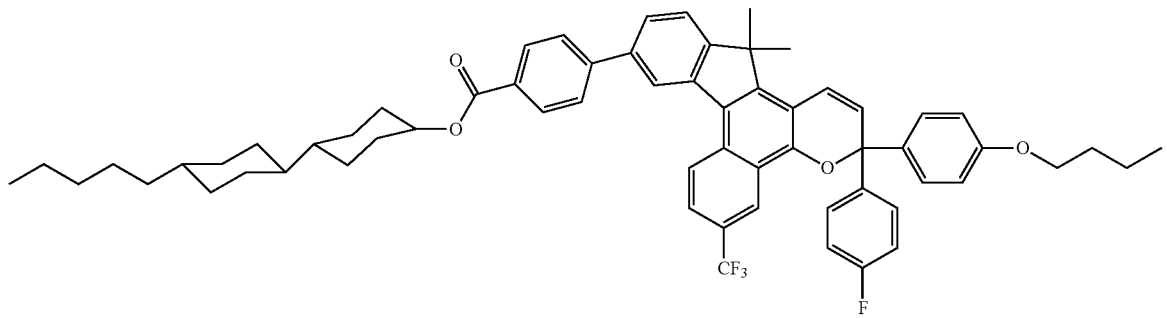 [SMILES: CCCCCC1CCC(C2CCC(OC(=O)c3ccc(-c4ccc5c(c4)-c4c(c6c(c7cc(C(F)(F)F)ccc47)OC(c4ccc(F)cc4)(c4ccc(OCCCC)cc4)C=C6)C5(C)C)cc3)CC2)CC1]

Step 1
The procedure from Step 2 of Example 3 was followed except that 4'-pentyl-[(trans, trans)-1,1'-bi(cyclohexan)]-4-ol was used in place of 4-(trans-4-pentylcyclohexyl)benzoic acid. NMR showed that the product had a structure consistent with (trans, trans)-4'-pentyl-[1,1'-bi(cyclohexan)]-4-yl 4-(4,4,5,5-tetramethyl-1,3,2-dioxaborolan-2-yl)benzoate.

Step 2
The procedures from Example 14 were followed except that in Step 5 (trans, trans)-4'-pentyl-[1,1'-bi(cyclohexan)]-4-yl 4-(4,4,5,5-tetramethyl-1,3,2-dioxaborolan-2-yl)benzoate was used in place of 4'-(4-trans-pentylcyclohexyl)-N-(4-(4,4,5,5-tetramethyl-1,3,2-dioxaborolan-2-yl)phenyl)-[1,1'-biphenyl]-4-carboxamide. NMR analysis showed that the product had a structure consistent with 3-(4-butoxyphenyl)-3-(4-fluorophenyl)-10-[4-((trans,trans)-4'-pentyl-[1,1-bi(cyclohexan)]-4-oxycarbonyl)phenyl]-6-trifluoromethyl-13,13-dimethyl-3,13-dihydro-indeno[2',3':3,4]naphtho[1,2-b]pyran.

Example 23

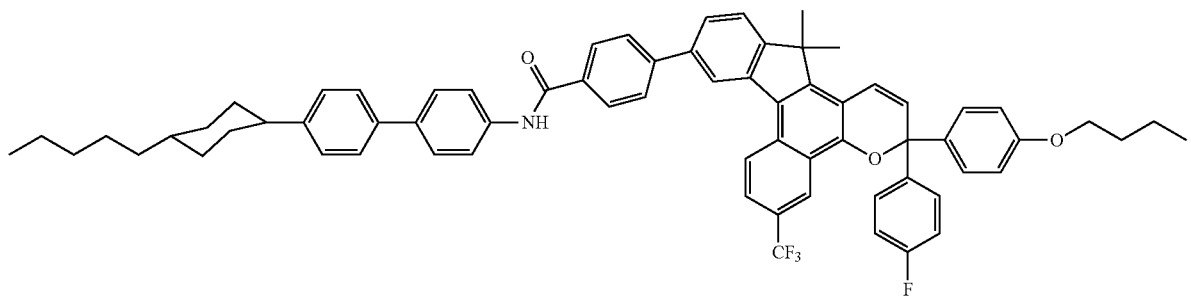 [SMILES: CCCCCC1CCC(c2ccc(-c3ccc(NC(=O)c4ccc(-c5ccc6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

Step 1
To a degassed solution of 1-bromo-4-(4-pentylcyclohexyl)benzene (300 g) in 1,4-dioxane (2 L) in a reaction flask was added Pd(PPh$_3$)$_4$ (10.7 g). After stirring for 10 min at room temperature, a solution of aqueous 1 M K$_2$CO$_3$ (485 mL, 4.85 mmol) and 4-(4,4,5,5-tetramethyl-1,3,2-dioxaborolan-2-yl)aniline (274.5 g, 0.97 mol) were added. The reaction mixture was refluxed for 36 h. The solvent was evaporated and the residue was recrystallized using CH$_2$Cl$_2$-MeOH (400 mL-1500 mL). White crystals (256 g) were obtained as the product. NMR showed that the product had a structure consistent with 4'-(trans-4-pentylcyclohexyl)-[1,1'-biphenyl]-4-amine.

Step 2
A mixture of 4-(4,4,5,5-tetramethyl-1,3,2-dioxaborolan-2-yl)benzoic acid (82.6 g 0.35 mol), 1,1'-carbonyldiimidazole (56.6 g, 0.35 mol) and 500 mL of THF (500 ml) were stirred in a reaction flask at room temperature for 5 h. To the reaction mixture, the product of Step 1,4'-(trans-4-pentylcyclohexyl)-[1,1'-biphenyl]-4-amine (102 g) was added. The mixture was stirred at room temperature for 24 hours. The solvent was evaporated and the residue was recrystallyzed with CH$_2$Cl$_2$-MeOH (150 mL-400 mL). White crystals (156 g) were obtained as the product. NMR showed that the product had a structure consistent with N-(4'-(trans-4-pentylcyclohexyl)-[1,1'-biphenyl]-4-yl)-4-(4,4,5,5-tetramethyl-1,3,2-dioxaborolan-2-yl)benzamide.

Step 3
The procedures from Example 14 were followed except that in Step 5, N-(4'-(trans-4-pentylcyclohexyl)-[1,1'-biphenyl]-4-yl)-4-(4,4,5,5-tetramethyl-1,3,2-dioxaborolan-2-yl)benzamide was used in place of 4'-(4-trans-pentylcyclohexyl)-N-(4-(4,4,5,5-tetramethyl-1,3,2-dioxaborolan-2-yl)phenyl)-[1,1'-biphenyl]-4-carboxamide. NMR analysis showed that the product had a structure consistent with 3-(4-methoxyphenyl)-3-(4-butoxyphenyl)-10-[4-((4'-(trans-4-pentylcyclohexyl)-[1,1'-biphenyl]-4-yl)carbamoyl)phenyl]-6-trifluoromethyl-13,13-dimethyl-3,13-dihydro-indeno[2',3':3,4]naphtho[1,2-b]pyran.

Example 24

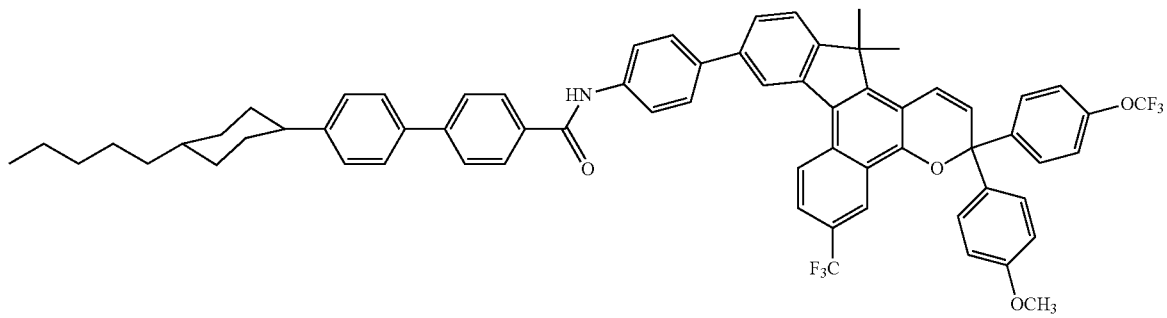 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(OC)cc5)(c5ccc(OC(F)(F)F)cc5)C=C7)C6(C)C)cc4)cc3)cc2)CC1]

Step 1

4-Trifluoromethoxy benzoylchloride (1.00 g) and anisole (0.60 g) were dissolved in chloroform (20 mL) in a reaction flask and cooled to 0-5° C. by an ice bath. Aluminum chloride (0.90 g) was added and stirred for 15 min at 0-5° C. The ice bath was removed and the reaction was warmed to room temperature and stirred for 48 h and poured into water (100 mL) and stirred for 15 min. The aqueous layer was extracted with ethyl acetate (300 mL). The organic layer was recovered, washed with saturated sodium bicarbonate, brine, dried with anhydrous sodium sulfate and concentrated in vacuo to provide a residue. The residue was purified by column chromatography using 9:1 hexane and ethyl acetate mixture as the eluent. Fractions containing the desired material were grouped and concentrated to provide a solid. Hexanes were added and the solids were collected by vacuum filtration (0.55 g). NMR of the solid indicated a structure that was consistent with (4-methoxyphenyl)(4-(trifluoromethoxy)phenyl)methanone.

Step 2

(4-Methoxyphenyl)(4-(trifluoromethoxy)phenyl)methanone (0.55 g) was added to a reaction flask and dissolved in dimethylformamide (10 mL) saturated with acetylene. Sodium acetylide (0.1 g) was added and the reaction mixture was stirred at room temperature for 30 min. The reaction mixture was carefully poured into ice-cold water (100 mL) and stirred for 15 min. The aqueous layer was extracted with ethyl acetate. The organic layers were recovered and combined. The resulting product was dried with anhydrous sodium sulfate and concentrated to provide an oil (0.55 g). NMR analysis of the oil indicated a structure that was consistent with 1-(4-methoxyphenyl)-1-(4-(trifluoromethoxy)phenyl)prop-2-yn-1-ol.

Step 3

The procedures from Example 14 were followed except that 1-(4-methoxyphenyl)-1-(4-(trifluoromethoxy)phenyl)prop-2-yn-1-ol from Step 2 above was used in place of 1-(4-butoxyphenyl)-1-(4-fluorophenyl)prop-2-yn-1-ol in Step 6 of Example 14. NMR analysis showed that the product had a structure consistent with 3-(4-methoxyphenyl)-3-(4-trifluoromethoxyphenyl)-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 25

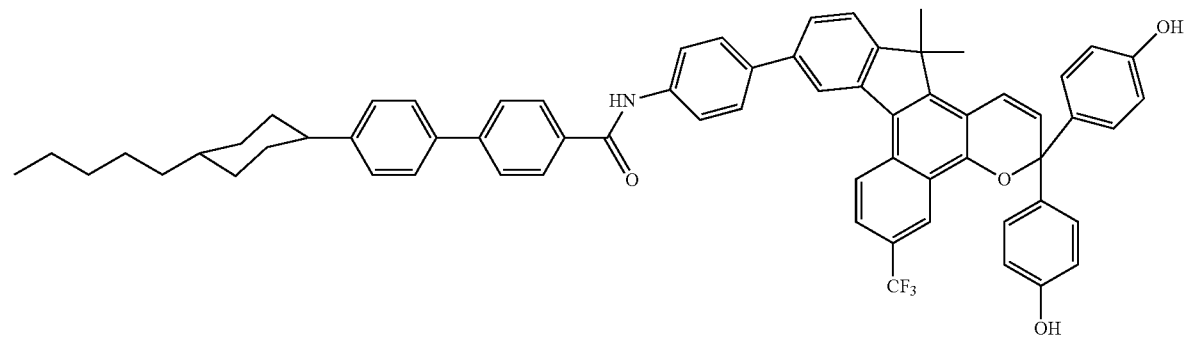 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccc(O)cc5)(c5ccc(O)cc5)C=C7)C6(C)C)cc4)cc3)cc2)CC1]

The procedures from Example 14 were followed except that 1,1-bis(4-(((tetrahydro-2H-pyran-2-yl)oxy)phenyl)prop-2-yn-1-ol was used in place of 1-(4-butoxyphenyl)-1-(4-fluorophenyl)prop-2-yn-1-ol in Step 6. Also in Step 6 after the reaction and before the column separation, the residue was taken up in tetrahydrofuran and methanol with the addition of p-toluenesulfonic acid, refluxed for 1 h and concentrated. NMR analysis of the obtained solid indicated a structure that was consistent with 3-bis(4-hydroxyphenyl)-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 26

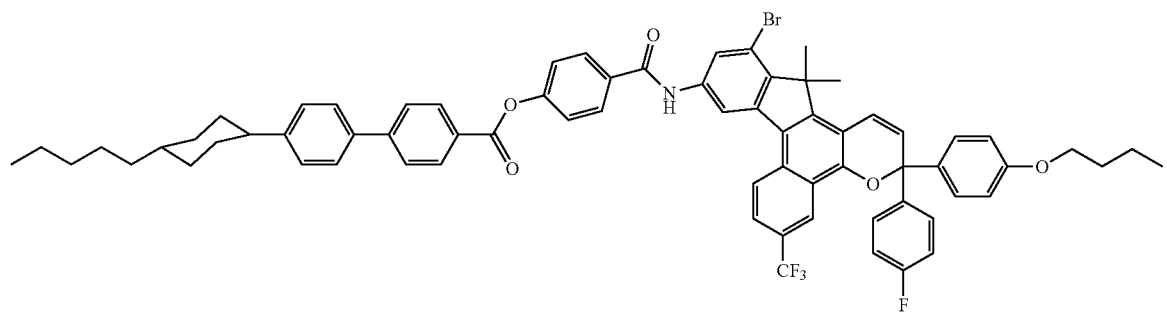 [SMILES: CCCCCC1CCC(c2ccc(-c3ccc(C(=O)Oc4ccc(C(=O)Nc5cc(Br)c6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

Step 1

To a three neck round bottom flask (100 mL) were added bis(dibenzylideneacetone)plalladium(0) (0.55 g), 2-di-tert-butylphosphino-3,4,5,6-tetramethyl-2',4',6'-triisopropyl-1,1-biphenyl (1.14 g), crushed potassium phosphate (8.72 g), 8,10-dibromo-7,7-dimethyl-3-(trifluoromethyl)-7H-benzo[c]fluoren-5-yl acetate (5.00 g) from Step 4 of Example 10 and 4-hydroxybenzamide (2.15 g). The flask was evacuated and filled with nitrogen. Degassed tert-butanol (30 mL) was added and the mixture was heated to reflux for 6 h. The reaction mixture was cooled to room temperature and diluted with EtOAc. The solution was filtered through Celite and the filtrate was collected, concentrated and the residue was purified by column chromatography using 4:1 ethyl acetate and hexanes mixture as the eluent. Fractions containing the desired material were grouped and concentrated to provide an oil. The oil was dissolved in a minimum amount of ethyl acetate and hexanes was added to crystallize the product. The crystals were collected by vacuum filtration and dried to provide a white colored solid (4.27 g). NMR analysis of the white colored solid indicated a structure that was consistent with N-(8-bromo-5-hydroxy-7,7-dimethyl-3-(trifluoromethyl)-7H-benzo[c]fluoren-10-yl)-4-hydroxybenzamide.

Step 2

To a chloroform solution (20 mL) in a reaction flask, of the product from Step 5 (1.69 g) were added 1-(4-butoxyphenyl)-1-(4-fluorophenyl)prop-2-yn-1-ol (1.12 g) and 4-dodecylbenzenesulfonic acid (0.10 g). The reaction mixture was stirred at room temperature for 18 h. The reaction mixture was concentrated under reduced pressure to provide an oily residue. The residue was purified by column chromatography using 1:1 hexane and toluene mixture as the eluent. Fractions containing the desired product were grouped and concentrated in vacuo to provide an oily residue. The oily residue was re-crystallized from methanol. The resulting solid was collected by vacuum filtration and dried to provide a cream colored solid (0.88 g). NMR analysis of the cream colored solid indicated a structure that was consistent with 12-bromo-3-(4-butoxyphenyl)-3-(4-fluorophenyl)-10-[4-hydroxybenzamido]-6-trifluoromethyl-13,13-dimethyl-3,13-dihydro-indeno[2',3':3,4]naphtho[1,2-b]pyran.

Step 3

Product from Step 2 (1.15 g) was dissolved in chloroform (20 mL) in a reaction flask. Triethylamine (0.6 mL) was added followed by 4'-(4-pentylcyclohexyl)biphenyl-4-carbonyl chloride from Step 4 of Example 2 (0.80 g). The reaction mixture was stirred at room temperature for 30 min. The solvent was removed in vacuo and the residue was purified by column chromatography using 9:1 hexanes and ethyl acetate mixtures as the eluent. Fractions containing the desired material were grouped and concentrated. The residue was dissolved in a minimum amount of dichloromethane and added drop-wise to a vigorously stirred solution of methanol. The resulting precipitate was collected by vacuum filtration and dried to a purple solid (1.30 g). NMR analysis of the purple solid indicated a structure that was consistent with 12-bromo-3-(4-butoxyphenyl)-3-(4-fluorophenyl)-10-[4-(4'-(4-trans-pentylcyclohexyl)-[1,1'-biphenyl]-4-carbonyloxy)benzamido]-6-trifluoromethyl-13,13-dimethyl-3,13-dihydro-indeno[2',3':3,4]naphtho[1,2-b]pyran.

Example 27

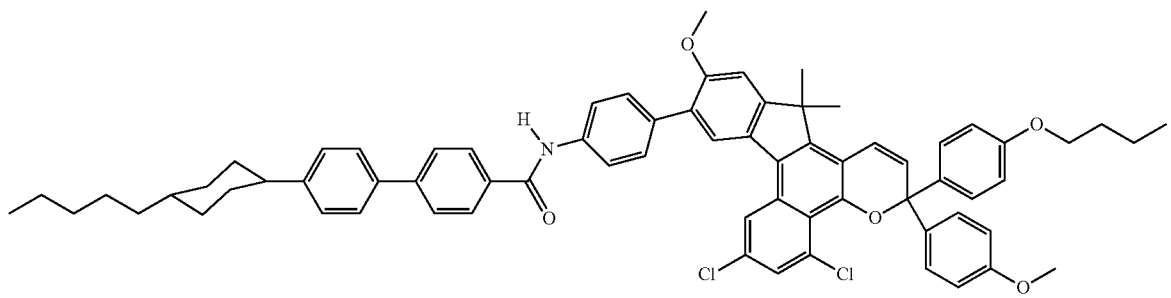 [SMILES: CCCCCC1CCC(c2ccc(-c3ccc(C(=O)Nc4ccc(-c5cc6c(cc5OC)C(C)(C)c5c7c(c8c(Cl)cc(Cl)cc8c5-6)OC(c5ccc(OC)cc5)(c5ccc(OCCCC)cc5)C=C7)cc4)cc3)cc2)CC1]

Step 1 to Step 4

Procedures from Step 1 to Step 4 of Example 10 were followed except that in Step 1, 3,5-dichlorobromobenzene and 4-methoxybenzoyl chloride was used in place of tribromobenzene and 4-trifluoromethylbenzoyl chloride. An off-white solid was obtained as the product. NMR indicated that the product had a structure consistent with 2,4-dichloro-9-methoxy-7,7-dimethyl-7H-benzo[c]fluoren-5-yl acetate.

Step 5

A mixture of 2,4-dichloro-9-methoxy-7,7-dimethyl-7H-benzo[c]fluoren-5-yl acetate from Step 4 (5 g), NBS (2.7 g) and DMF (100 ml) was stirred in a reaction flask and heated to 90° C. Two hours later, the resulting reaction mixture was poured into water (400 ml) and extracted with 1/1 ethyl acetate/THF (200 ml). The organic layer was collected, washed with sodium bisulfite water solution three times, dried and concentrated. To the recovered product, methanol (100 ml) was added. After filtration, an off white solid (4.4 g) was obtained as the product. NMR indicated that the product had a structure consistent with 10-bromo-2,4-dichloro-9-methoxy-7,7-dimethyl-7H-benzo[c]fluoren-5-yl acetate.

Step 6

A mixture of 10-bromo-2,4-dichloro-9-methoxy-7,7-dimethyl-7H-benzo[c]fluoren-5-yl acetate from Step 5 (4.3 g), 4'-(4-trans-pentylcyclohexyl)-N-(4-(4,4,5,5-tetramethyl-1,3,2-dioxaborolan-2-yl)phenyl)-[1,1'-biphenyl]-4-carboxamide (4.94 g), sodium carbonate (4 g), THF (200 ml), water (20 ml) and tetrakis(triphenylphosphine)palladium(0) (1 g) was placed in a reaction flask and degassed by bubbling nitrogen through the mixture for 10 minutes. The mixture was heated to reflux for 17 hours and potassium carbonate (5 g) and ethanol (50 ml) was added. After reflux for another 8 hours, extraction was applied using THF and sodium chloride saturated water. The resulting organic layer was collected, washed with 100 ml 1 N HCl three times, washed with 100 ml 1 N sodium sulfite water solution once, washed with sodium chloride saturated water once, dried over magnesium sulfate and concentrated. The obtained residue was dissolved in 10/1 toluene/THF (200 ml) and then passed through a silica gel plug column. The recovered clear solution was concentrated added to methanol and stirred for half an hour. The resulting solid was collected and dried. An off-white solid (7.5 g) was obtained as the product. NMR indicated that the product had a structure consistent with N-(4-(2,4-dichloro-5-hydroxy-9-methoxy-7,7-dimethyl-7H-benzo[c]fluoren-10-yl)phenyl)-4'-(4-trans-pentylcyclohexyl)-[1,1-biphenyl]-4-carboxamide.

Step 7

N-(4-(2,4-dichloro-5-hydroxy-9-methoxy-7,7-dimethyl-7H-benzo[c]fluoren-10-yl)phenyl)-4'-(4-pentylcyclohexyl)-[1,1'-biphenyl]-4-carboxamide from Step 6 (3 g), 1-(4-butoxyphenyl)-1-(4-methoxyphenyl)prop-2-yn-1-ol (1.8 g), p-toluenesulfonic acid (73 mg) and 1,2-dichloroethane (50 ml) was added to a reaction flask. The mixture was stirred and refluxed for 4 hours. After the solvent was removed, the product was purified by CombiFlash. A black solid (2 g) was obtained as the product. NMR indicated that the structure was consistent with 3-(4-butoxyphenyl)-3-(4-methoxyphenyl)-10-[4-(4-(4-(4-trans-pentylcyclohexyl)phenyl)benzamido)phenyl]-5,7-dichloro-11-methoxy-13,13-dimethyl-3,13-dihydro-indeno[2',3':3,4]naphtho[1,2-b]pyran.

Example 28

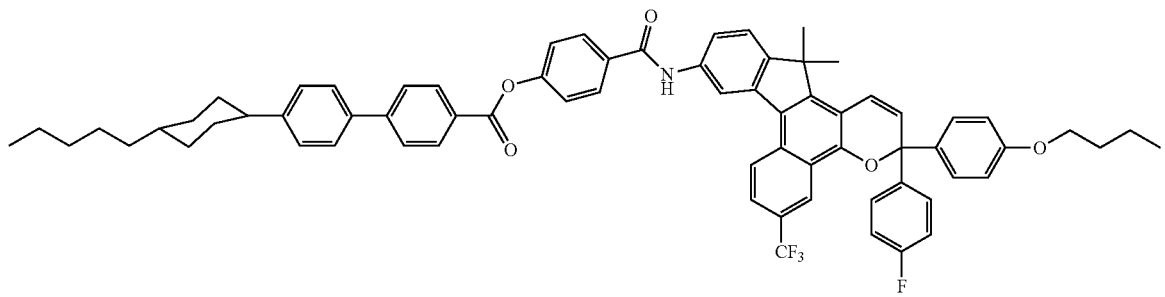 [SMILES: CCCCCC1CCC(c2ccc(-c3ccc(C(=O)Oc4ccc(C(=O)Nc5ccc6c(c5)-c5c(c7c(c8cc(C(F)(F)F)ccc58)OC(c5ccc(F)cc5)(c5ccc(OCCCC)cc5)C=C7)C6(C)C)cc4)cc3)cc2)CC1]

Step 1

N-(8-bromo-5-hydroxy-7,7-dimethyl-3-(trifluoromethyl)-7H-benzo[c]fluoren-10-yl)-4-hydroxybenzamide (5.00 g) from Step 1 of Example 26, potassium carbonate (5.10 g), 2-butanol (50 mL) and methanol (50 mL) were added to a round bottom flask and degassed for 10 min. Tetrakistriphenylphosphine palladium (0) (0.55 g) was added and heated to reflux under nitrogen for 2 h. The reaction mixture was cooled to room temperature and filtered through CELITE® filtering aid. The filtrate was concentrated and the residue was purified by column chromatography using 4:1 ethyl acetate and hexanes mixtures as the eluent. Fractions containing the desired material were grouped and concentrated to provide a foam (4.00 g). NMR analysis of the foam indicated a structure that was consistent with 4-hydroxy-N-(5-hydroxy-7,7-dimethyl-3-(trifluoromethyl)-7H-benzo[c]fluoren-10-yl)benzamide.

Step 2

The procedure of Steps 2 and 3 of Example 26 was followed except that in Step 2, the product of Step 1 above was used in place of N-(8-bromo-5-hydroxy-7,7-dimethyl-3-(trifluoromethyl)-7H-benzo[c]fluoren-10-yl)-4-hydroxybenzamide. NMR indicated that the structure was consistent with 3-(4-butoxyphenyl)-3-(4-fluorophenyl)-10-[4-(4-(4-trans-pentylcyclohexyl)-[1,1'-biphenyl]-4-carbonyloxy)benzamido]-6-trifluoromethyl-13,13-dimethyl-3,13-dihydro-indeno[2',3':3,4]naphtho[1,2-b]pyran.

Example 29

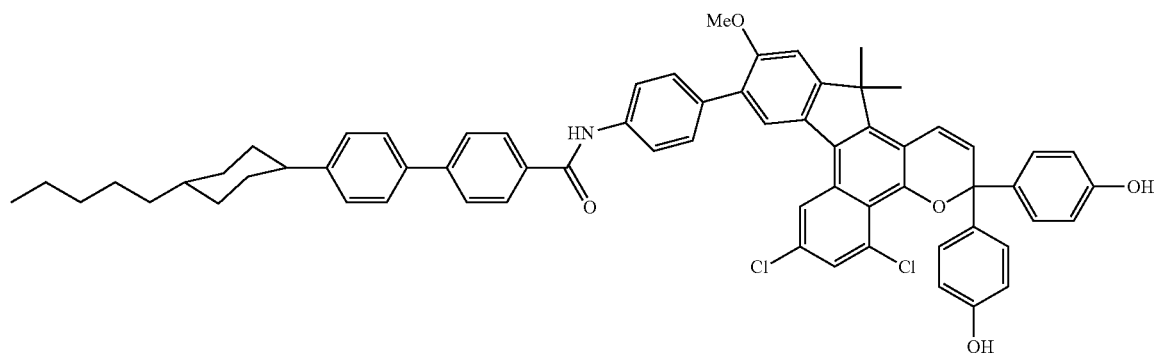 [SMILES: CCCCCC1CCC(c2ccc(-c3ccc(C(=O)Nc4ccc(-c5cc6c(cc5OC)C(C)(C)c5c7c(c8c(Cl)cc(Cl)cc8c5-6)OC(c5ccc(O)cc5)(c5ccc(O)cc5)C=C7)cc4)cc3)cc2)CC1]

Procedures from Example 27 were followed except for the following in Step 7: 1,1-bis(4-((tetrahydro-2H-pyran-2-yl)oxy)phenyl)prop-2-yn-1-ol was used in place of 1-(4-butoxyphenyl)-1-(4-methoxyphenyl)prop-2-yn-1-ol and before being subjected to CombiFlash, the product was dissolved in a solvent mixture of THF and methanol with pTSA (1 g) and refluxed for an hour and concentrated. NMR indicated that the product had a structure consistent with 3-bis(4-hydroxyphenyl)-10-[4-(4-(4-(4-trans-pentylcyclohexyl)phenyp-benzamido)phenyl]-5,7-dichloro-11-methoxy-13,13-dimethyl-3,13-dihydro-indeno[2',3':3,4]naphtho[1,2-b]pyran.

Example 30

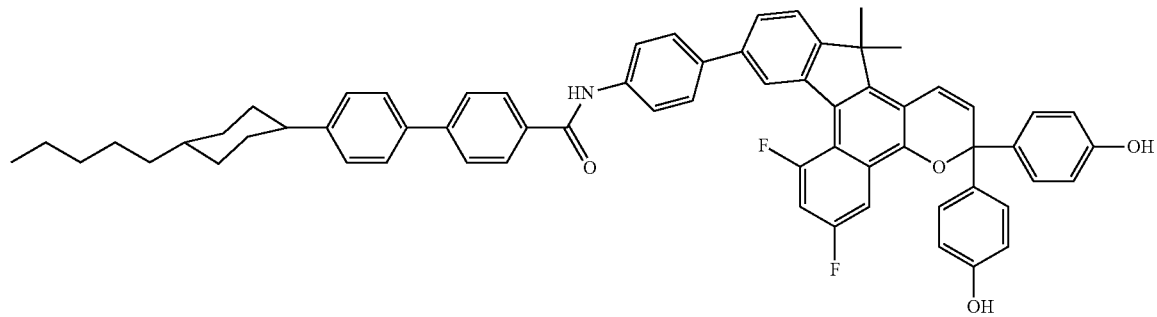 [SMILES: CCCCCC1CCC(c2ccc(-c3ccc(C(=O)Nc4ccc(-c5ccc6c(c5)-c5c(c7c(c8cc(F)cc(F)c58)OC(c5ccc(O)cc5)(c5ccc(O)cc5)C=C7)C6(C)C)cc4)cc3)cc2)CC1]

The procedures from Example 14 were followed except that in Step 1,2,4-difluorobenzoyl chloride was used in place of 4-trifluoromethylbenzoyl chloride and in Step 6, 1,1-bis(4-((tetrahydro-2H-pyran-2-yl)oxy)phenyl)prop-2-yn-1-ol was used in place of 1-(4-butoxyphenyl)-1-(4-fluorophenyl)prop-2-yn-1-ol and after the reaction and before the column separation, the residue was dissolved in tetrahydrofuran and methanol with the addition of p-toluenesulfonic acid, refluxed for 1 h and concentrated. NMR analysis of the obtained light blue solid indicated a structure that was consistent with 3-bis(4-hydroxyphenyl)-10-[4-(444-(4-trans-pentylcyclohexyl)phenyl)benzamido)phenyl]-6,8-difluoro-13,13-dimethyl-3,13-dihydro-indeno[2',3':3,4]naphtho[1,2-b]pyran.

Example 31

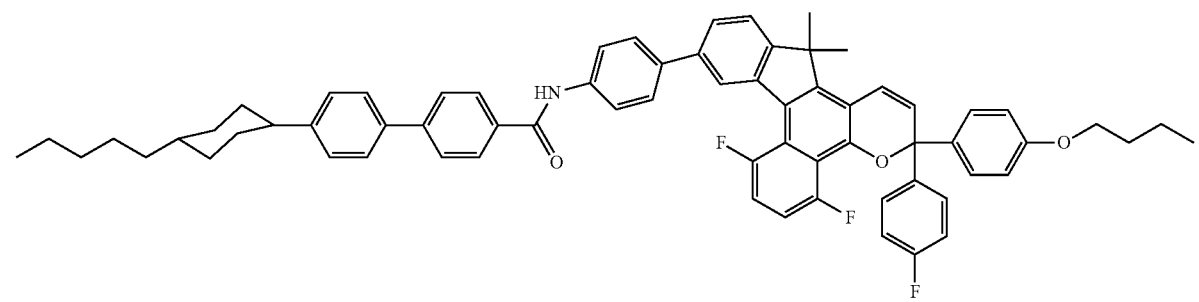 [SMILES: CCCCCC1CCC(c2ccc(-c3ccc(C(=O)Nc4ccc(-c5ccc6c(c5)-c5c(c7c(c8c(F)ccc(F)c58)OC(c5ccc(F)cc5)(c5ccc(OCCCC)cc5)C=C7)C6(C)C)cc4)cc3)cc2)CC1]

The procedures from Example 14 were followed except that in Step 1,2,5-difluorobenzoyl chloride was used in place of 4-trifluoromethylbenzoyl chloride. NMR analysis of the obtained solid indicated a structure that was consistent with 3-(4-fluorophenyl)-3-(4-butoxyphenyl)-10-[4-(4-(444-trans-pentylcyclohexyl)phenyl)benzamido)phenyl]-5,8-difluoro-13,13-dimethyl-3,13-dihydro-indeno[2',3':3,4]naphtho[1,2-b]pyran.

Example 32

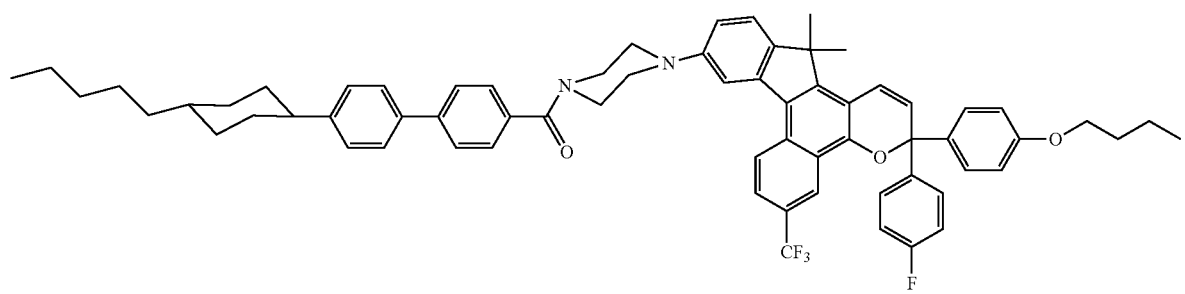 [SMILES: CCCCCC1CCC(c2ccc(-c3ccc(C(=O)N4CCN(c5ccc6c(c5)-c5c(c7c(c8cc(C(F)(F)F)ccc58)OC(c5ccc(F)cc5)(c5ccc(OCCCC)cc5)C=C7)C6(C)C)CC4)cc3)cc2)CC1]

Step 1

Procedures from Step 1 to Step 5 of Example 10 were followed.

Step 2

To degassed dioxane (100 mL) and toluene (100 mL) in a reaction flask was added 2,2'-bis(diphenylphosphino)-1,1'-binaphthyl (1.20 g), palladium (II) acetate (0.30 g) and 8,10-dibromo-7,7-dimethyl-3-(trifluoromethyl)-7H-benzo[c]fluoren-5-ylacetate (5.10 g) from Step 5 of Example 10, followed by the addition of 1-formylpiperazine (2.80 g) under a stream of nitrogen. Sodium tert-butoxide (2.80 g) was added and the solution was heated to reflux for 22 h. The reaction mixture was cooled to room temperature and diluted with tetrahydrofuran. The solution was filtered through CELITE® filtering aid and the filtrate was concentrated under vacuum. The residue was purified by column chromatography using 1:4 methylene chloride and ethyl acetate mixtures as the eluent. Fractions containing the desired material were grouped and concentrated. The residue (1.25 g) was used directly in the next step. NMR analysis of the residue indicated a structure that was consistent with 4-(8-bromo-5-hydroxy-7,7-dimethyl-3-(trifluoromethyl)-7H-benzo[c]fluoren-10-yl)piperazine-1-carbaldehyde.

Step 3

4-(8-Bromo-5-hydroxy-7,7-dimethyl-3-(trifluoromethyl)-7H-benzo[c]fluoren-10-yl)piperazine-1-carbaldehyde from Step 2 (0.69 g) and 1-(4-butoxyphenyl)-1-(4-fluorophenyl)prop-2-yn-1-ol (0.60 g) were dissolved in 1,2-dichloroethane (20 mL) in a reaction flask. p-Toluenesulfonic acid (0.1 g) was added and the solution was heated to reflux for 18 h. The reaction mixture was cooled to room temperature and the solvent was removed in vacuo. The residue was purified by column chromatography using 1:1 hexanes and dichloromethane mixtures as the eluent. Fractions containing the desired material were grouped and concentrated. The residue (0.75 g) was used directly in the next step.

Step 4

The product of Step 3,4-(12-Bromo-3-(4-butoxyphenyl)-3-(4-fluorophenyl)-13,13-dimethyl-6-(trifluoromethyl)-3,13-dihydrobenzo[h]indeno[2,1-f]chromen-10-yl)piperazine-1-carbaldehyde (2.00 g) was dissolved in dioxane (30 mL) in a reaction flask. 10% HCl aq (5 mL) was added and the solution was heated to reflux for 2 h. The reaction mixture was cooled to room temperature and carefully poured into saturated aqueous sodium bicarbonate solution (300 mL). The resulting aqueous layer was extracted with ethyl acetate (300 mL). The ethyl acetate solution was dried with anhydrous sodium sulfate, filtered and concentrated to provide a residue. The residue was purified by column chromatography using 1:1 ethyl acetate and methanol mixture as the eluent. Fractions containing the desired material were grouped and concentrated. The residue (1.00 g) was used directly in the next step.

Step 5

Procedure from Step 3 of Example 26 was followed using the residue of Step 4 above in place of 12-bromo-3-(4-butoxyphenyl)-3-(4-fluorophenyl)-10-[4-hydroxybenzamido]-6-trifluoromethyl-13,13-dimethyl-3,13-dihydro-indeno[2',3':3,4]naphtho[1,2-b]pyran. NMR indicated that the structure was consistent with 3-(4-fluorophenyl)-3-(4-butoxyphenyl)-10-[(4-(4'-(4-trans-pentylcyclohexyl)-[1,1'-biphenyl]-4-yl)carbonyl)piperazin-1-yl]-6-trifluoromethyl-13,13-dimethyl-3,13-dihydro-indeno[2',3':3,4]naphtho[1,2-b]pyran.

Example 33

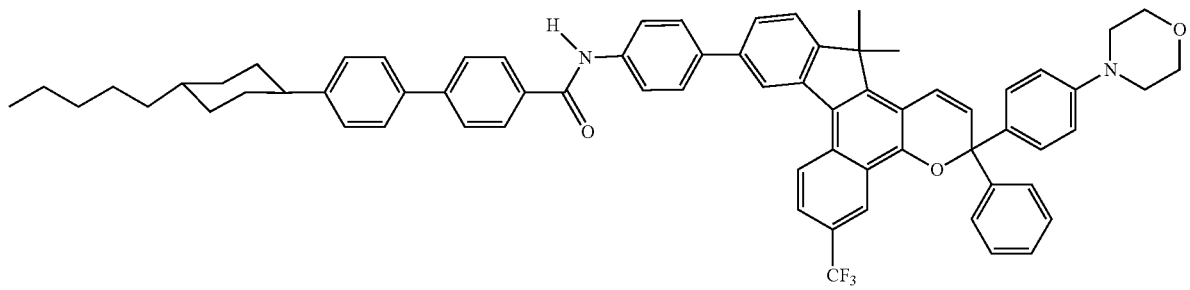 [SMILES: CCCCCC1CCC(c2ccc(-c3ccc(C(=O)Nc4ccc(-c5ccc6c(c5)-c5c(c7c(c8cc(C(F)(F)F)ccc58)OC(c5ccccc5)(c5ccc(N8CCOCC8)cc5)C=C7)C6(C)C)cc4)cc3)cc2)CC1]

The procedures from Example 14 were followed except that in Step 6,1-(4-N-morpholinophenyl)-1-(4-phenyl)prop-2-yn-1-ol was used in place of 1-(4-butoxyphenyl)-1-(4-fluorophenyl)prop-2-yn-1-ol. NMR analysis indicated that the product had a structure consistent with 3-(4-(N-morpholino)phenyl)-3-phenyl-10-[4-(4-(4-(4-trans-pentylcyclohexyl)phenyl)benzamido)phenyl]-6-trifluoromethyl-13,13-dimethyl-3,13-dihydro-indeno[2',3':3,4]naphtho[1,2-b]pyran.

Example 34

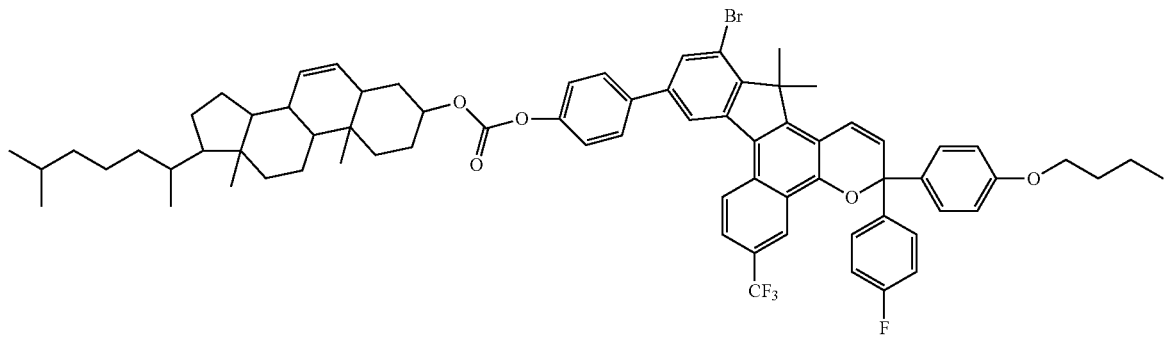 [SMILES: CCCCOc1ccc(C2(c3ccc(F)cc3)C=Cc3c4c(c5ccc(C(F)(F)F)cc5c3O2)-c2cc(-c3ccc(OC(=O)OC5CCC6(C)C(C=CC7C6CCC6(C)C(C(C)CCCC(C)C)CCC76)C5)cc3)cc(Br)c2C4(C)C)cc1]

Step 1

The procedures from Example 10 were followed except that in Step 6,1-(4-butoxyphenyl)-1-(4-fluorophenyl)prop-2-yn-1-ol was used in place of 1,1-bis(4-methoxyphenyl)prop-2-yn-1-ol and in Step 7,4-(4,4,5,5-tetramethyl-1,3,2-dioxaborolan-2-yl)phenol was used in place of 4'-(4-trans-pentylcyclohexyl)-N-(4-(4,4,5,5-tetramethyl-1,3,2-dioxaborolan-2-yl)phenyl)-[1,1'-biphenyl]-4-carboxamide. NMR analysis of the product indicated a structure that was consistent with 3-(4-butoxyphenyl)-3-(4-fluorophenyl)-10-(4-hydroxyphenyl)-6-trifluoromethyl-12-bromo-13,13-dimethyl-indeno[2',3':3,4]naphtho[1,2-b]pyran.

Step 2

The product from Step 1,3-(4-butoxyphenyl)-3-(4-fluorophenyl)-10-(4-hydroxyphenyl)-6-trifluoromethyl-12-bromo-13,13-dimethyl-indeno[2',3':3,4]naphtho[1,2-b]pyran (1.00 g), was added to a reaction flask and dissolved in dichloromethane (20 mL). Triethylamine (0.2 mL) was added followed by cholesteryl chloroformate (0.90 g) and the reaction mixture was stirred for 30 min. The solvent was removed in vacuo and the residue was purified by column chromatography using 19:1 hexanes and ethyl acetate mixture as the eluent. Fractions containing the desired material were grouped and concentrated. The residue was dissolved in a minimum amount of dichloromethane and added drop-wise to vigorously stirred methanol. The precipitate was collected by vacuum filtration and dried to provide a purple solid. NMR analysis of the purple solid indicated structure that was consistent with 3-(4-butoxyphenyl)-3-(4-fluorophenyl)-10-{-4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]phenyl}-6-trifluoromethyl-12-bromo-13,13-dimethyl-3,13-dihydro-indeno[2',3':3,4]naphtho[1,2-b]pyran.

Part 2—Photochromic Property Testing

Part 2A—Test Square Preparation

Testing was done with the compounds described in Examples 1-3,5,7, and 10-34 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2E0 DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on an optical bench, the test squares from Part 2A were conditioned by exposing them to 365 nm ultraviolet light for 10 minutes at a distance of about 14 cm from the source in order to pre-activate the photochromic compounds in samples. The UVA irradiance at the sample surface was measured with a Licor Model Li-1800 spectroradiometer and found to be 22.2 Watts per square meter. The samples were then placed under a halogen lamp (500 W, 120V) for about 10 minutes at a distance of about 36 cm from the lamp in order to bleach, or inactivate, the photochromic compounds in the samples. The illuminance at the sample was measured with the Licor spectroradiometer and found to be 21.9 Klux. The samples were then kept in a dark environment for at least 1 hour prior to testing in order to cool and continue to fade back to a ground state.

The optical bench was fitted with an Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72° F.±2° for photochromic response testing. A Newport Model 689456 Digital Exposure Timer was used to control the intensity of the xenon arc lamp during activation of the sample.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at 31° normal to its surface while being perpendicular to the monitoring light.

Samples were activated in the 73° F. (22.8° C.) controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half life is the time interval in seconds for the ΔOD of the activated form of the photochromic compound in the test squares to reach one half the ΔOD measured after thirty minutes, or after saturation or near-saturation was achieved, at room temperature after removal of the source of activating light, e.g., by closing the shutter. Results are listed in Table I.

TABLE 1

Photochromic Performance Test Results

| Example # | $\lambda_{max\text{-}vis}$ (nm) | Sensitivity (ΔOD/Min) | ΔOD at saturation | T ½ (sec) |
| --- | --- | --- | --- | --- |
| 1 | 592 | 0.56 | 0.71 | 122 |
| 2 | 629 | 0.45 | 0.34 | 44 |
| 3 | 556 | 0.65 | 0.62 | 62 |
| 5 | 602 | 0.45 | 0.35 | 47 |
| 7 | 456 | 0.48 | 0.85 | 168 |
| 10 | 568 | 0.30 | 0.13 | 19 |
| 11 | 577 | 0.35 | 0.16 | 23 |
| 12 | 538 | 0.49 | 0.36 | 46 |
| 13 | 576 | 0.44 | 0.37 | 51 |
| 14 | 572 | 0.53 | 0.41 | 49 |
| 15 | 610 | 0.42 | 0.30 | 43 |
| 16 | 607 | 0.46 | 0.43 | 65 |

TABLE 1-continued

Photochromic Performance Test Results

| Example # | $\lambda_{max-vis}$ (nm) | Sensitivity ($\Delta$OD/Min) | $\Delta$OD at saturation | T ½ (sec) |
|---|---|---|---|---|
| 17 | 573 | 0.41 | 0.25 | 33 |
| 18 | 616 | 0.47 | 0.45 | 62 |
| 19 | 610 | 0.48 | 0.44 | 60 |
| 20 | 558 | 0.40 | 0.21 | 27 |
| 21 | 564 | 0.52 | 0.45 | 54 |
| 22 | 560 | 0.50 | 0.36 | 42 |
| 23 | 563 | 0.45 | 0.34 | 45 |
| 24 | 562 | 0.52 | 0.53 | 74 |
| 25 | 584 | 0.46 | 0.20 | 18 |
| 26 | 552 | 0.44 | 0.21 | 22 |
| 27 | 580 | 0.77 | 0.70 | 82 |
| 28 | 564 | 0.52 | 0.39 | 45 |
| 29 | 587 | 1.06 | 0.77 | 61 |
| 30 | 588 | 0.48 | 0.22 | 22 |
| 31 | 547 | 0.75 | 0.85 | 96 |
| 32 | 577 | 0.55 | 0.44 | 53 |
| 33* | 605 | 0.46 | 0.44 | 60 |
| 34 | 555 | 0.39 | 0.19 | 21 |

*Indicates that Example 33 was tested after an exposure level of 2.0 rather than 6.7 W/m² in order to obtain a measurable reading.

Part 3—Dichroic Property Testing

Part 3A—Liquid Crystal Cell Preparation

The average absorption ratio of each of the compounds of Examples 1-8, 10-30, and 33 was determined according to the CELL METHOD described as follows.

A cell assembly having the following configuration was obtained from Design Concepts, Inc. Each of the cell assemblies was formed from two opposing glass substrates that are spaced apart with a glass bead spacer having a diameter of 20 microns +/−1 micron. The inner surfaces of each of the glass substrates had oriented polyimide coating thereon to provide for the alignment of a liquid crystal mate rial as discussed below. Two opposing edges of the glass substrates were sealed with an epoxy sealant, leaving the remaining two edges open for filling.

The gap between the two glass substrates of the cell assembly was filled with a liquid crystal solution containing the one of the compounds of Examples 1-33. The liquid crystal solution was formed by mixing the following components in the weight percents listed below with heating, if necessary, to dissolve the test material.

| Material | Weight Percent |
|---|---|
| Licristal ™ E7 | 97-99.5 |
| Example Compound | 0.5-3 |

Part 3B—Liquid Crystal Cell Testing

An optical bench was used to measure the optical properties of the cell and derive the absorption ratios for each of the Test Materials. The filled cell assembly was placed on the optical bench with an activating light source (an Oriel Model 66011 300-Watt Xenon arc lamp fitted with a Vincent Associates (model VS25S2ZM0R3 with VMM-D4 controller) high-speed computer controlled shutter that momentarily closed during data collection so that stray light would not interfere with the data collection process, a Schott 3 mm KG-1 band-pass filter, which removed short wavelength radiation, neutral density filter(s) for intensity attenuation and a condensing lens for beam collimation) positioned at a 30° to 35° angle of incidence a surface of the cell assembly.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing.

Polarization of the light source was achieved by passing the light from the single end of the cable through a Moxtek, Proflux Polarizer held in a computer driven, motorized rotation stage (Model M-061-PD from Polytech, PI). The monitoring beam was set so that the one polarization plane)(0° was perpendicular to the plane of the optical bench table and the second polarization plane)(90° was parallel to the plane of the optical bench table. The samples were run in air, at room temperature (73° F.±0.3° F. or better (22.8° C.±) 0.1°) maintained by the lab air conditioning system or a temperature controlled air cell.

To conduct the measurements, the cell assembly and the coating stack were exposed to 6.7 W/m² of UVA from the activating light source for 5 to 15 minutes to activate the Test Material. This was done for all of the Examples except Example 33, when tested in the coating stack, it was exposed to 2.0 W/m² of UVA. The lower exposure level was needed to obtain measurable results. An International Light Research Radiometer (Model IL-1700) with a detector system (Model SED033 detector, B Filter, and diffuser) was used to verify exposure prior to each test. Light from the monitoring source that was polarized to the 0° polarization plane was then passed through the coated sample and focused on a 1" integrating sphere, which was connected to an Ocean Optics S2000 spectrophotometer using a single function fiber optic cable. The spectral information, after passing through the sample, was collected using Ocean Optics SpectraSuite and PPG propriety software. While the photochromic-dichroic material was activated, the position of the polarizer was rotated back and forth to polarize the light from the monitoring light source to the 90° polarization plane and back. Data was collected for approximately 10 to 300 seconds at 5-second intervals during activation. For each test, rotation of the polarizers was adjusted to collect data in the following sequence of polarization planes: 0°, 90°, 90°, 0°, etc.

Absorption spectra were obtained and analyzed for each cell assembly using the Igor Pro software (available from WaveMetrics). The change in the absorbance in each polarization direction for each cell assembly was calculated by subtracting out the 0 time (i.e., unactivated) absorption measurement for the cell assembly at each wavelength tested. Average absorbance values were obtained in the region of the activation profile where the response of the Examples 1-33 was saturated or nearly saturated (i.e., the regions where the measured absorbance did not increase or did not increase significantly over time) for each cell assembly by averaging absorbance at each time interval in this region. The average absorbance values in a predetermined range of wavelengths corresponding $\lambda_{max\text{-}vis}$ +/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the Test Material was then calculated by averaging these individual absorption ratios.

For the Examples listed in Table 2 the above-described procedure was run at least twice. The tabled value for the Average Absorption Ratio represents an average of the results obtained from the runs measured at the wavelength indicated. The results of these tests are present in Table 2 below.

TABLE 2

Absorption Ratio (AR) Test Data

| Example # | Wavelength (nm) | Absorption Ratio |
|---|---|---|
| 1 | 592 | 6.56 |
| 2 | 629 | 8.04 |
| 3 | 555 | 6.86 |
| 4 | 556 | 4.75 |
| 5 | 601 | 6.96 |
| 6 | 601 | 5.98 |
| 7 | 456 | 8.68 |
| 8 | 600 | 7.51 |
| 10 | 565 | 6.15 |
| 11 | 572 | 3.80 |
| 12 | 536 | 6.85 |
| 13 | 579 | 6.84 |
| 14 | 565 | 6.89 |
| 15 | 605 | 7.36 |
| 16 | 606 | 5.49 |
| 17 | 571 | 6.23 |
| 18 | 610 | 8.71 |
| 19 | 605 | 7.11 |
| 20 | 555 | 6.60 |
| 21 | 562 | 5.03 |
| 22 | 560 | 5.58 |
| 23 | 560 | 6.84 |
| 24 | 561 | 7.25 |
| 25 | 579 | 8.16 |
| 26 | 557 | 5.71 |
| 27 | 584 | 7.06 |
| 28 | 567 | 5.07 |
| 29 | 587 | 8.49 |
| 30 | 587 | 7.24 |
| 33* | 606 | 7.80 |

*Indicates that Example 33 (of Table 2) was tested after an exposure level of 2.0 rather than 6.7 W/m² in order to obtain a measurable reading.

Part 3C—Preparation of Coatings for Aligned Liquid Crystal Coated Substrates

Part 3C-1—Preparation of Primer

Into a 250 mL amber glass bottle equipped with a magnetic stir-bar following materials were added in the order and amounts indicated:
Polyacrylate polyol (15.2334 g) (Composition D of Example 1 in U.S. Pat. No. 6,187,444, which polyol disclosure is incorporated herein by reference);
Polyalkylenecarbonate diol (40.0000 g) T-5652 from Asahi Kasei Chemicals;
DESMODUR® PL 340 (33.7615 g) from Bayer Material Science;
TRIXENE® BI 7960 (24.0734 g) from Baxenden);
Polyether modified polydimethylsiloxane (0.0658 g) BYK®-333 from BYK-Chemie GmbH);
Urethane catalyst (0.8777 g) KKAT® 348 from King Industries;
γ-Glycidoxypropyltrimethoxysilane (3.5109 g) A-187 from Momentive Performance Materials;
Light stabilizer (7.8994 g) TINUVIN® 928 from Ciba Specialty Chemicals; and
1-Methyl-2-pyrrolidinone (74.8250 g) from Sigma-Aldrich).

The mixture was stirred at room temperature for 2 hrs to yield a solution having 50 weight % final solids based on the total weight of the solution.

Part 3C-2—Preparation of Photo-Alignment Coating Component

Staralign 2200CP10 purchased from Ventico was diluted to 2% solution with cyclopentanone solvent.

Part 3C-3—Liquid Crystal Coating Components and Formulations

Liquid crystal monomers (LCM) used for monomer solution include the following:
LCM-1 is 1-(6-(6-(6-(6-(6-(6-(6-(6-(8-(4-(4-(4-(8-acryloyloxyhexyloxy)benzoyloxy)phenyloxycarbonyl)phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexyloxy)-6-oxohexan-1-ol which was prepared according to the procedures described in Example 17 of U.S. Patent Publication 2009/0323011, which liquid crystal monomer disclosure is incorporated herein by reference.

LCM-2 is commercially available RM257 reported to be 4-(3-acryloyloxypropyloxy)-benzoic acid 2-methyl-1,4-phenylene ester, available from EMD Chemicals, Inc., having the molecular formula of $C_{33}H_{32}O_{10}$.

LCM-3 is commercially available RM105 reported to be 4-methoxy-3-methylphenyl 4-(6-(acryloyloxy)hexyloxy) benzoate, available from EMD Chemicals, Inc., having the molecular formula of $C_{23}H_{26}O_6$.

LCM-4 is commercially available RM82 reported to be 2-methyl-1,4-phenylene bis(4-(6-(acryloyloxy)hexyloxy) benzoate), available from EMD Chemicals, Inc., having the molecular formula of $C_{39}H_{44}O_{10}$.

Liquid crystal coating formulation (LCCF) was prepared as follows: to a suitable flask containing a mixture of anisole (3.4667 g) and BYK®-346 additive (0.0347 g, reported to be a polyether modified poly-dimethyl-siloxane available from BYK Chemie, USA), was added LCM-1 (1.3 g), LCM-2 (1.3 g), LCM-3 (1.3 g), LCM-4 (1.3 g), 4-methoxyphenol (0.0078 g), and IRGACURE® 819 (0.078 g, a photoinitiator available from Ciba-Geigy Corporation) and the Example compounds listed in Table 3 in a concentration of 6.3 mmol per 100 g of LCCF. The resulting mixture was stirred for 2 hours at 80° C. and cooled to about 26° C.

Part 3C-4: Transitional Layer Coating Formulation (TLCF)

The TLCF was prepared as follows:
In a 50 mL amber glass bottle equipped with a magnetic stir-bar following materials were added:
Hydroxy methacrylate (1.242 g) from Sigma-Aldrich;
Neopentyl glycol diacrylate (13.7175 g) SR247 from Sartomer;
Trimethylolpropane trimethacrylate (2.5825 g) SR350 from Sartomer;

DESMODUR® PL 340 (5.02 g) from Bayer Material Science;

IRGACURE®-819 (0.0628 g) from Ciba Speciality Chemicals;

DAROCUR® TPO (0.0628 g; from Ciba Speciality Chemicals,

Polybutyl acrylate (0.125 g),

3-Aminopropylpropyltrimethoxysilane (1.4570 g) A-1100 from Momentive Performance Materials; and 200 proof absolute anhydrous Ethanol (1.4570 g) from Pharmaco-Aaper.

The mixture was stirred at room temperature for 2 hrs.

Part 3C-5: Protective Coating Formulation (PCF)

The PCF (Hard Coat) was prepared as follows: Charge 1 was added to a clean dry beaker and placed in an ice bath at 5 C with stirring. Charge 2 was added and an exotherm raised the temperature of the reaction mixture to 50 C. The temperature of the resulting reaction mixture was cooled to 20-25 C and Charge 3 was added with stirring. Charge 4 was added to adjust the pH from about 3 to about 5.5. Charge 5 was added and the solution was mixed for half an hour. The resulting solution was filtered through a nominal 0.45 micron capsule filter and stored at 4° C. until use.

| Charge 1 | |
| --- | --- |
| glycidoxypropyltrimethoxysilane | 32.4 grams |
| methyltrimethoxysilane | 345.5 grams |
| Charge 2 | |
| Solution of deionized water (DI) with nitric acid (nitric acid 1 g/7000 g) | 292 grams |
| Charge 3 | |
| DOWANOL ® PM solvent | 228 grams |
| Charge 4 | |
| TMAOH (25% tetramethylamonium hydroxide in methanol) | 0.45 grams |
| Charge 5 | |
| BYK ®-306 surfactant | 2.0 grams |

Part 3C-6—Procedures Used for Preparing Coating Stacks Reported in Table 3 art 3C-6A—Substrate Preparation

Square substrates measuring 5.08 cm by 5.08 cm by 0.318 cm (2 inches (in.) by 2 in. by 0.125 in.) prepared from CR-39® monomer were obtained from Homalite, Inc. Each substrate prepared from CR-39® monomer was cleaned by wiping with a tissue soaked with acetone and dried with a stream of air.

Each of the aforementioned substrates was corona treated by passing on a conveyor belt in Tantec EST Systems Serial No. 020270 Power Generator HV 2000 series corona treatment equipment with a high voltage transformer. The substrates were exposed to corona generated by 53.99 KV, 500 Watts while traveling on a conveyor at a belt speed 3 ft/min.

Part 3C-6B—Coating Procedure for Primer

The primer solution was applied to the test substrates by spin-coating on a portion of the surface of the test substrate by dispensing approximately 1.5 mL of the solution and spinning the substrates at 500 revolutions per minute (rpm) for 3 seconds, followed by 1,500 rpm for 7 seconds, followed by 2,500 rpm for 4 seconds. A spin processor from Laurell Technologies Corp. (WS-400B-6NPP/LITE) was used for spin coating. Afterwards, the coated substrates were placed in an oven maintained at 125° C. for 60 minutes. The coated substrates were cooled to about 26° C. The substrate was corona treated by passing on a conveyor belt in Tantec EST Systems Serial No. 020270 Power Generator HV 2000 series corona treatment equipment with a high voltage transformer. The dried primer layer were exposed to corona generated by 53.00 KV, 500 Watts while traveling on a conveyor at a belt speed 3 ft/min.

Part 3C-6C—Coating Procedure for Photo-Alignment Materials

The 2 wt % Staralign 2200 solutions prepared in Part 3C-2 was applied to the test substrates by spin-coating on a portion of the surface of the test substrate by dispensing approximately 1.0 mL of the solution and spinning the substrates at 800 revolutions per minute (rpm) for 3 seconds, followed by 1,000 rpm for 7 seconds, followed by 4,000 rpm for 4 seconds. A spin processor from Laurell Technologies Corp. (WS-400B-6NPP/LITE) was used for spin coating. Afterwards, the coated substrates were placed in an oven maintained at 120° C. for 30 minutes. The coated substrates were cooled to about 26° C.

The dried photo alignment layer on each of the substrates was at least partially ordered by exposure to linearly polarized ultraviolet radiation using a DYMAX® UVC-6 UV/conveyor system by DYMAX® Corp. having a 400 Watt power supply. The light source was oriented such that the radiation was linearly polarized in a plane perpendicular to the surface of the substrate. The amount of ultraviolet radiation that each photoalignment layer was exposed to was measured using a UV Power Puck™ High energy radiometer from EIT Inc (Serial No. 2066) and was as follows: UVA 0.121 W/cm$^2$ and 5.857 J/cm$^2$; UVB 0.013 W/cm$^2$ and 0.072 J/cm$^2$; UVC 0 W/cm$^2$ and 0 J/cm$^2$; and UVV 0.041 W/cm$^2$ and 1.978 J/cm$^2$. After ordering at least a portion of the photo-orientable polymer network, the substrates were cooled to about 26° C. and kept covered.

Part 3C-6D—Coating Procedure for Liquid Crystal Coating Formulations

The Liquid Crystal Coating Formulations ("LCCF") described in Part 3C-3 were each spin coated at a rate of 300 revolutions per minute (rpm) for 6 seconds, followed by 800 rpm for 6 seconds onto the at least partially ordered photoalignment materials of Part 6C on the test substrates. Each coated square substrate was placed in an oven at 50° C. for 20 minutes and each coated lens was placed in an oven at 50° C. for 30 minutes. Afterwards substrates were cured under an ultraviolet lamp in the Irradiation Chamber BS-03 from Dr. Gröbel UV-Elektronik GmbH in a nitrogen atmosphere for 30 minutes at a peak intensity of 11-16 Watts/m$^2$ of UVA. Post curing of the coated substrates was completed at 105° C. for 3 hours.

Part 3C-6E—Coating Procedure for Transitional Layer

The Transitional layer solution prepared in Part 3C-4 was spin coated at a rate of 1,400 revolutions per minute (rpm) for 7 seconds onto the cured LCCF coated substrates. Afterwards, the lenses were cured under an ultraviolet lamp in the Irradiation Chamber BS-03 from Dr. Dr. Gröbel UV-Elektronik GmbH in a nitrogen atmosphere for 30 minutes at a peak intensity of 11-16 Watts/m² of UVA. Post curing of the coated substrates was completed at 105° C. for 3 hours.

Part 3C-6F—Coating Procedure for the Protective Coating (Hard Coat)

The hard coat solution prepared in Part 3C-5 was spin coated at a rate of 2,000 revolutions per minute (rpm) for 10 seconds onto the cured tie layer coated substrates. Post curing of the coated substrates was completed at 105° C. for 3 hours.

TABLE 3

Absorption Ratio Results for Different Coating Stacks

| Example # | Primer | Alignment Layer | LCCF | Tie Layer | Hard Coat | AR |
|---|---|---|---|---|---|---|
| 8 |  | x | x |  |  | 6.18 |
| 13 |  | x | x |  |  | 6.61 |
| 12 |  | x | x |  |  | 5.38 |
| 17 |  | x | x |  |  | 5.49 |
| 18 |  | x | x |  |  | 7.14 |
| 8 |  | x | x | x |  | 5.96 |
| 17 |  | x | x | x |  | 5.32 |
| 18 |  | x | x | x |  | 7.05 |
| 13 |  | x | x |  | x | 6.53 |
| 33 | x | x | x | x |  | 7.12 |
| 12 | x | x | x | x |  | 5.24 |
| 17 | x | x | x | x |  | 5.13 |
| 33 | x | x | x |  |  | 7.62 |
| 33 | x | x | x | x | x | 7.13 |
| 12 | x | x | x | x | x | 4.77 |

The present invention has been described with reference to specific details of particular embodiments thereof. It is not intended that such details be regarded as limitations upon the scope of the invention except insofar as to the extent that they are included in the accompanying claims.

What is claimed:
1. A compound represented by the following graphic Formula I:

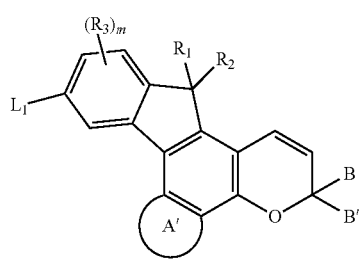

Formula I wherein:
A' is selected from optionally substituted heteroaryl and optionally substituted aryl wherein A' is optionally substituted with $L_2$;
$R_1$ and $R_2$ are each independently selected from hydrogen, hydroxy and chiral or achiral groups selected from optionally substituted heteroalkyl, optionally substituted alkyl, optionally substituted alkenyl, optionally substituted alkynyl, optionally substituted aryl, optionally substituted heteroaryl, optionally substituted cycloalkyl, optionally substituted heterocycloalkyl, halogen, optionally substituted amino, carboxy, alkylcarbonyl, alkoxycarbonyl, optionally substituted alkoxy, and aminocarbonyl, or $R_1$ and $R_2$ may be taken together with any intervening atoms to form a group selected from oxo, optionally substituted cycloalkyl, and optionally substituted heterocycloalkyl; and $R_3$ for each occurrence, is independently selected from chiral or achiral groups selected from formyl, alkylcarbonyl, alkoxycarbonyl, aminocarbonyl, arylcarbonyl, aryloxycarbonyl, aminocarbonyloxy, alkoxycarbonylamino, aryloxycarbonylamino, boronic acid, boronic acid esters, cycloalkoxycarbonylamino, heterocycloalkyloxycarbonylamino, heteroaryloxycarbonylamino, optionally substituted alkyl, optionally substituted alkenyl, optionally substituted alkynyl, halogen, optionally substituted cycloalkyl, optionally substituted aryl, optionally substituted heteroaryl, optionally substituted alkoxy, optionally substituted heteroalkyl, optionally substituted heterocycloalkyl, and optionally substituted amino;

m is an integer selected from 0 to 3;

B and B' are each independently selected from $L_3$, hydrogen, halogen, and chiral or achiral groups selected from metallocenyl, optionally substituted alkyl, optionally substituted alkenyl, optionally substituted alkynyl, optionally substituted heteroalkyl, optionally substituted alkoxy, optionally substituted aryl, optionally substituted heteroaryl, optionally substituted heterocycloalkyl, and optionally substituted cycloalkyl, or wherein B and B' are taken together with any intervening atoms to form a group selected from optionally substituted cycloalkyl and optionally substituted heterocycloalkyl; and $L_1$, $L_2$, and $L_3$ for each occurrence, are independently selected from a chiral or achiral lengthening group represented by: —$[S_1]_c$-$[Q_1$-$[S_2]_d]_{d'}$-$[Q_2$-$[S_3]_e]_{e'}$-$[Q_3$-$[S_4]_f]_{f'}$—$S_5$—P wherein:

(a) $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl;

wherein substituents are independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;

wherein said straight-chain $C_1$-$C_{18}$ alkyl and branched $C_1$-$C_{18}$ alkyl are mono-substituted with a group selected from cyano, halogen, and $C_1$-$C_{18}$ alkoxy; or wherein said straight-chain $C_1$-$C_{18}$ alkyl and branched $C_1$-$C_{18}$ alkyl are poly-substituted with at least two groups independently selected from halogen, -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;

(b) c, d, e, and f are each independently chosen from an integer from 1 to 20; and each $S_1$, $S_2$, $S_3$, $S_4$, and $S_5$ is independently chosen for each occurrence from a spacer unit selected from:
  (i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl;
  (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl; and
  (iii) —O—, —C(=O)—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen,
  provided that when two spacer units comprising heteroatoms are linked together the spacer units are linked so that heteroatoms are not directly linked to each other, each bond between $S_1$ and the compound represented by graphic Formula I is free of two heteroatoms linked together, and the bond between $S_5$ and P is free of two heteroatoms linked to each other;
(c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl; hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor or P is a substituted or unsubstituted photochromic compound; and
(d) d', e' and f' are each independently chosen from 0, 1, 2, 3, and 4, provided that a sum of d'+e'+f' is at least 2.

2. The compound of claim 1 represented by graphic Formula IA:

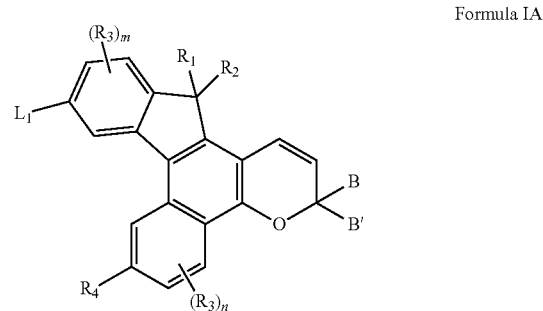

Formula IA wherein
$R_4$ is selected from hydrogen, $R_3$ and $L_2$; and
n is an integer selected from 0 to 3.

3. The compound of claim 2, wherein
$R_1$ and $R_2$ are each independently selected from hydrogen, hydroxy, and chiral and achiral groups selected from optionally substituted heteroalkyl, optionally substituted alkyl, optionally substituted aryl, optionally substituted heteroaryl, optionally substituted cycloalkyl, halogen, optionally substituted amino, carboxy, alkylcarbonyl, alkoxycarbonyl, optionally substituted alkoxy, and aminocarbonyl or $R_1$ and $R_2$ may be taken together with any intervening atoms to form a group selected from oxo, optionally substituted cycloalkyl and optionally substituted heterocycloalkyl;
$R_3$ for each occurrence, is independently selected from formyl, alkylcarbonyl, alkoxycarbonyl, aminocarbonyl, arylcarbonyl, aryloxycarbonyl, optionally substituted alkyl, boronic acid ester, halogen, optionally substituted cycloalkyl, optionally substituted aryl, optionally substituted alkoxy, optionally substituted heteroalkyl, optionally substituted heterocycloalkyl and optionally substituted amino;
m and n are each independently an integer selected from 0 to 2;
B and B' are each independently selected from $L_3$ hydrogen, halogen, chiral or achiral groups selected from optionally substituted alkyl, optionally substituted alkenyl, optionally substituted heteroalkyl, optionally substituted alkoxy, optionally substituted aryl, optionally substituted heteroaryl, and optionally substituted cycloalkyl, or wherein B and B' are taken together with any intervening atoms to form a group selected from optionally substituted cycloalkyl and optionally substituted heterocycloalkyl; and
$L_1$, $L_2$, and $L_3$ for each occurrence, are independently selected from a chiral or achiral lengthening group represented by:
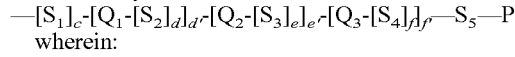
wherein:
(a) $Q_1$, $Q_2$, and $Q_3$ for each occurrence, are independently selected from a divalent group selected from optionally substituted aryl and optionally substituted heteroaryl, optionally substituted cycloalkyl and optionally optionally substituted heterocycloalkyl;
wherein substituents are independently selected from P, liquid crystal mesogens, halogen, poly($C_1$-$C_{12}$ alkoxy), $C_1$-$C_{12}$ alkoxycarbonyl, $C_1$-$C_{12}$ alkylcarbonyl, perfluoro($C_1$-$C_{12}$) alkoxy, perfluoro($C_1$-$C_{12}$)alkoxycarbonyl, perfluoro($C_1$-$C_{12}$)alkylcarbonyl, $C_1$-$C_{18}$ acetyl, $C_3$-$C_7$ cycloalkyl, $C_3$-$C_7$ cycloalkoxy, straight-chain $C_1$-$C_{12}$ alkyl, and branched $C_1$-$C_{12}$ alkyl,
wherein said straight-chain $C_1$-$C_{12}$ alkyl and branched $C_1$-$C_{12}$ alkyl are mono-substituted with a group selected from, halogen, $C_1$-$C_{12}$ alkoxy, or
wherein said straight-chain $C_1$-$C_{12}$ alkyl and branched $C_1$-$C_{12}$ alkyl are poly-substituted with at least two groups independently selected from halogen;
  (b) c, d, e, and f are each independently chosen from an integer from 1 to 10; and each $S_1$, $S_2$, $S_3$, $S_4$, and $S_5$ is independently chosen for each occurrence from a spacer unit selected from:
    (i) substituted or unsubstituted alkylene, substituted or unsubstituted haloalkylene, —Si($CH_2$)$_g$—, and —(Si[($CH_3$)$_2$]O)$_h$—, wherein g for each occurrence is independently chosen from an integer from 1 to 10; h for each occurrence is independently chosen from an integer from 1 to 8; and said substitutes for the alkylene and haloalkylene are independently selected from $C_1$-$C_{12}$ alkyl, $C_3$-$C_7$ cycloalkyl and phenyl;
    (ii) —N(Z)—, —C(Z)=C(Z)—, and a single bond, wherein Z for each occurrence is independently selected from hydrogen, $C_1$-$C_{12}$ alkyl, $C_3$-$C_7$ cycloalkyl and phenyl; and
    (iii) —O—, —C(=O)—, —N=N—, —S—, and —S(=O)—,
    provided that when two spacer units comprising heteroatoms are linked together the spacer units are linked so that heteroatoms are not directly linked to each other, each bond between $S_1$ and the compound represented by graphic Formula IA is free of two heteroatoms linked together, and the bond between $S_5$ and P is free of two heteroatoms linked to each other;
  (c) P for each occurrence is selected from hydroxy, amino, $C_2$-$C_{12}$ alkenyl, $C_2$-$C_{12}$ alkenyl, silyl, siloxy, (tetrahydro-2H-pyran-2-yl)oxy, isocyanato, acryloyloxy, methacryloyloxy, epoxy, carboxylic acid, carboxylic ester, $C_1$-$C_{12}$ alkyloxycarbonyloxy, halocarbonyl, hydrogen, aryl, hydroxy($C_1$-$C_{12}$)alkyl, $C_1$-$C_{12}$ alkyl, $C_1$-$C_{12}$ alkoxy, ethylene, acryloyl, acryloyloxy($C_1$-$C_{12}$)alkyl, methacryloyl, methacryloyloxy($C_1$-$C_{12}$)alkyl, oxetanyl, glycidyl, vinyl ether, siloxane derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, wherein each substituent is independently chosen from $C_1$-$C_{12}$ alkyl, $C_1$-$C_{12}$ alkoxy, amino, $C_3$-$C_7$ cycloalkyl, $C_1$-$C_{12}$ alkyl($C_1$-$C_{12}$)alkoxy, or fluoro($C_1$-$C_{12}$)alkyl, or P is a structure having from 2 to 4 reactive groups; and
  (d) d', e' and f' are each independently chosen from 0, 1, 2, 3, and 4, provided that a sum of d'+e'+f is at least 2.

4. The compound of claim 3 wherein:
$R_1$ and $R_2$ are each independently selected from hydrogen, hydroxy, and chiral groups selected from optionally substituted heteroalkyl, optionally substituted alkyl, optionally substituted aryl, optionally substituted cycloalkyl, halogen, carboxy, alkylcarbonyl, alkoxycarbonyl, optionally substituted alkoxy, and aminocarbonyl or $R_1$ and $R_2$ may be taken together with any intervening atoms to form a group selected from oxo and optionally substituted cycloalkyl; and
$R_3$ for each occurrence, is independently selected from alkylcarbonyl, alkoxycarbonyl, aminocarbonyl, optionally substituted alkyl, boronic acid ester, halogen, optionally substituted cycloalkyl, optionally substituted aryl, optionally substituted alkoxy, optionally substituted heterocycloalkyl and optionally substituted amino;
m and n are each independently an integer selected from 0 to 2;
B and B' are each independently selected from $L_3$, hydrogen, chiral groups selected from optionally substituted alkyl, optionally substituted alkenyl, optionally substituted aryl, optionally substituted heteroaryl, and optionally substituted cycloalkyl, or wherein B and B' are taken together with any intervening atoms to form a group selected from optionally substituted cycloalkyl;
$L_1$, $L_2$, and $L_3$ for each occurrence, are independently selected from a chiral or achiral lengthening group represented by:
—[$S_1$]-[$Q_1$—[$S_2$]$_d$]$_{d'}$-[$Q_2$—[$S_3$]$_e$]$_{e'}$-[$Q_3$—[$S_4$]$_f$]$_{f'}$—$S_5$—P
wherein:
(a) $Q_1$, $Q_2$, and $Q_3$ for each occurrence, are independently selected from a divalent group selected from optionally substituted aryl and optionally substituted heteroaryl, optionally substituted cycloalkyl and optionally optionally substituted heterocycloalkyl;
wherein substituents are independently selected from P, $C_1$-$C_6$alkoxycarbonyl, perfluoro($C_1$-$C_6$)alkoxy, $C_3$-$C_7$ cycloalkyl, $C_3$-$C_7$ cycloalkoxy, straight-chain $C_1$-$C_6$ alkyl, and branched $C_1$-$C_6$ alkyl,
wherein said straight-chain $C_1$-$C_6$ alkyl and branched $C_1$-$C_6$ alkyl are mono-substituted with a group selected from halogen and $C_1$-$C_{12}$ alkoxy, or
wherein said straight-chain $C_1$-$C_6$ alkyl and branched $C_1$-$C_6$ alkyl are poly-substituted with at least two groups independently selected from halogen;
(b) c, d, e, and f are each independently chosen from an integer from 1 to 10; and each $S_1$, $S_2$, $S_3$, $S_4$, and $S_5$ is independently chosen for each occurrence from a spacer unit selected from:
  (i) substituted or unsubstituted alkylene;
  (ii) —N(Z)—, —C(Z)=C(Z)—, and a single bond, wherein Z for each occurrence is independently selected from hydrogen and $C_1$-$C_6$ alkyl; and
  (iii) —O—, —C(=O)—, —C≡C—, and —N=N—, —S—;
  provided that when two spacer units comprising heteroatoms are linked together the spacer units are linked so that heteroatoms of the first spacer unit are not directly linked to the heteroatoms of the second spacer unit, and
  provided that when $S_1$ and $S_5$ are linked to Formula I and P, respectively, they are linked so that two heteroatoms are not directly linked to each other;
(c) P for each occurrence is independently selected from hydroxy, amino, $C_2$-$C_6$ alkenyl, $C_2$-$C_6$ alkenyl, siloxy, (tetrahydro-2H-pyran-2-yl)oxy, isocyanato, acryloyloxy, methacryloyloxy, epoxy, carboxylic acid, carboxylic ester, $C_1$-$C_6$ alkyloxycarbonyloxy, hydrogen, aryl, hydroxy($C_1$-$C_6$)alkyl, $C_1$-$C_6$ alkyl, ethylene, acryloyl, acryloyloxy($C_1$-$C_{12}$)alkyl, oxetanyl, glycidyl, vinyl ether, siloxane derivatives, and substituted or unsubstituted chiral or non-chiral monovalent or divalent groups chosen from steroid radicals, wherein each substituent is independently chosen from $C_1$-$C_6$ alkyl, $C_1$-$C_6$ alkoxy, amino, $C_3$-$C_7$, cycloalkyl.

5. The compound of claim 4 wherein: R₁ and R₂ are each independently selected from methyl, ethyl, propyl and butyl; R₃ and R₄ for each occurrence are independently selected from methyl, ethyl, bromo, chloro, fluoro, methoxy, ethoxy and CF₃, B and B' are each independently selected from phenyl substituted with one or more groups independently selected from aryl, heteroaryl, heterocycloalkyl, alkyl, alkenyl, alkynyl, alkoxy, halogen, amino, alkylcarbonyl, carboxy, and alkoxycarbonyl; and for L₁: Q₁ is unsubstituted aryl; e' is 1 or 2; e each occurrence is 1; S₃ for each occurrence is a single bond; Q₂ for each occurrence is independently selected from optionally substituted aryl; f' is 1; f is 1; S₄ is a single bond; and Q₃ is optionally substituted cycloalkyl; S₅ is —(CH₂)_g—, wherein g is an integer from 1 to 20; and P is hydrogen.

6. The compound of claim 1 wherein L₁ is selected from:
4-[4-(4-butyl-cyclohexyl)-phenyl]-cyclohexyloxy;
4'''-butyl-[1,1',4',1'']tercyclohexan-4-yloxy;
4-[4-(4-butyl-phenyl)-cyclohexyloxycarbonyl]-phenoxy;
4'-(4-butyl-benzoyloxy)-biphenyl-4-carbonyloxy;
4-(4-pentyl-phenylazo)-phenylcarbamoyl;
4-(4-dimethylamino-phenylazo)-phenylcarbamoyl;
4-[5-(4-propyl-benzoyloxy)-pyrimidin-2-yl]-phenyl
4-[2-(4'-methyl-biphenyl-4-carbonyloxy)-1,2-diphenyl-ethoxycarbonyl]-phenyl;
4-(1,2-diphenyl-2-{3-[4-(4-propyl-benzoyloxy)-phenyl]-acryloyloxy}-ethoxycarbonyl)-phenyl;
4-[4-(4-{4-[3-(6-{4-[4-(4-nonyl-benzoyloxy)-phenoxy-carbonyl]-phenoxy}-hexyloxycarbonyl)propionyloxy]-benzoyloxy}-benzoyloxy)phenyl]-piperazin-1-yl;
4-[4-(4-{4-[4-(4-nonyl-benzoyloxy)-benzoyloxy]-benzoyloxy}-benzoyloxy)-phenyl]-piperazin-1-yl;
4-(4'-propyl-biphenyl-4-ylethynyl)-phenyl;
4-(4-fluoro-phenoxycarbonyloxy)-piperidin-1-yl;
2-[17-(1,5-dimethyl-hexyl)-10,13-dimethyl-2,3,4,7,8,9, 10,11, 12,13,14,15,16,17-tetradecahydro-1H-cyclopenta[a]phenanthren-3-yloxy]-indan-5-yl;
4-[17-(1,5-dimethyl-hexyl)-10,13-dimethyl-2,3,4,7,8,9, 10,11, 12,13,14,15,16,17-tetradecahydro-1H-cyclopenta phenanthren-3-yloxycarbonyloxy]-piperidin-1-yl;
4-(biphenyl-4-carbonyloxy)-piperidin-1-yl;
4-(naphthalene-2-carbonyloxy)-piperidin-1-yl;
4-(4-phenylcarbamoyl-phenylcarbamoyl)-piperidin-1-yl;
4-(4-(4-phenylpiperidin-1-yl)-benzoyloxy)-piperidin-1-yl;
4-butyl-[1,1';4',1'']terphenyl-4-yl;
4-(4-pentadecafluoroheptyloxy-phenylcarbamoyl)-benzyloxy;
4-(3-piperidin-4-yl-propyl)-piperidin-1-yl;
4-(4-{4-[17-(1,5-dimethyl-hexyl)-10,13-dimethyl-2,3,4, 7,8,9,10,11,12,13,14,15,16,17-tetradecahydro-1H-cyclopenta[a]phenanthren-3-yloxycarbonyloxy]-benzoyloxy}-phenoxycarbonyl)phenoxymethyl;
4-[4-(4-cyclohexyl-phenylcarbamoyl)-benzyloxy]-piperidin-1-yl;
4-[4-(4-cyclohexyl-phenylcarbamoyl)-benzoyloxy]-piperidin-1-yl;
N-{4-[(4-pentyl-benzylidene)amino]-phenyl}-acetamidyl;
4-(3-piperidin-4-yl-propyl)piperidin-1-yl;
4-(4-hexyloxy-benzoyloxy)-piperidin-1-yl;
4-(4'-hexyloxy-biphenyl-4-carbonyloxy)-piperidin-1-yl;
4-(4-butyl-phenylcarbamoyl)-piperidin-1-yl;
4-[4-[4-[4-piperidinyl-4-oxy]-phenyl]phenoxy)piperidin-4-yl;
4-(4-(9-(4-butylphenyl)-2,4,8,10-tetraoxaspiro[5.5]undec-3-yl)phenyl)piperazin-1-yl;
4-(6-(4-butylphenyl)carbonyloxy-(4,8-dioxabicyclo [3.3.0]oct-2-yl))oxycarbonyl)phenyl;
1-{4-[5-(4-butyl-phenyl)-[1,3]dioxan-2-yl]-phenyl}-4-methyl-piperazin-1-yl;
4-(7-(4-propylphenylcarbonyloxy)bicyclo[3.3.0]oct-2-yl) oxycarbonyl)phenyl;
4-[17-(1,5-dimethyl-hexyl)-10,13-dimethyl-2,3,4,7,8,9, 10,11, 12,13,14,15,16,17-tetradecahydro-1H-cyclopenta[a]phenanthren-3-yloxycarbonyloxy;
(4-trans-(4-pentylcyclohexyl)benzamido)phenyl;
(4-(4-trans-(4-pentylcyclohexyl)phenoxy)carbonyl)phenyl;
4-(4-(4-trans-(4-pentylcyclohexyl)phenyl)benzamido) phenyl;
4-((trans-(4'-pentyl-[1,1'-bi(cyclohexan)]-4-yl)oxy)carbonyl)phenyl;
4-(4'-(4-pentylcyclohexyl)-[1,1'-biphenyl]-4-ylcarboxamido)phenyl;
4-((4(4'-(4-pentylcyclohexyl)-[1,1'-biphenyl]-4-carbonyl) oxy)benzamido;
4-(4'-(4-pentylcyclohexyl)-[1,1'-biphenyl]-4-carbonyl) piperazin-1-yl;
4-(4-(4-pentylcyclohexyl)phenyl)benzamido)-2-(trifluoromethyl)phenyl;
2-methyl-4-trans-(4-((4'-trans-(4-pentylcyclohexyl)biphenyl-4-yloxy)carbonyl)cyclohexanecarboxamido) phenyl;
4'-((1r,1's,4R,4'R)-4'-pentylbi(cyclohexane-4-)carbonyloxy)biphenylcarbonyloxy;
4-(((3S,8S,9S,10R,13R,14S,17R)-10,13-dimethyl-17-(R)-6-methylheptan-2-yl)-2,3,4,7,8,9,10,11,12,13,14, 15,16,17-tetradecahydro-1H-cyclopenta[a]phenanthren-3-yloxy)carbonyl)piperazin-1-yl; and
4-((S)-2-methylbutoxy)phenyl)-10-(4-(((3R,3aS,6S,6aS)-6-(4'-trans-(4-pentylcyclohexyl)biphenylcarbonyloxy) hexahydrofuro[3,2-b]furan-3-yloxy)carbonyl)phenyl.

7. The compound of claim 1 selected from:
3,3-Bis(4-methoxyphenyl)-10-[4-(4-(trans-4-pentylcyclohexyl)benzamido)phenyl]-13,13-dimethyl-12-bromo-3,13-dihydro-indeno[2',3':3,4]naphtho[1,2-b] pyran;
3,3-Bis(4-methoxyphenyl)-10-[4-((4-(trans-4-pentylcyclohexyl)phenoxy)carbonyl)phenyl]-6,13,13-trimethyl-3,13-dihydro-indeno[2',3':3,4]naphtho[1,2-b]pyran;
3-(4-Fluorophenyl)-3-(4-piperidinophenyl)-10-[4-(4-(4-(trans-4-pentylcyclohexyl)phenyl)benzamido) phenyl]-6-trifluoromethyl-11,13,13-trimethyl-3,13-dihydro-indeno[2',3':3,4]naphtho[1,2-b]pyran;
3,3-Bis(4-methoxyphenyl)-10-[4-(4-(trans-4-pentylcyclohexyl)benzamido)phenyl]-5,7-difluoro-13,13-dimethyl-3,13-dihydro-indeno[2',3':3,4]naphtho[1,2-b]pyran;
3-(4-Methoxyphenyl)-3-(4-piperidinophenyl)-10-[4-(4-(4-(trans-4-pentylcyclohexyl)phenyl)benzamido) phenyl]-5,7-difluoro-13,13-dimethyl-3,13-dihydro-indeno[2',3':3,4]naphtho[1,2-b]pyran;
3-(4-Methoxyphenyl)-3-(4-morpholinophenyl)-10-[4-(4-(trans-4-pentylcyclohexyl)phenyl)benzamido)phenyl]-5,7-difluoro-13,13-dimethyl-3,13-dihydro-indeno [2',3':3,4]naphtho[1,2-b]pyran;
3-(4-Fluorophenyl)-3-(4-piperidinophenyl)-10-[4-((4-(trans-4-pentylcyclohexyl)phenoxy)carbonyl)phenyl]-12-bromo-5,7-difluoro-13,13-dimethyl-3,13-dihydro-indeno[2',3':3,4]naphtho[1,2-b]pyran;

3-Phenyl-3-(4-piperidinophenyl)-10-[4-(4-(4-(trans-4-pentylcyclohexyl)phenyl)benzamido)phenyl]-12-bromo-5,7-difluoro-13,13-dimethyl-3,13-dihydro-indeno[2',3':3,4]naphtho[1,2-b]pyran;

3-Phenyl-3-(4-piperidinophenyl)-10-[4-(4-(4-(trans-4-pentylcyclohexyl)phenoxy)carbonyl)phenyl]-12-bromo-5,7-difluoro-13,13-dimethyl-3,13-dihydro-indeno[2',3':3,4]naphtho[1,2-b]pyran;

3-(4-Fluorophenyl)-3-(4-piperidinophenyl)-10-[4-(4-(4-(trans-4-pentylcyclohexyl)phenyl)benzamido)phenyl]-12-bromo-13,13-dimethyl-3,13-dihydro-indeno[2',3':3,4]naphtho[1,2-b]pyran;

3,3-Bis(4-methoxydinophenyl)-10-[4-(4-(4-(trans-4-pentylcyclohexyl)phenyl)benzamido)phenyl]-12-bromo-6,7-dimethoxy-11,13,13-trimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido) phenyl]-6-trifluoromethyl-12-bromo-13,13-dimethyl-3,13-dihydro-indeno[2',3':3,4]naphtho[1,2-b]pyran;

3,3-Bis(4-methoxyphenyl)-10,12-bis[4-(4-(4-(trans-4-pentylcyclohexyl)phenyl)benzamido)phenyl-6-trifluoromethyl-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-5,7-difluoro-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido) phenyl]-6-trifluoromethyl-13,13-dimethyl-3,13-dihydro-indeno[2',3':3,4]naphtho[1,2-b]pyran;

3,3-Bis(4-methoxyphenyl)-10-[4-(4-(4-(trans-4-pentylcyclohexyl)phenyl)benzamido)phenyl]-5,7-difluoro-12-bromo-13,13-dimethyl-3,13-dihydro-indeno[2',3':3,4]naphtho[1,2-b]pyran;

3-(4-Fluorophenyl)-3-(4-morpholinophenyl)-10-[4-(4-(4-(trans-4-pentylcyclohexyl)phenyl)benzamido)phenyl]-6-trifluoromethyl-13-methyl-13-butyl-3,13-dihydro-indeno[2',3':3,4]naphtho[1,2-b]pyran;

3-(4-Fluorophenyl)-3-(4-morpholinophenyl)-10-[4-(4-(4-(trans-4-pentylcyclohexyl)phenyl)benzamido)phenyl]-5,7-difluoro-12-bromo-13,13-dimethyl-3,13-dihydro-indeno[2',3':3,4]naphtho[1,2-b]pyran;

3-Phenyl-3-(4-methoxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3-Phenyl-3-(4-morpholinophenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3,3-Bis(4-fluorophenyl)-10-[4-(4-(4-(trans-4-pentylcyclohexyl)phenyl)benzamido)phenyl]-6-trifluoromethyl-12-bromo-13,13-dimethyl-3,13-dihydro-indeno[2',3':3,4]naphtho[1,2-b]pyran;

3,3-Bis(4-fluorophenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3-(4-Methoxyphenyl)-3-(4-butoxyphenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran;

3-(4-Fluorophenyl)-13,13-dimethyl-3-(4-morpholinophenyl)-10-(4-(4'-(trans-4-pentylcyclohexyl)-[1,1'-biphenyl]-4-ylcarboxamido)phenyl)-6-(trifluoromethyl)-3,13-dihydro-indeno[2',3':3,4]naphtho[1,2-b]pyran;

3-(4-Butoxyphenyl)-3-(4-fluorophenyl)-13,13-dimethyl-10-(4-(4'-(trans-4-pentylcyclohexyl)-[1,1'-biphenyl]-4-ylcarboxamido)phenyl)-6-(trifluoromethyl)-3,13-dihydro-indeno[2',3':3,4]naphtho[1,2-b]pyran;

3-(4-(4-(4-Methoxyphenyl)piperazin-1-yl)phenyl)-13,13-dimethyl-10-(4-(4'-(trans-4-pentylcyclohexyl)-[1,1'-biphenyl]-4-ylcarboxamido)phenyl)-3-phenyl-6-(trifluoromethyl)-3,13-dihydro-indeno[2',3':3,4]naphtho[1,2-b]pyran;

3-(4-Butoxyphenyl)-3-(4-fluorophenyl)-13,13-dimethyl-10-(4-(((trans,trans-4'-pentyl-[1,1'-bi(cyclohexan)]-4-yl)oxy)carbonyl)phenyl)-6-(trifluoromethyl)-3,13-dihydro-indeno[2',3':3,4]naphtho[1,2-b]pyran;

3-(4-Fluorophenyl)-13,13-dimethyl-10-(4-(4'-(trans-4-pentylcyclohexyl)-[1,1'-biphenyl]-4-ylcarboxamido)phenyl)-3-(4-butoxyphenyl)-6-(trifluoromethyl)-3,13-dihydro indeno[2',3':3,4]naphtho[1,2-b]pyran;

3-(4-Methoxyphenyl)-13,13-dimethyl-10-(4-(4'-(trans-4-pentylcyclohexyl)-[1,1'-biphenyl]-4-ylcarboxamido)phenyl)-3-(4-(trifluoromethoxy)phenyl)-6-(trifluoromethyl)-3,13-dihydro-indeno[2',3':3,4]naphtho[1,2-b]pyran;

3,3-Bis(4-hydroxyphenyl)-10-[4-(4-(4-(trans-4-pentylcyclohexyl)phenyl)benzamido) phenyl]-6-trifluoromethyl-13,13-dimethyl-3,13-dihydro-indeno[2',3':3,4]naphtho[1,2-b]pyran;

12-Bromo-3-(4-butoxyphenyl)-3-(4-fluorophenyl)-13,13-dimethyl-10-(4-((4'-(trans-4-pentylcyclohexyl)-[1,1'-biphenyl]-4-carbonyl)oxy)benzamido)-6-(trifluoromethyl)-3,13-dihydro-indeno[2',3':3,4]naphtho[1,2-b]pyran;

3-(4-Butoxyphenyl)-5,7-dichloro-11-methoxy-3-(4-methoxyphenyl)-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

3-(4-Butoxyphenyl)-3-(4-fluorophenyl)-13,13-dimethyl-10-(4-((4'-(trans-4-pentylcyclohexyl)-[1,1'-biphenyl]-4-carbonyl)oxy)benzamido)-6-(trifluoromethyl)-3,13-dihydro-indeno[2',3':3,4]naphtho[1,2-b]pyran;

5,7-Dichloro-3,3-bis(4-hydroxyphenyl)-11-methoxy-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

6,8-Dichloro-3,3-bis(4-hydroxyphenyl)-11-methoxy-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

3-(4-Butoxyphenyl)-5,8-difluoro-3-(4-fluorophenyl)-13,13-dimethyl-10-(4-(4'-(trans-4-pentylcyclohexyl)-[1,1'-biphenyl]-4-ylcarboxamido)phenyl)-3,13-dihydro-indeno[2',3':3,4]naphtho[1,2-b]pyran;

3-(4-Butoxyphenyl)-3-(4-fluorophenyl)-13,13-dimethyl-10-(4-(4'-(trans-4-pentylcyclohexyl)-[1,1'-biphenyl]-4-carbonyl)piperazin-1-yl)-6-(trifluoromethyl)-3,13-dihydro-indeno[2',3':3,4]naphtho[1,2-b]pyran;

3-(4-Morpholinophenyl)-3-(4-methoxyphenyl)-10,7-bis[4-(4-(4-(trans-4-pentylcyclohexyl)phenyl)benzamido)phenyl]-5-fluoro-13,13-dimethyl-3,13-dihydro-indeno[2',3':3,4]naphtho[1,2-b]pyran;

3-(4-Morpholinophenyl)-3-(4-methoxyphenyl)-10-[4-(4-(4-(trans-4-pentylcyclohexyl)phenyl)benzamido)-2-(trifluoromethyl)phenyl]-13,13-dimethyl-3,13-dihydro-indeno[2',3':3,4]naphtho[1,2-b]pyran;

3,3-Bis(4-methoxyphenyl)-10-[4-(4-(4-(trans-4-pentylcy-clohexyl)phenyl)benzamido)-2-(trifluoromethyl)phe-nyl]-13,13-dimethyl-3,13-dihydro-indeno[2',3':3,4]naphtho[1,2-b]pyran;

3-(4-Morpholinophenyl)-3-(4-methoxyphenyl)-10-[4-(4-(4-(trans-4-pentylcyclohexyl)phenypbenzamido)-2-(trifluoromethyl)phenyl]-13,13-dimethyl-3,13-dihydro-indeno[2',3':3,4]naphtho[1,2-b]pyran;

3,3-Bis(4-methoxyphenyl)-13,13-dimethyl-10-(2-methyl-4-(trans-4-((4'-((trans-4-pentylcyclohexyl)biphenyl-4-yloxy)carbonyl)cyclohexanecarboxamido)phenyl)-3,13-dihydro-indeno[2',3':3,4]naphtho[1,2-b]pyran;

3-(4-(4-(4-Butylphenyl)piperazin-1-yl)phenyl)-3-(4-methoxyphenyl)-13,13-dimethyl-10-(4-(4'-(trans-4-pentylcyclohexyl)biphenyl-4-ylcarboxamido)-2-(trifluoromethyl)phenyl)-3,13-dihydro-indeno[2',3':3,4]naphtho[1,2-b]pyran;

3-(4-(4-(4-Butylphenyl)piperazin-1-yl)phenyl)-3-(4-methoxyphenyl)-13,13-dimethyl-10-(2-methyl-4-(4'-(trans-4-pentylcyclohexyl)biphenyl-4-ylcarboxamido)phenyl)-7-(4-(4-(trans-4-pentylcyclohexyl)benzamido)phenyl)-3,13-dihydro-indeno[2',3':3,4]naphtho[1,2-b]pyran;

3-(4-Methoxyphenyl)-13,13-dimethyl-7,10-bis(4-(4'-(trans-4-pentylcyclohexyl)biphenyl-4-ylcarboxamido)phenyl)-3-phenyl-3,13-dihydro-indeno[2',3':3,4]naphtho[1,2-b]pyran;

3-p-Tolyl-3-(4-methoxyphenyl)-6-methoxy-13,13-dimethyl-7-(4'-(trans,trans-4'-pentylbi(cyclohexane-4-)carbonyloxy)biphenylcarbonyloxy)-10-(4-(4'-(trans-4-pentylcyclohexyl)biphenyl-4-ylcarboxamido)phenyl)-3,13-dihydro-indeno[2',3':3,4]naphtho[1,2-b]pyran;

10-(4-(((3S,8S,9S,10R,13R,14S,17R)-10,13-Dimethyl-17-(R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl)-3-(4-methoxyphenyl)-13,13-dimethyl-3-(4-morpholinophenyl)-3,13-dihydro-indeno[2',3':3,4]naphtho[1,2-b]pyran;

6-Methoxy-3-(4-methoxyphenyl)-13,13-dimethyl-3-(4-((S)-2-methylbutoxy)phenyl)-10-(4-(4'-(trans-4-pentylcyclohexyl)biphenyl-4-ylcarboxamido)phenyl)-3,13-dihydro-indeno[2',3':3,4]naphtho[1,2-b]pyran;

6-Methoxy-3-(4-methoxyphenyl)-13,13-dimethyl-3-(4-((S)-2-methylbutoxy)phenyl)-7-(4'-(trans,trans-4'-pentylbi(cyclohexane-4-)carbonyloxy)biphenylcarbonyloxy)-10-(4-(4'-(trans-4-pentylcyclohexyl)biphenyl-4-ylcarboxamido)phenyl)-3,13-dihydro-indeno[2',3':3,4]naphtho[1,2-b]pyran; and 6-Methoxy-3-(4-methoxyphenyl)-13,13-dimethyl-3-(4-((S)-2-methylbutoxy)phenyl)-10-(4-(((3R,3aS,6S,6aS)-6-(4'-(trans-4-pentylcyclohexyl)biphenylcarbonyloxy)hexahydrofuro[3,2-b]furan-3-yloxy)carbonyl)phenyl)-3,13-dihydro-indeno[2',3':3,4]naphtho[1,2-b]pyran.

8. The compound of claim 1, wherein said compound is a photochromic compound.

9. A photochromic composition comprising the compound of claim 8 and optionally at least one other photochromic compound, wherein said composition comprises:
(a) a single photochromic compound;
(b) a mixture of photochromic compounds;
(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

10. A photochromic composition comprising at least one compound of claim 8 incorporated into at least a portion of an organic material, said organic material being a polymeric material, an oligomeric material, a monomeric material or a mixture or combination thereof.

11. The photochromic composition of claim 10 wherein said polymeric material comprises liquid crystal materials, self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), polyethylene terephthalate), polyester, polysulfone, polyolefin, copolymers thereof, and/or mixtures thereof.

12. The photochromic composition of claim 10 wherein the photochromic composition further comprises at least one additive chosen from dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

13. The photochromic composition of claim 10 comprising a coating composition chosen from liquid crystal materials, self-assembling materials and film forming materials.

14. A photochromic article comprising a substrate and a photochromic compound according to claim 8 connected to at least a portion of a substrate.

15. The photochromic article of claim 14 comprising an optical element, said optical element being at least one of an ophthalmic element, a display element, a window, a mirror, packaging material and an active or passive liquid crystal cell element.

16. The photochromic article of claim 15, wherein the ophthalmic element comprises corrective lenses, non-corrective lenses, contact lenses, intra-ocular lenses, magnifying lenses, protective lenses, or visors.

17. The photochromic article of claim 14 wherein the substrate comprises a polymeric material and the photochromic material is incorporated into at least a portion of the polymeric material.

18. The photochromic article of claim 17 wherein the photochromic material is blended with at least a portion of the polymeric material, bonded to at least a portion of the polymeric material, and/or imbibed into at least a portion of the polymeric material.

19. The photochromic article of claim 14 wherein the photochromic article comprises a coating or film connected to at least a portion of the substrate, said coating or film comprising the photochromic material.

20. The photochromic article of claim 19 wherein said substrate is formed from organic materials, inorganic materials, or combinations thereof.

21. The photochromic article of claim 14 further comprising at least one additional at least partial coating chosen from photochromic coatings, anti-reflective coatings, linearly polarizing coatings, transitional coatings, primer coatings, adhesive coatings, reflective coatings, antifogging coatings, oxygen barrier coatings, ultraviolet light absorbing coatings, and protective coatings.

22. A photochromic article comprising
a substrate;
at least a partial coating of one alignment material;
at least one additional at least partial coating of a liquid crystal material; and
at least one compound of claim 8.

23. The photochromic article of claim 22 further comprising at least one additive chosen from dichroic dyes, non-dichroic dyes, alignment promoters, antioxidants, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

24. The photochromic article of claim 22, wherein the substrate is selected from glass, quartz, and polymeric organic materials.

25. The photochromic article of claim 22, wherein the at least one alignment material comprises a polymer network orientable by exposure to at least one of: a magnetic field, an electric field, linearly polarized infrared radiation, linearly polarized ultraviolet radiation, linearly polarized visible radiation and a shear force.

26. The photochromic article of claim 22, wherein said liquid crystal material is a liquid crystal polymer.

27. The photochromic article of claim 22, further comprising at least one primer coating, transitional coating, protective coating or a combination thereof.

28. The photochromic article of claim 27, wherein the transitional coating comprises an acrylate polymer.

29. The photochromic article of claim 27, wherein the protective coating comprises at least one siloxane derivative.

30. The photochromic article of claim 27, wherein the at least one primer coating comprises a polyurethane.

* * * * *